United States Patent
Oury et al.

(10) Patent No.: US 11,541,129 B2
(45) Date of Patent: Jan. 3, 2023

(54) NANORESERVOIR COATED MEDICAL DEVICES, BIOMATERIALS, AND BIOPROSTHETICS

(71) Applicant: Université de Liège, Angleur (BE)

(72) Inventors: Cécile Oury, Liège (BE); Christine Jérôme, Liège (BE); Christophe Detrembleur, Liège (BE); Patrizio Lancellotti, Liège (BE)

(73) Assignee: UNIVERSITÉ DE LIÈGE, Angleur (BE)

( * ) Notice: Subject to any disclaimer, the term of this patent is extended or adjusted under 35 U.S.C. 154(b) by 497 days.

(21) Appl. No.: 16/468,495

(22) PCT Filed: Dec. 28, 2017

(86) PCT No.: PCT/EP2017/084728
§ 371 (c)(1),
(2) Date: Jun. 11, 2019

(87) PCT Pub. No.: WO2018/122318
PCT Pub. Date: Jul. 5, 2018

(65) Prior Publication Data
US 2020/0085970 A1    Mar. 19, 2020

(30) Foreign Application Priority Data

Dec. 28, 2016 (EP) .................................... 16207179

(51) Int. Cl.
| | |
|---|---|
| *A61K 47/69* | (2017.01) |
| *A61K 47/58* | (2017.01) |
| *A61L 27/34* | (2006.01) |
| *A61L 27/54* | (2006.01) |
| *A61L 31/10* | (2006.01) |
| *A61L 31/16* | (2006.01) |

(52) U.S. Cl.
CPC .......... *A61K 47/6903* (2017.08); *A61K 47/58* (2017.08); *A61L 27/34* (2013.01); *A61L 27/54* (2013.01)

(58) Field of Classification Search
CPC ..... A61K 47/58; A61K 47/6903; A61L 27/34; A61L 27/54; A61L 31/10; A61L 31/16
See application file for complete search history.

(56) References Cited

U.S. PATENT DOCUMENTS

2008/0255677 A1   10/2008 Libera
2009/0324685 A1 * 12/2009 Falk ........................ A61L 31/10
                                                   424/426

OTHER PUBLICATIONS

Faure et al.; Adv. Functional Materials; 2012, 22, pp. 5271-5282 (legible copy). Published 2012.*
Faure, Emilie, et al. "Functional nanogels as platforms for imparting antibacterial, antibiofilm, and antiadhesion activities to stainless steel." Advanced Functional Materials 22.24 (2012): 5271-5282.
Faure, Emilie, et al. "A green and bio-inspired process to afford durable anti-biofilm properties to stainless steel." Biofouling 28.7 (2012): 719-728.
International Searching Authority, International Search Report and Written Opinion for applicaton PCT/EP2017/084728, dated Apr. 12, 2018, 9 pages.
Wei, Q. et al., 2005, Mater. Horiz. 2015, 2: 567-577 Universal polymer coatings and their representative biomedical applications.

* cited by examiner

*Primary Examiner* — Jeffrey T. Palenik
(74) *Attorney, Agent, or Firm* — Quarles & Brady LLP

(57) ABSTRACT

Disclosed herein are biomaterial implants, medical devices, or bioprostheses wherein a surface or part thereof is coated with a nanoreservoir comprising a hydrophilic polymer or copolymer backbone crosslinked to a second polymer comprising a hydrophilic backbone and one or more reactive moieties, wherein the nanoreservoir further comprises one or more bioactive molecules, therapeutic molecules, or drugs.

13 Claims, 41 Drawing Sheets

A

B

C

Figure 1:
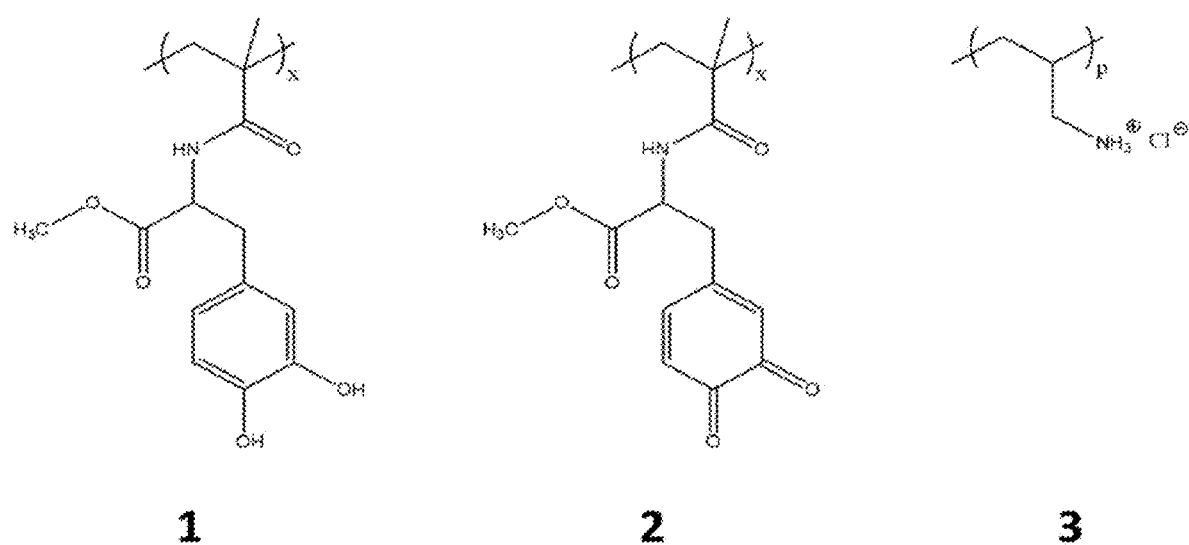

A.

B.

A.

B.

NANORESERVOIR COATED MEDICAL DEVICES, BIOMATERIALS, AND BIOPROSTHETICS

This application represents the national stage entry of PCT International Application No. PCT/EP2017/084728, filed on Dec. 28, 2017, which claims priority to EP Application No. 16207179.9, filed Dec. 28, 2016, each of which is incorporated by reference herein as if set forth in its entirety.

The present invention relates to nanoreservoirs, methods of making such nanoreservoirs and the uses thereof, in particular the use of nanoreservoirs suited for coating medical devices.

Medical devices and biomaterial implants are clinically used in a variety of applications with their performance being critical to a patient's overall health and quality of life.

Most medical devices raise biocompatibility issues. Importantly, implantation of foreign materials in blood vasculature activates the contact pathway of coagulation, which may lead to thrombotic complications. In particular, there is a medical need to improve the biocompatibility and durability of prosthetic heart valves which are currently among the most widely used cardiovascular devices. Mechanical prosthetic heart valves have a substantial risk of thromboemboli and thrombotic obstruction often requiring chronic anti-coagulation therapy which is in turn associated with an increased risk of haemorrhagic complications. In contrast, despite bio-prosthetic heart valves having a lower risk of thromboembolism without anti-coagulation, their durability is limited by calcific or non-calcific tissue deterioration.

Medical devices and biomaterials may also become infected and treatment for such infections generally requires removal of the entire component/system and administration of antibiotics targeting the causative bacteria.

As highlighted above, there is a need for the creation of an anti-bacterial, anti-biofilm, anti-thrombotic, anti-inflammatory and/or anti-calcification product that can be anchored or attached onto the surface of a biomaterial or medical device.

Previous attempts have been made to modify the surfaces of biomaterials and medical devices in order to improve the biocompatibility of blood contacting devices. Surface modification strategies have also been adopted to prevent biomaterial contamination with bacteria such as coating surfaces of biomaterials and medical devices with silver which has antimicrobial properties. However, none of these surface modifications provide the combined properties of, for example, antibacterial, anti-biofilm, anti-thrombotic and anti-calcification.

The present invention relates to nanoreservoirs such as nanogels which provide for a larger cargo space which may be used to incorporate bioactive compounds. Such nanoreservoirs can be anchored or attached onto the surface of any biomaterial or medical device, be it metallic or polymeric, or on a bioprosthesis and thereby reduce or prevent infection and improve biocompatibility and hemocompatibility of transiently or permanently implanted materials to help maintain their functionality and increase their durability.

According to a first aspect of the invention, there is provided a nanoreservoir comprising a first polymer and a second polymer, the first polymer bearing one or more catechol moieties; and the second polymer comprising a hydrophilic backbone with one or more reactive moieties.

The nanoreservoir may refer to a nanoparticle, preferably comprising a nanogel, which is composed of a hydrogel with a cross-linked hydrophilic polymer network. Nanogels are most often composed of synthetic polymers or biopolymers which are chemically or physically crosslinked. The pores in nanogels can be filled with small molecules or macromolecules, and their properties, such as swelling, degradation, and chemical functionality, can be controlled.

In an embodiment of the invention, the nanoreservoir comprises nanoparticles formed from a nanogel. A nanoparticle is any particle wherein the longest dimension is less than 1000 nm, e.g. about 10 nm to 300 nm. For example, the nanoreservoir may have a longest dimension of less than about 500 nm, less than about 300 nm, less than about 200 nm, less than about 150 nm, less than about 100 nm, less than about 50 nm, less than about 30 nm, less than about 10 nm or less than about 3 nm. In particular embodiments, the nanoreservoir of the present invention comprises nanoparticles which have a diameter of about 150 nm to about 250 nm. In particular embodiments, the nanoreservoir of the present invention comprises nanoparticles which have a diameter of about 100 to about 250 nm.

Preferably the nanoparticles in the nanoreservoir of the invention are made of the first and second polymer. The first and second polymers may be crosslinked.

The crosslinking between the first and second polymer may involve an amine-quinone reaction. Preferably the crosslinking does not use radical polymerisation.

The first polymer may have the structure as defined in Formula 1:

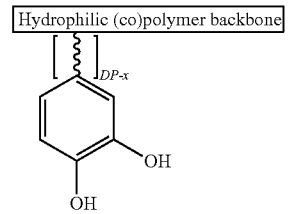

Formula 1 with DP = polymerization degree of the main chain
and x = can be 1 to DP-1

The catechol moiety may have the structure:

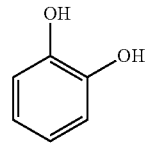

also known as benzene 1,2 diol.

The linker may be an alkyl ester, an N-alkylamide, an alkyl, or an alkoxy group.

The hydrophilic polymer or copolymer backbone may comprise one or more of polyallylamine, polyvinylamines, polyvinylamides, polyvinylalcohol, poly(metha)acrylates, poly(meth)acrylamide, polyurethane or PEG or a polyelectrolyte (cationic, anionic or zwitterionic) or a hydrophilic biopolymer such as a polysaccharide such as chitosan or hyaluronan.

The first polymer may be a polyDOPA, for example poly(N-methacryloyl 3,4-dihydroxy-L-phenylalanine methyl ester) also referred to as P(mDOPA) as illustrated below:

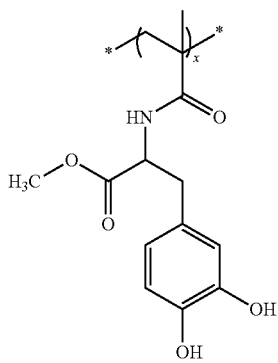

Before use P(mDOPA) may be oxidised to form Pox (mDOPA), as illustrated below:

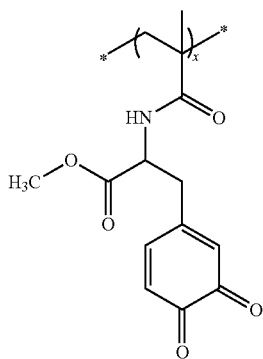

The first polymer may be P(mDOPA), or polyDOPA, or their copolymers with hydrophilic monomers (cationic, anionic, zwitterionic monomers, or neutral hydrosoluble monomer). In a preferred embodiment, the first polymer is a P(mDOPA) copolymer.

In the second polymer the hydrophilic backbone may comprise one or more of a polyallylamine, a polyvinylamine, a polyvinylamide, a polyvinylalcohol, a poly(meth)acrylate, a poly(meth)acrylamide, a polyurethane, a polyethylene glycol (PEG), a polyelectrolyte (cationic, anionic or zwitterionic) with reactive groups such as primary or secondary amines or thiol; or a hydrophilic biopolymer such as a polysaccharide such as chitosan or hyaluronan.

The reactive moiety may be a primary or secondary amine or a thiol.

The second polymer may be a natural or a synthetic polymer with a primary amine function, for example polyvinyl amine, chitosan or a protein. In a preferred embodiment, the second polymer may comprise a polyallylamine, such as poly(allylamine hydrochloride) also known as PAH, as illustrated below:

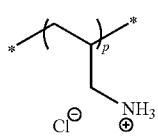

In a preferred embodiment the nanoreservoir comprises nanoparticles formed from crosslinked P(mDOPA) and PAH, which comprise one or both of the following bonds:

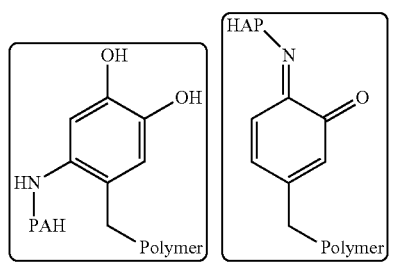

In a preferred embodiment, the nanoreservoir contains one or more bioactive molecules, therapeutic molecules or drugs, in addition to nanoparticles of crosslinked first and second polymers.

The nanoreservoir may be loaded with one or more bioactive agents such as bioactive molecules, therapeutic molecules or drugs including antibiotics, anti-biofilm formation agents, anti-platelet agents, anti-coagulants, anti-thrombotic agents, and anti-calcification agents. The bioactive agents may be located within the nanoparticles in the nanoreservoir and/or between the nanoparticles in the nanoreservoir.

Bioactive agents may include any agent which is desired to be delivered to molecules, cells, tissues or organs for modulating or otherwise modifying molecule or cell function, including for therapeutic effects. Bioactive agents include, but are not limited to, pharmaceutically active compounds or diagnostic compounds. Bioactive compounds include, but are not limited to, nucleotides (aptamers, RNAi, antisense oligonucleotides), peptides, oligopeptides, proteins, apoproteins, glycoproteins, antigens and antibodies or antibody fragments thereto, receptors and other membrane proteins, retro-inverso oligopeptides, protein analogs in which at least one non-peptide linkage replaces a peptide linkage, enzymes, coenzymes, enzyme inhibitors, amino acids and their derivatives, hormones, lipids, phospholipids, liposomes, ricin or ricin fragments; toxins such as aflatoxin, digoxin, xanthotoxin, rubratoxin; analgesics such as aspirin, ibuprofen and acetaminophen; bronchodilators such as theophylline and albuterol; beta-blockers such as propranolol, metoprolol, atenolol, labetolol, timolol, penbutolol and pindolol; antimicrobial agents such as those described above and ciprofloxacin, cinoxacin and norfloxacin; antihypertensive agents such as clonidine, methyldopa, prazosin, verapamil, nifedipine, aptopril and enalapril; cardiovascular agents including antiarrhythmics, cardiac glycosides, anti-anginals and vasodilators; central nervous system agents including stimulants, psychotropics, antimanics and depressants; antiviral agents; antihistamines such as chlorphenirmine and brompheniramine; cancer drugs including chemotherapeutic agents, such as chlorambucil, carboplatin, derivatives of busulfan, doxorubicin, etoposide, topotecan (TPT); tranquilizers such as diazepam, chordiazepoxide, oxazepam, alprazolam and triazolam, anti-depressants such as fluoxetine, amitriptyline, nortriptyline and imipramine; H-2 antagonists such as nizatidine, cimetidine, famotidine and ranitidine; anticonvulsants; antinauseants; prostaglandins; muscle relaxants; anti-inflammatory substances; stimulants; decongestants; antiemetics; diuretics; antispasmodics; antiasthmatiics; anti-Parkinson agents; expectorants; cough suppressants; mucolytics; vitamins; and mineral and nutritional additives. Other molecules include nucleotides; oligonucleotides; polynucleotides; and their art-recognized and biologically functional analogs and derivatives including, for example, methylated polynucleotides and nucleotide analogs having phosphorothioate linkages; plasmids, cosmids, artificial chromosomes, other nucleic acid vectors; antisense polynucleotides including those substantially complementary to at least one endogenous nucleic acid or those having sequences with a sense opposed to at least portions of selected viral or retroviral genomes; promoters; enhancers; inhibitors; other ligands for regulating gene transcription and translation.

The bioactive agent may be an anti-infective agent. Anti-infective agents include, but are not limited to antibiotics, such as amikacin, gentamicin, kanamycin, neomycin, netilmicin, tobramycin, paromomycin, streptomycin, spectinomycin, geldanamycin, herbimycin, rifaximin, loracarbef, ertapenem, dorpenem, imipenem/cilastatin, meropenem, cefadroxil, cefazolin, cefalotin, cephalexin, cefaclor, cefamandole, cefoxitin, cefproxil, cefuroxime, cefixime, cefdinir, cedfitoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, daibavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, amoxicillin, ampicillin, piperacillin, ticarcillin, bacitracin, colistin, polymyxin B, ciprofloxacin, enoxacin, gatifloxacin, gemifloxacin, levoflaxicin, lomefloxacilin, moxifloxacin, nalidixic acid, norfloxacin, ofloxacin, mafenide, sulfacetamide, sulfadizine, silver sulfadizine, sulfadimethoxine, sulfamethizole, sulfamethoxazole, sulfanilimide, sulfisoxazole, trimethoprim-sulfamethoxazole, sulfonamidochrysoidine, demeclocyline, doxycycline, minocycline, oxytetracycline, tetracycline, clofazimine, dapsone, rifampicin, rifabutin, arspehnamine, chloramphenicol, fosfomycin, metronidazole, thiamphenicol, tigecycline, tinidazole, and trimethoprim.

Anti-biofilm formation agents include, but are not limited to naturally occurring peptides such as human cathelicidin LL-37 or the bovine peptide indolicidin, or synthetic peptides such as 1018, natural compounds with 2-aminoimidazole moiety, 2-aminoimidazole based inhibitors, benzimidazoles analogs, indole-triazo-amide analogs, plant-derived biofilm inhibitors such as emodin, phloretin, casbane diterpene, resveratrol and its oligomers, sulphur derivatives, brominated furanone analogs, bromopyrrole alkaloids, skyllamycins and (−)-ageloxime D structures, cembranoids, N-acyl homoserine lactone analogs, carolacton, molecules that interfere with the formation of amyloid-like fibres, fatty acids, nitric oxide donors, ionic liquids as 1-alkyl-3-methyl imidazolium chloride, 1-alkylquinolinium bromide, all these agents can be used in combination with conventional antibiotics.

Anti-platelet agents include, but are not limited to, irreversible cyclooxygenase inhibitors such as aspirin and triflusal (Disgren), adenosine diphosphate (ADP) receptor inhibitors such as clopidogrel (Plavix), prasugrel (Effient), ticagrelor (Brilinta), ticlopidine (Ticlid), Phosphodiesterase inhibitors such as cilostazol (Pletal), Protease-activated receptor-1 (PAR-1) antagonists such as vorapaxar (Zontivity), glycoprotein IIB/IIIA inhibitors (intravenous use only) such as abciximab (ReoPro), eptifibatide (Integrilin), tirofiban (Aggrastat), Adenosine reuptake inhibitors such as dipyridamole (Persantine), thromboxane inhibitors, thromboxane synthase inhibitors and thromboxane receptor antagonists such as terutroban, glycoprotein VI inhibitors such as Revacept, glycoprotein Ib inhibitors, and von Willebrand factor inhibitors.

Anti-coagulants include, but are not limited, to acenocoumarol, coumatetralyl, dicoumarol, ethyl biscoumacetate, phenprocoumon, warfarin, clorindione, dipjenadione, phenindione, ticlomarol, bemiparin, certoparin, ardeparin, dalteparin, enoxaparin, nadroparin, parnaparin, reviparin, dabigatran, apixaban, betrixabaan, darexaban, edoxaban, otamixaban, rivaroxaban, alteplase, danaparoid, tinzaparin, and fondaparinux.

Thrombolytic agents include, but are not limited to, alteplase, reteplase, tenecteplase, saruplase, urokinase, anistreplase, monteplase, streptokinase, ancrod, brinase and fibrinolysin.

Anti-calcification agents include, but are not limited to, bisphosphonates, aluminium salts, glutaraldehyde, amino oleic acid, and metalloproteinase inhibitors.

In a preferred embodiment a nanoreservoir of the invention comprises nanoparticles of crosslinked first and second polymers, and at least one, preferably at least two, bioactive molecules, therapeutic molecules and/or drugs. The nanoreservoir may comprise an anti-platelet agent and/or an antibiotic. The bioactive molecules, therapeutic molecules or drugs may be encapsulated in the nanoparticles and/or may be covalently bound to reactive moieties of nanoparticles.

The nanoreservoir may comprise an antibiotic and an anti-platelet agent in a ratio of between about 1 part antibiotic and about 5 parts anti-platelet agent, or between about 2 parts antibiotic and about 3 parts anti-platelet agent.

In a further embodiment, hydrophilic functionalised ligands may be grafted onto the assembled crosslinked nanogel nanoparticles. The hydrophilic ligands may comprise thiol or vinyl end functionalised ligands. The functionalised ligands may comprise one or more PEG (polyethylene glycol) molecule and/or one or more vinyl end functionalised PEG ligand, such as PEG-acrylate molecules. Where PEG is used the PEG may be PEG 1.5 (Methoxy-PEG-(CH2)2-SH, Mw 2,000), PEG2 (Methoxy-PEG-(CH2) 2-SH, Mw 2,000), PEGS (Methoxy-PEG-(CH2)2-SH, Mw 5,000) or PEG10 (Methoxy-PEG-(CH2)2-SH, Mw 10,000). Where PEG-Acrylate (APEG) is used the molecule may be: APEG (polyethylene glycol methyl ether acrylate, Mw 480) or APEG1 (polyethylene glycol methyl ether acrylate, MW 1,000). The functionalised ligands may also include polybetaines. In a preferred embodiment at least PEG2, or a PEG with a higher molecular weight is used as the functionalised ligand.

Preferably nanoreservoirs comprising nanoparticles carrying hydrophilic ligands display anti-adhesive properties against platelets and bacteria when compared to nanogel nanoparticles without hydrophilic ligands.

Preferably the hydrophilic ligands are added after the formation of the nanogel nanoparticles and are attached on the nanoparticle surface.

Accordingly, the invention provides a nanoreservoir comprising nanoparticles comprising a first polymer and a second polymer, wherein the first polymer bearing one or more catechol moieties is crosslinked to the second polymer comprising a hydrophilic backbone with one or more reactive moieties, and wherein the nanoparticles are surface decorated with hydrophilic ligands.

According to another aspect, the invention provides a nanoreservoir comprising two or more layers of nanogel. Each layer of nanogel may comprise nanoparticles as described herein. Each layer may be the same or different. For example, one layer may comprise bioactive agents. One layer may comprise nanogels loaded with different bioactive molecules. Alternatively different layers may comprise different bioactive agents. The nanoreservoir may comprise 2, 3, 4, 5 or more layers of nanoparticles of nanogel. By using multi-layered nanoreservoirs the anti-thrombotic and/or anti-biofilm properties of the nanoreservoir may be improved. The presence of multiple layers of nanogel may prolong the release of bioactive agents from within the nanoreservoir.

In a preferred embodiment, a nanoreservoir of the invention comprises at least 5 layers of nanoparticles of nanogel, wherein the nanoparticles in at least the upper most layer carry functionalised ligands. The nanoreservoir may comprise at least 2, 3, 4, 5 or more layers, wherein at least 1, 2, 3, 4 or 5 layers contain bioactive molecules, therapeutic molecules or drugs, such as an anti-bacterial and/or an anti-platelet agent, and wherein the uppermost later carries functionalised ligands. The anti-bacterial agent may be minocycline. The anti-platelet agent may be ticagrelor. The functioanlised ligand may be PEG2 or a PEG molecule with a MW of about 2000 or more.

Nanoreservoirs of the invention may have anti-bacterial and/or anti-thrombotic/anti-platelet properties conferred by bioactive agents incorporated into the nanoreservoir and/or as a result of the chemical compositions used to produce the nanoparticles.

In a further aspect of the invention the nanoreservoir of the invention may be used as a coating, for example to coat the surface of a biomaterial implant, medical device or a bioprosthesis.

In a yet further aspect, the invention provides a biomaterial implant, medical device or a bioprosthesis coated, at least on a part of its surface, with a nanoreservoir according to the invention.

A biomaterial implant may be any implantable foreign material for clinical use in host mammals such as for prosthetic joints, pacemakers, implantable cardioverter-defibrillators, catheters including intravascular or urinary catheters or materials, stents including coronary stents, mechanical and biological prosthetic heart valves, intraocular lens, dental implants and the like. In a preferred embodiment, the biomaterial implant is a bioprosthesis.

A medical device includes, but is not limited to, any device, tool, instrument, implant, or the like, relating to medicine or the practice of human or veterinary medicine, or intended for use to heal or treat a disease or condition. A medical device may include all natural and synthetic materials and both fibrous and non-fibrous materials. For example, the materials may be comprised of a metal, plastic, paper, glass, ceramic, textile, rubber, polymer, composite material or any other material or combination of materials. Exemplary medical devices include, but are not limited to, any kind of catheter; cannulae; needles; stents of any size, shape, or placement; coils of any size, shape, or placement; contact lenses; IUDs; peristaltic pump chambers; endotracheal tubes; gastroenteric feeding tubes; arteriovenous shunts; condoms; oxygenator and kidney membranes; gloves; pacemaker leads; wound dressings; metallic pins, plates and screws; metallic artificial hips; artificial knees; and gels; creams and ointments.

A bioprosthesis includes, but is not limited to, a prosthesis made of biological material. Examples include heart valves, pericardium, vascular grafts, urinary bladder prostheses, tendon prostheses, hernia patches, surgical mesh and skin substitutes. In an embodiment, the nanoreservoir of the invention may be used to coat a bioprosthetic heart valve, for example a decellularized porcine heart valve or a bovine pericardium. In another aspect the invention provides a bioprosthetic heart valve, for example a decellularized por-cine heart valve or a bovine pericardium coated with a nanoreservoir on the invention.

In an embodiment of the invention, the nanoreservoir of the present invention may be anchored or attached onto the surface of a medical device, biomaterial implant or bioprosthesis using various physical or chemical strategies, such as electrografting (electroinitiation of the polymerization by polarizing the metallic surface in the presence of the monomer), surface irradiation, layer-by-layer (LbL) assembly, spin coating, chemical vapor deposition (CVD), laser deposition, blood proteins, mussel-inspired coatings, and plant phenols (Qiang Wei and Rainer Haag., 2005, *Mater. Horiz.* 2015, 2: 567-577 Universal polymer coatings and their representative biomedical applications).

According to another aspect of the invention, there is provided a nanoreservoir formed by cross-linking a first polymer and a second polymer, wherein the first polymer bears one or more catechol moieties; and the second polymer comprises a hydrophilic backbone with one or more reactive moieties. The polymers may be crosslinked in the presence of one or more bioactive agents so as to produce nanoparticles comprising the first and second polymers with the bioactive agent entrapped within.

In a yet further aspect, there is provided a method of forming a nanoreservoir comprising crosslinking a first polymer which bears one or more catechol moieties with a second polymer comprising a hydrophilic backbone with one or more reactive moieties. The nanoreservoir produced preferably comprises nanoparticles of crosslinked polymers.

In a preferred embodiment, the method of making a nanoreservoir comprises the steps of:
i) obtaining P(mDOPA)

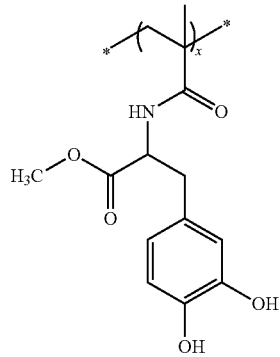

ii) oxidising P(mDOPA) to form an aqueous solution of Pox(mDOPA):

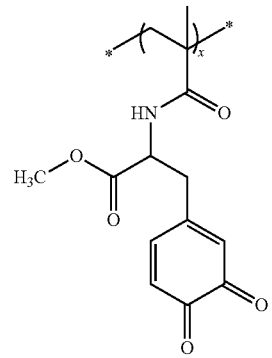

iii) adding a PAH solution to the aqueous solution of Pox(mDOPA)

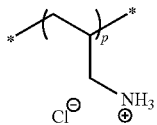

iv) crosslinking the compounds of ii) and iii) to from a nanogel solution of nanoparticles of the formula:

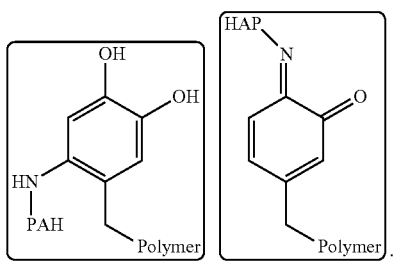

In a preferred embodiment, the invention provides a method of making a nanoreservoir comprising at least two bioactive molecules, therapeutic molecules or drugs, the method comprising the steps of:
  i) mixing Pox(mDOPA) in an aqueous solution with one bioactive molecule, therapeutic molecule or drug:
  ii) adding a PAH solution to the resulting aqueous solution of Pox(mDOPA) obtained in i) to form a first nanogel solution;
  iii) repeating steps i) and ii) with a second bioactive molecule, therapeutic molecule or drug to form a second nanogel solution;
  iv) mixing the first and second nanogel solutions to obtain a nanoreservoir with two bioactive molecules, therapeutic molecules or drugs.

The nanoreservoir may comprise a ratio of nanogels loaded with a first bioactive molecule, therapeutic molecule or drug to nanogels loaded with a second bioactive molecule, therapeutic molecule or drug of between about 1 part first and about 5 parts second bioactive molecule, therapeutic molecule or drug; or about 2 parts first and about 3 parts second bioactive molecule, therapeutic molecule or drug.

The first bioactive molecule, therapeutic molecule or drug may be an antibiotic. The second bioactive molecule, therapeutic molecule or drug may be an anti-platelet agent.

According to another aspect the invention provides a method of producing a medical device, a biomaterial implant or a bioprosthesis with a coated surface comprising coating a surface of the medical device, biomaterial implant or bioprosthesis with a nanoreservoir according to the invention.

The method may comprise the steps of
  i) dippping the surface to be coated in a solution of a first polymer;
  ii) oxidising the first polymer;
  iii) dipping the resulting surface in a second polymer solution;
  iv) dipping the surface in a solution of a nanoreservoir as described herein to produce a coating on the surface; and
  v) optionally dipping the coated surface in a solution of hydrophilic functionalized ligand.

The first polymer may be P(mDOPA). The oxidised form of the first polymer may be Pox(mDOPA). The second polymer may be PAH.

The nanoreservoir in step iv) may comprises nanoparticles of a nanogel formed by crosslinking a first polymer and a second polymer. The first polymer may be P(mDOPA) and the second polymer may be PAH.

The nanoreservoir in step iv) may comprise one or more, preferably two or more bioactive molecules, therapeutic molecules and/or drugs. The bioactive molecules may include an antibiotic and/or an anti-platelet agent.

A medical device, a biomaterial implant or a bioprosthesis with a surface coated with a nanoreservoir comprising two or more layers of nanoparticles may be produced by repeating steps iii) and iv) of the above described method. A nanoreservoir comprising 2, 3, 4, 5 or more layers may be produced.

The bioprosthesis may a prosthetic heart valve.

The method of the invention may be used to coat just a part of the surface of a medical device, a biomaterial implant or a bioprosthesis, or substantially the whole or the whole surface of a medical device, a biomaterial implant or a bioprosthesis.

The invention further provides a coated medical device, a biomaterial implant or a bioprosthesis according to the invention or produced by the method of the invention for use in the prevention or reduction of infection when the medical device, a biomaterial implant or a bioprosthesis is implanted in a subject.

The invention further provides a nanoreservoir according to the invention or produced by the method of the invention for use in the prevention or reduction of infection when a medical device, a biomaterial implant or a bioprosthesis is implanted in a subject. The subject may be a mammal, preferably a human.

According to another aspect of the invention, there is provide a method of coating a surface of a medical device, a biomaterial implant or a bioprosthesis with a nanoreservoir, the method comprising the steps of
  i) dipping the surface to be coated in a solution of P(mDOPA);
  ii) oxidising the P(mDOPA) to form Pox(mDOPA);
  iii) dipping the resulting surface in a PAH solution;
  iv) dipping the surface in a solution of a nanoreservoir according to the invention; and
  v) optionally dipping the resulting coated surface in a solution of hydrophilic functionalized ligand.

According to another aspect of the invention, there is provide a method of coating a surface of a medical device, a biomaterial implant or a bioprosthesis with a nanoreservoir comprising two or more different bioactive molecules, therapeutic molecules or drugs, wherein the method comprises the steps of
  i) dipping the surface in a solution of p(mDOPA);
  ii) oxidising the p(mDOPA) to form Pox(mDOPA);
  iii) dipping the resulting surface in a PAH solution;
  iv) dipping the surface in a solution of nanoreservoirs according to the invention containing two or more bioactive molecules, therapeutic molecules or drugs;
  v) repeating steps iii) and iv) at least 3, 4 or 5 times to build a multilayer coating; and optionally
  vi) dipping the coated surface in a solution of hydrophilic functionalized ligand According to a further aspect, there is provided a biomaterial implant, a medical device or a bioprosthesis, such as a prosthetic heart valve, coated at least in part with a nanoreservoir comprising at least 2, 3, 4, 5, 6 or more layers according to the invention. At least one of the layers of the nanoreservoir preferably comprises at least least 2 bioactive molecules, therapeutic molecules or drugs. Preferably the outermost layer of the nanoreservoir carries functionalised groups according to the invention.

According to a further aspect of the invention, there is provided a nanoreservoir formed by cross-linking a first polymer and a second polymer, the first polymer bearing one or more catechol moieties; and the second polymer comprising a hydrophilic backbone with one or more reactive moieties; for use as a coating on a biomaterial implant, medical device or bioprosthesis; optionally wherein the nanoreservoir contains one or more bioactive molecule, therapeutic molecule or drug.

According to another aspect of the invention, there is provided a nanoreservoir comprising a nanogel comprising at least polymers of Formula I:

Formula I

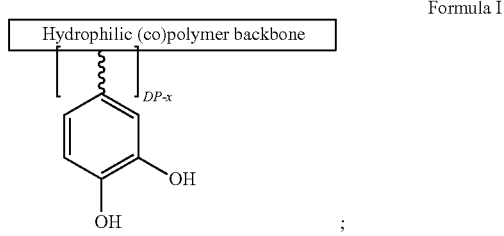

with DP = polymerization degree of the main chain
and x = can be 1 to DP-1 wherein the hydrophilic polymer backbone comprises one or more of polyallylamine, polyvinylamines, polyvinylamides, polyvinylalcohol, poly(metha)acrylates, poly(meth)acrylamide, polyurethane or PEG or a polyelectrolyte (cationic, anionic or zwitterionic) or a hydrophilic biopolymer such as a polysaccharide such as chitosan or hyaluronan.

According to a further aspect of the invention, there is provided a nanoreservoir comprising a nanogel formed by cross-linking polymers of Formula I:

Formula I

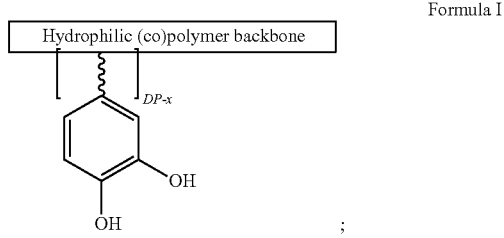

with DP = polymerization degree of the main chain
and x = can be 1 to DP-1 wherein the hydrophilic polymer backbone comprises one or more of polyallylamine, polyvinylamines, polyvinylamides, polyvinylalcohol, poly(metha)acrylates, poly(meth)acrylamide, polyurethane or PEG or a polyelectrolyte (cationic, anionic or zwitterionic) or a hydrophilic biopolymer such as a polysaccharide such as chitosan or hyaluronan.

In a further aspect of the invention, the nanoreservoir according to the invention may be used in a coating composition on a medical device, a biomaterial implant or a bioprosthesis.

In a further aspect of the invention, there is provided the use of a nanoreservoir according to the invention as a coating on a medical device, a biomaterial implant or a bioprosthesis.

In a further aspect of the invention, there is provided the use of a nanoreservoir according to the invention as a coating composition on a medical device, a biomaterial implant or a bioprosthesis.

In another aspect of the invention, the nanoreservoir may be used in a coating composition on a medical device, a biomaterial implant or bioprosthesis, wherein the nanoreservoir comprises one or more bioactive compounds or drugs.

In a further aspect, the invention provides a medical device, a biomaterial implant or a bioprosthesis with nanoreservoirs of the invention on the surface. The surface of the medical device, biomaterial implant or bioprosthesis may be coated with a nanoreservoir of the invention.

A biomaterial implant, medical device or bioprosthesis, or part thereof, may be coated with a nanoreservoir of the invention by dipping the biomaterial implant, medical device or bioprosthesis into a solution comprising nanoreservoirs of the invention, or by spraying the biomaterial implant, medical device or bioprosthesis with a solution comprising nanoreservoirs of the invention and then drying the coated biomaterial implant, medical device or bioprosthesis.

In the present invention, the nanoreservoir may be configured to be anti-adhesive against both platelets and bacteria, and for storing and/or delivering therapeutic and/or active molecules such as biological and non-biological active molecules (e.g. drugs, biologics) with or without an associated coating that controls the rate of delivery of the therapeutic or active molecule to the surrounding tissue. The rate of delivery may be for a period of release of at least 1 day, 2 days, 3 days, 7 days, whilst the anti-adhesive efficacy will be maintained for at least one month, at least two months, at least 3 months, at least 4 months, at least 5 months, or at least 6 months.

In a preferred embodiment, the nanoresevoir contains an antibiotic and an anti-platelet agent. In a further preferred embodiment, the nanoreservoir contains minocycline and ticagrelor. In a preferred embodiment, the nanoresevoir contains an anti-biofilm formation agent and an anti-coagulant. In a preferred embodiment, the nanoresevoir contains an anti-biofilm formation agent and an anti-platelet agent.

According to another aspect of the invention, there is provided a method of making a nanoreservoir comprising the steps of:
(i) mixing in an aqueous solution a quinone functionalized polymer in the presence of one or more bioactive molecules or drugs;
(ii) adding a polymer solution to the aqueous solution to form a nanogel solution wherein the polymer is selected from one or more of polyallylamine, polyvinylamines, polyvinylamides, polyvinylalcohol, poly(metha)acrylates, poly(meth)acrylamide, polyurethane or PEG or a polyelectrolyte (cationic, anionic or zwitterionic) or a hydrophilic biopolymer such as a polysaccharide such as chitosan or hyaluronan.

According to another aspect of the invention, there is provided a method of making a nanoreservoir comprising the steps of:
(i) mixing a quinone functionalized polymer Pox (mDOPA) in an aqueous solution with the one or more bioactive molecule, therapeutic molecule or drug;
(ii) adding a PAH solution to the aqueous solution of Pox(mDOPA) to form a nanogel solution.

In a preferred embodiment of the invention, there is an initial step of oxidising p(mDOPA) to form the Pox (mDOPA).

In further embodiment of the invention, there is an additional step of lyophilising the nanogel solution.

In a preferred embodiment of the invention, the aqueous solution of Pox(mDOPA) and/or the PAH solution has a pH of at least 8, preferably at least 10.

The invention also provides a method of making a nanogel, comprising the steps of:
(i) dissolving the first polymer, e.g. methacrylamide bearing 3,4-dihydroxy-L-phenylalanine (P(mDOPA)) in distilled water to produce oxidized P(mDOPA),
(ii) adding NaOH (0.1M) to the aqueous solution of oxidized P(mDOPA) at room temperature;
(ii) adding a solution of PAH at about pH 10 to the aqueous solution of oxidized P(mDOPA) under vigorous stirring for at least an 1 hour at room temperature.

Preferably in step (ii) the NaOH and oxidized P(mDOPA) are mixed for at least 6 hours, preferably overnight. Preferably the pH of the solution is 10 or above.

According to a further aspect of the invention, there is provided a method of making a nanogel, comprising the steps of:
(i) dissolving methacrylamide bearing 3,4-dihydroxy-L-phenylalanine (P(mDOPA)) in distilled water in the presence of a bioactive molecule or drug to produce oxidized P(mDOPA) for 1 hour at 6° C.,
(ii) adding NaOH (0.1M) to the aqueous solution of oxidized P(mDOPA) at room temperature overnight;
(ii) adding a solution of PAH at pH 10 to the aqueous solution of oxidized P(mDOPA) under vigorous stirring overnight at 6° C.

According to another aspect of the invention, there is provided a nanogel obtained by any method of the invention.

It will be appreciated that optional features applicable to one aspect or embodiment of the invention can be used in any combination, and in any number. Moreover, they can also be used with any of the other aspects or embodiments of the invention in any combination and in any number. This includes, but is not limited to, the dependent claims from any claim being used as dependent claims for any other claims of this application.

The invention will be further described, by means of non-limiting example only, with reference to the following figures and experimental examples.

FIG. 1—shows the chemical structures of (1) P(mDOPA), (2) Pox(mDOPA) (3) PAH

Figure 2:
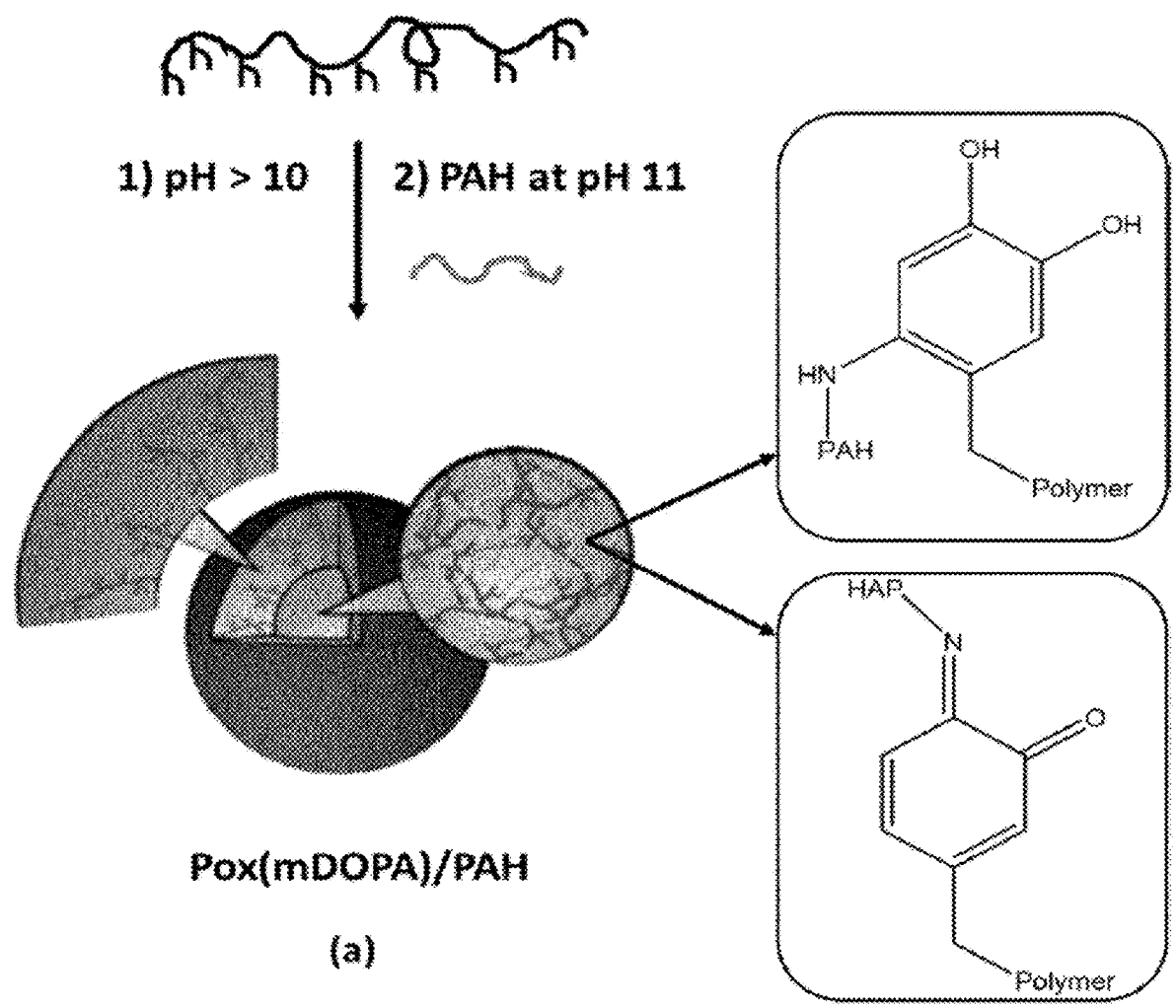

FIG. 2—shows the strategy for the formation of nanogels of Pox(mDOPA)/PAH.

Figure 3:
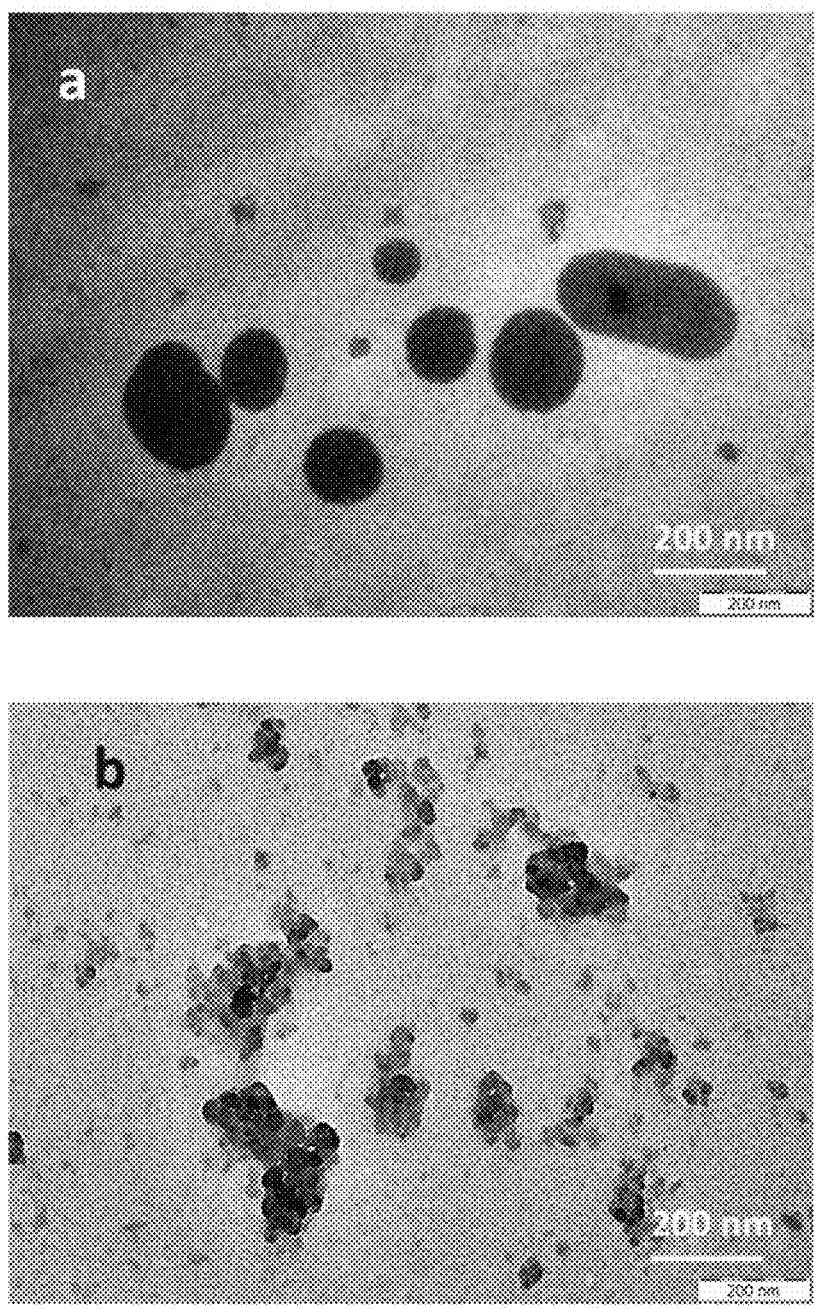

FIG. 3—shows TEM analysis of a nanogel according to the invention without (a) and with lyophilisation (b).

Figure 4:
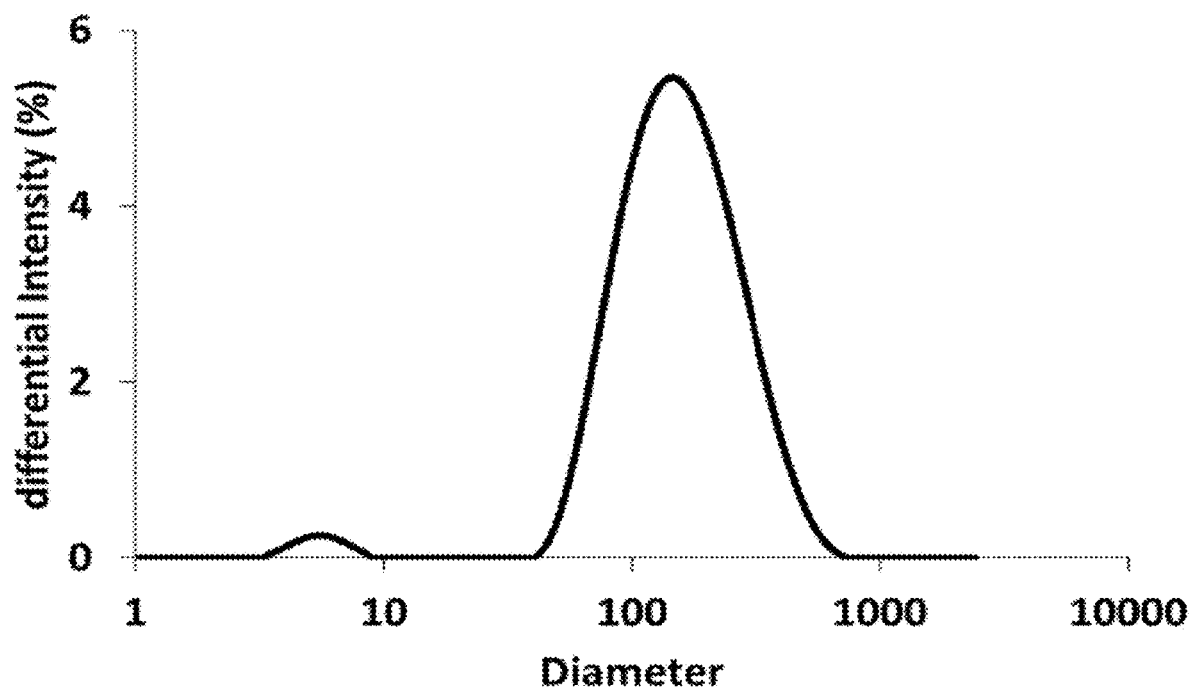

FIG. 4—shows DLS analysis of nanogel solution.

Figure 5:
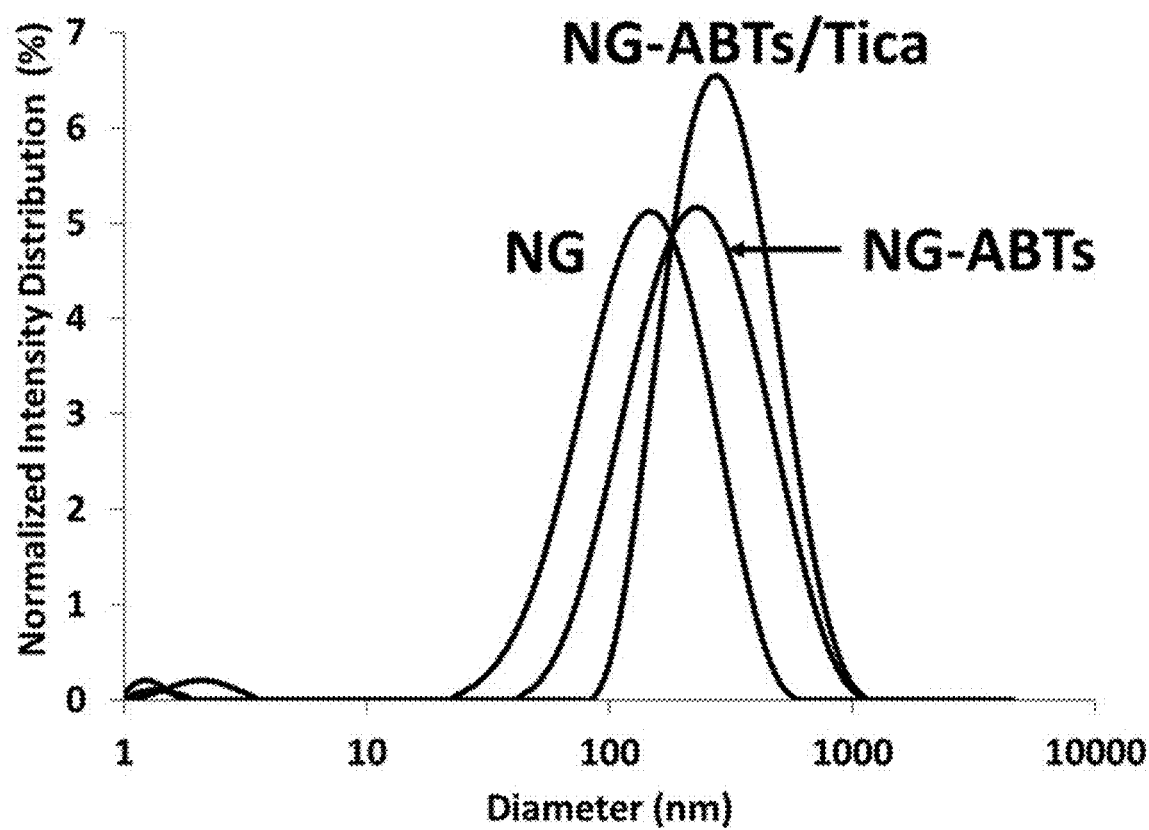

FIG. 5—shows DLS analysis of nanogel, nanogel (ABTs) and nanogel (ABTs-Tica).

Figure 6:
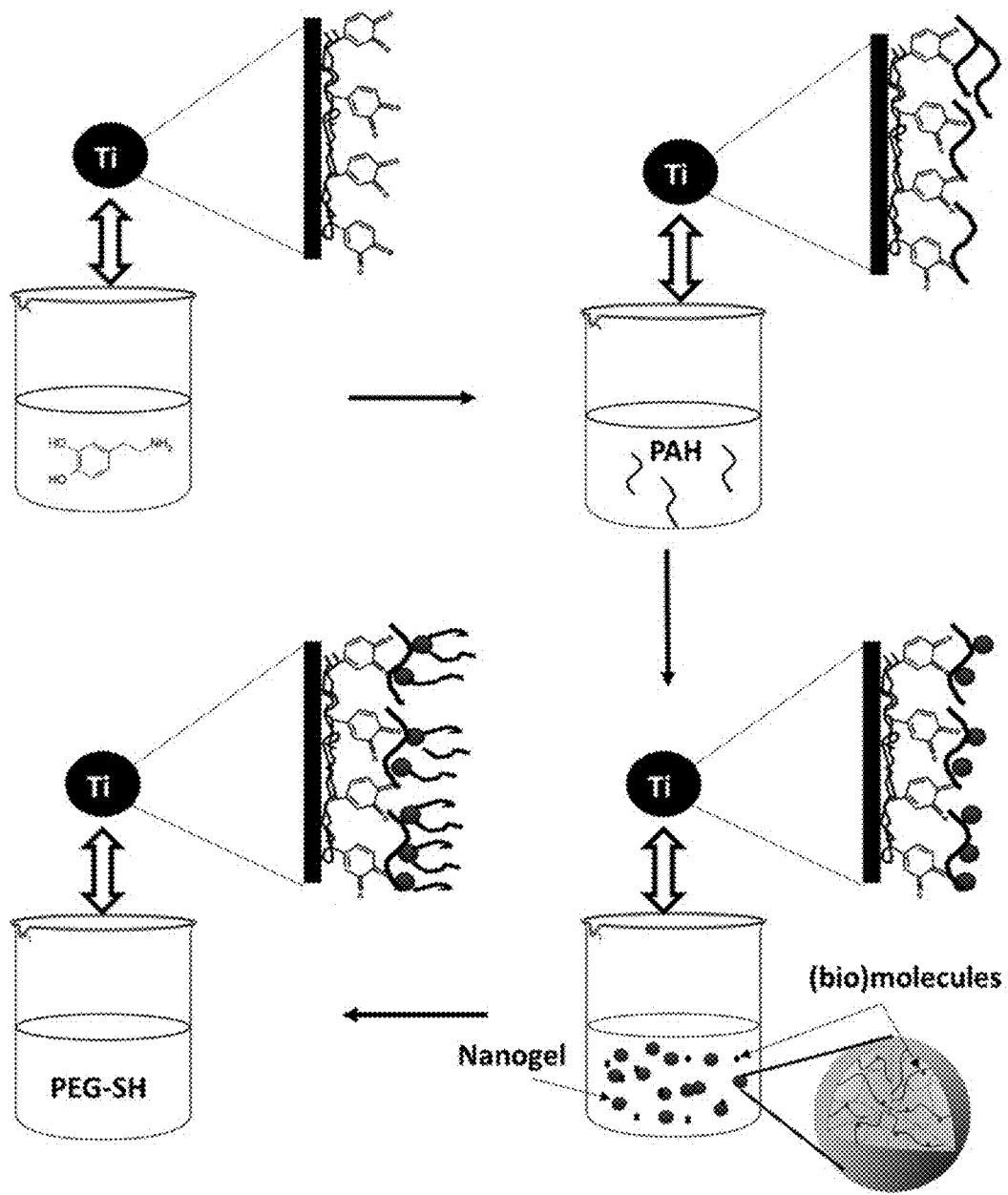

FIG. 6—shows the modification of Ti surfaces with polydopamine (PDOPA) layers, PAH and nanogels are self-crosslinked through Schiff-base bond on PDOPA coated Ti substrates.

Figure 7:
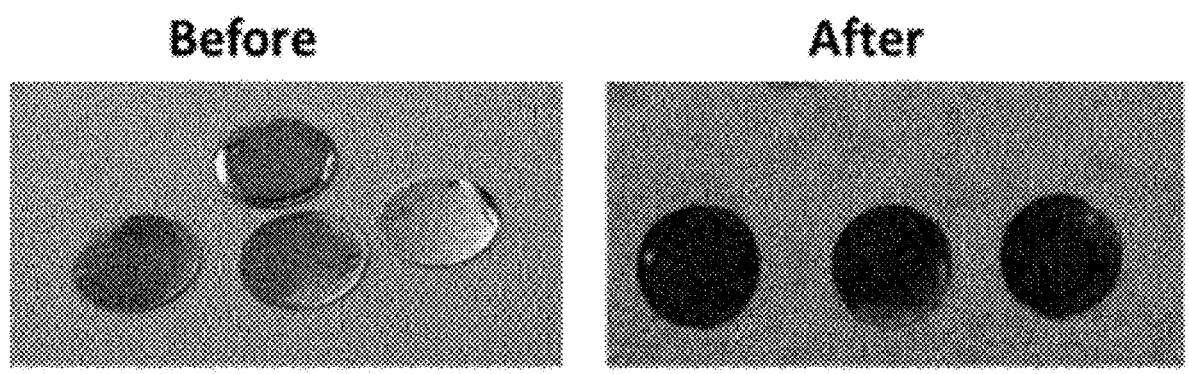

FIG. 7—shows an image of a Ti surface before and after PDOPA modification.

Figure 8:
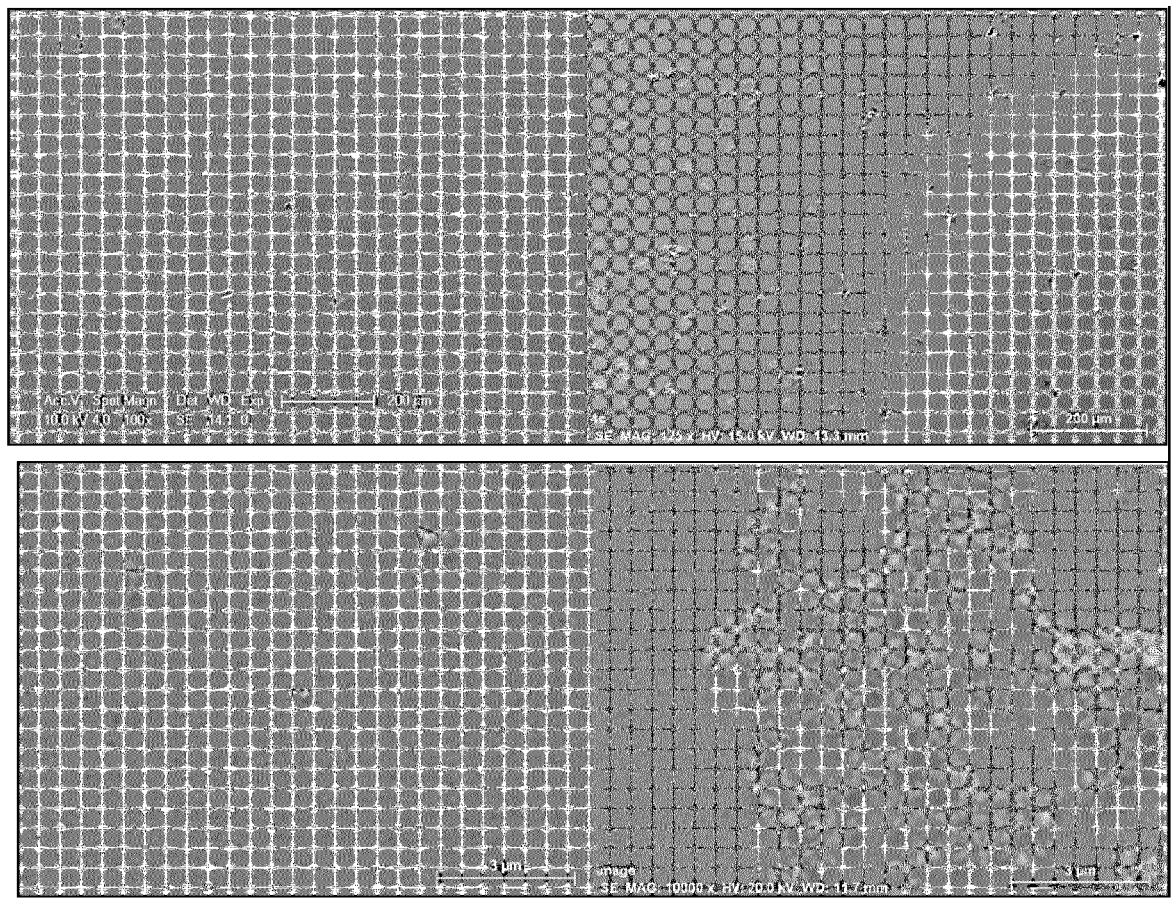

FIG. 8—shows field emission scanning electron microscopy (SEM) observations.

Figure 9:
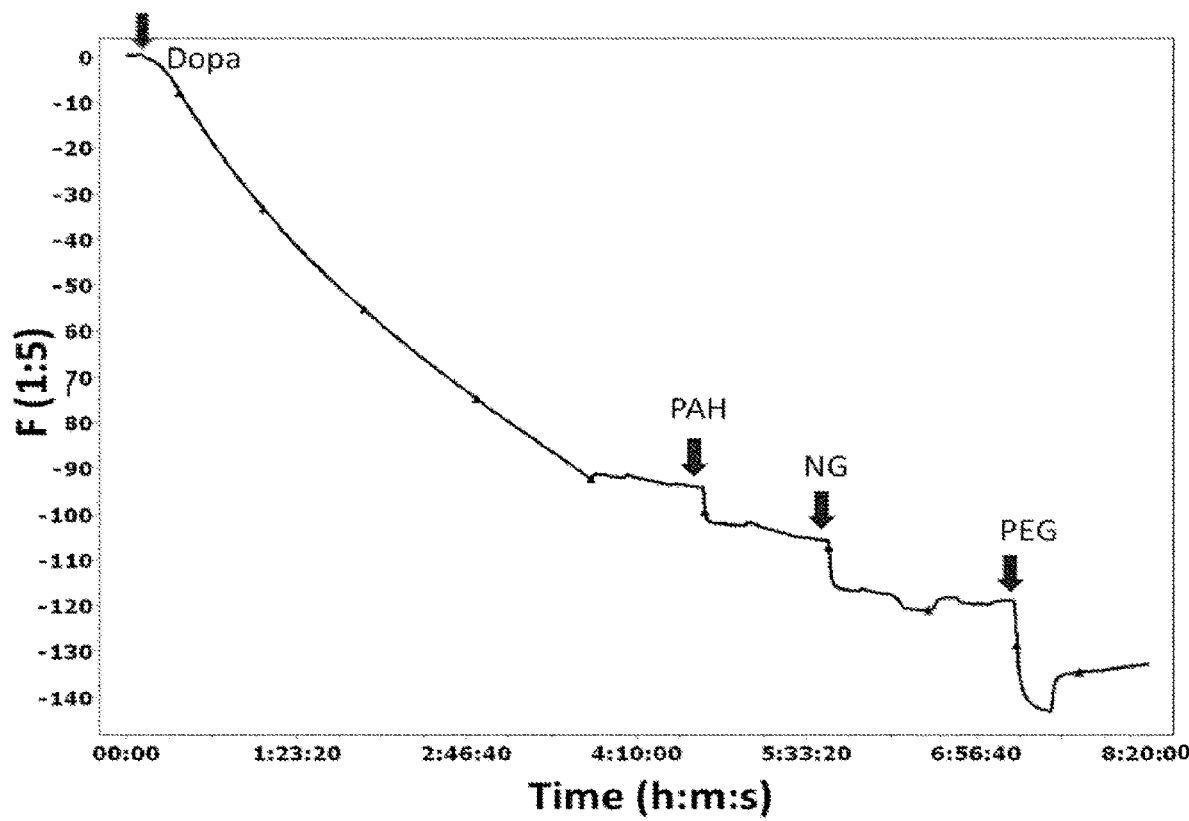

FIG. 9—shows nanoreservoir build-up analyzed by Quartz Crystal Microbalance.

Figure 10:
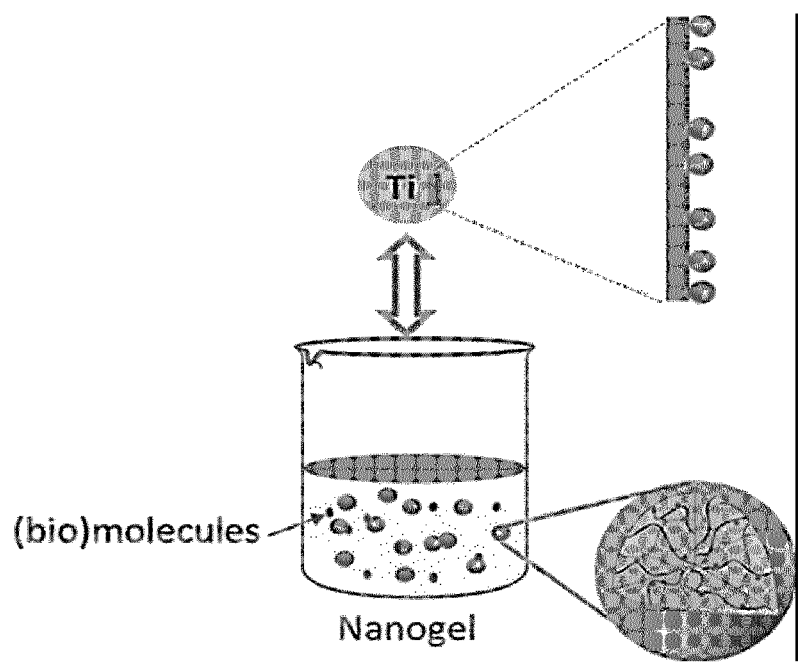

FIG. 10—shows the modification of a Ti surface with nanogels according to the invention.

Figure 11:
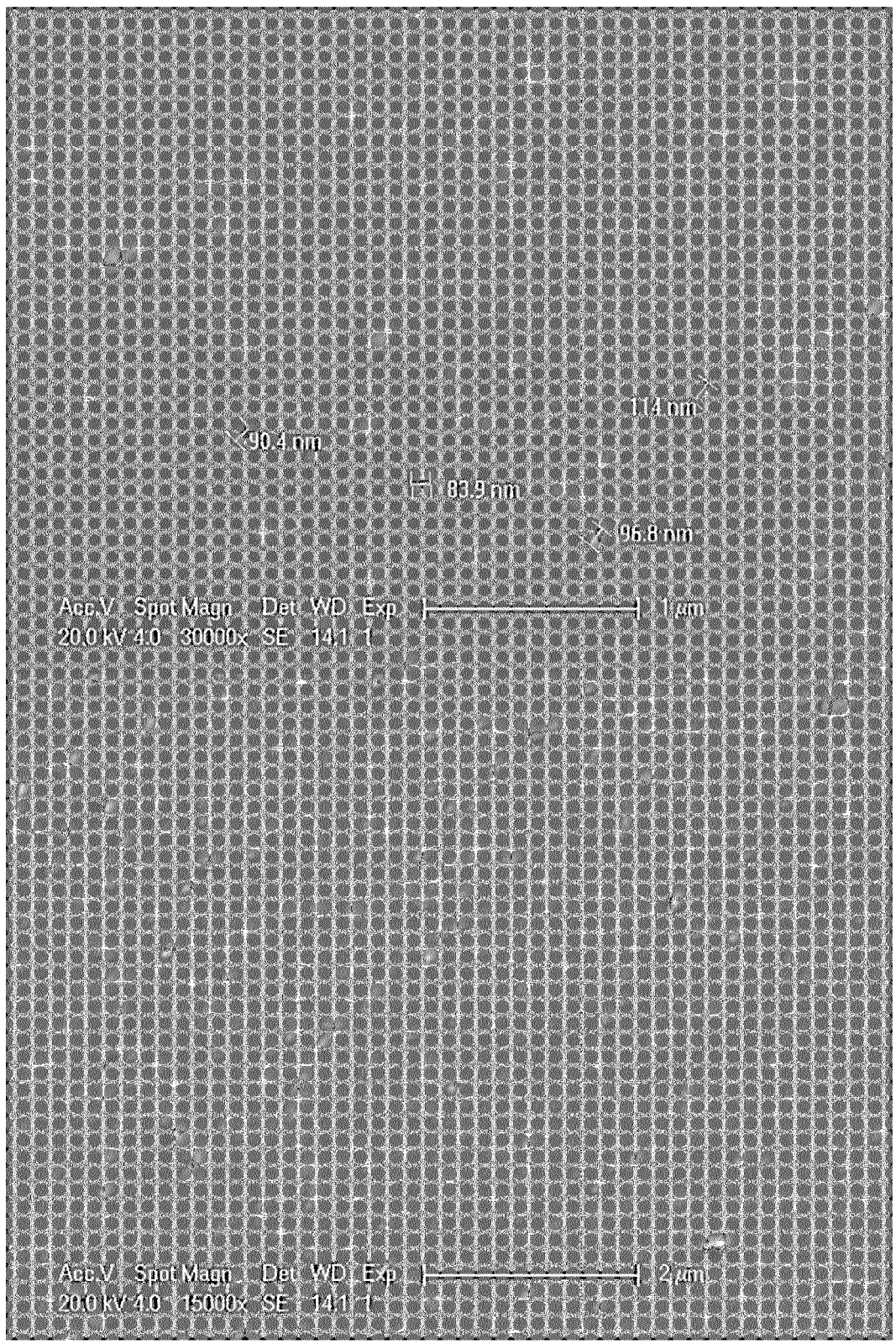
Figure 12:
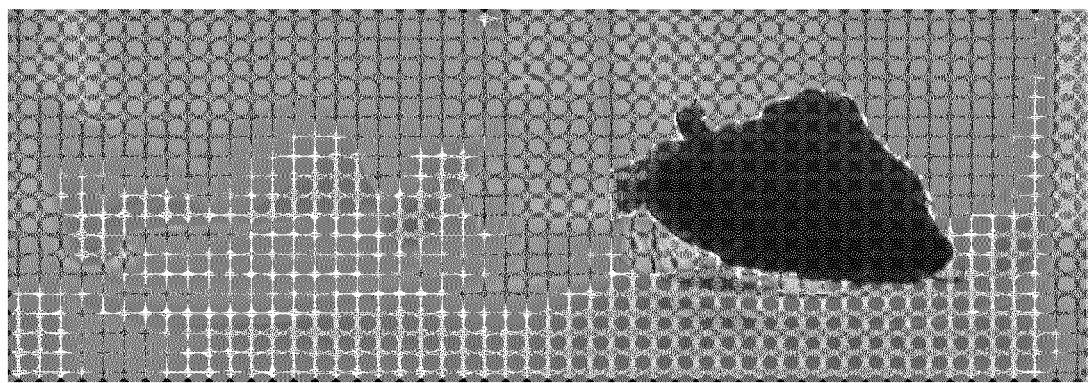

FIG. 11—shows SEM analysis of a nanogel according to the invention deposited on a Ti surface following the $2^{nd}$ approach FIG. 12—shows pictures of a biological valve before and after PDOPA modification.

Figure 13:
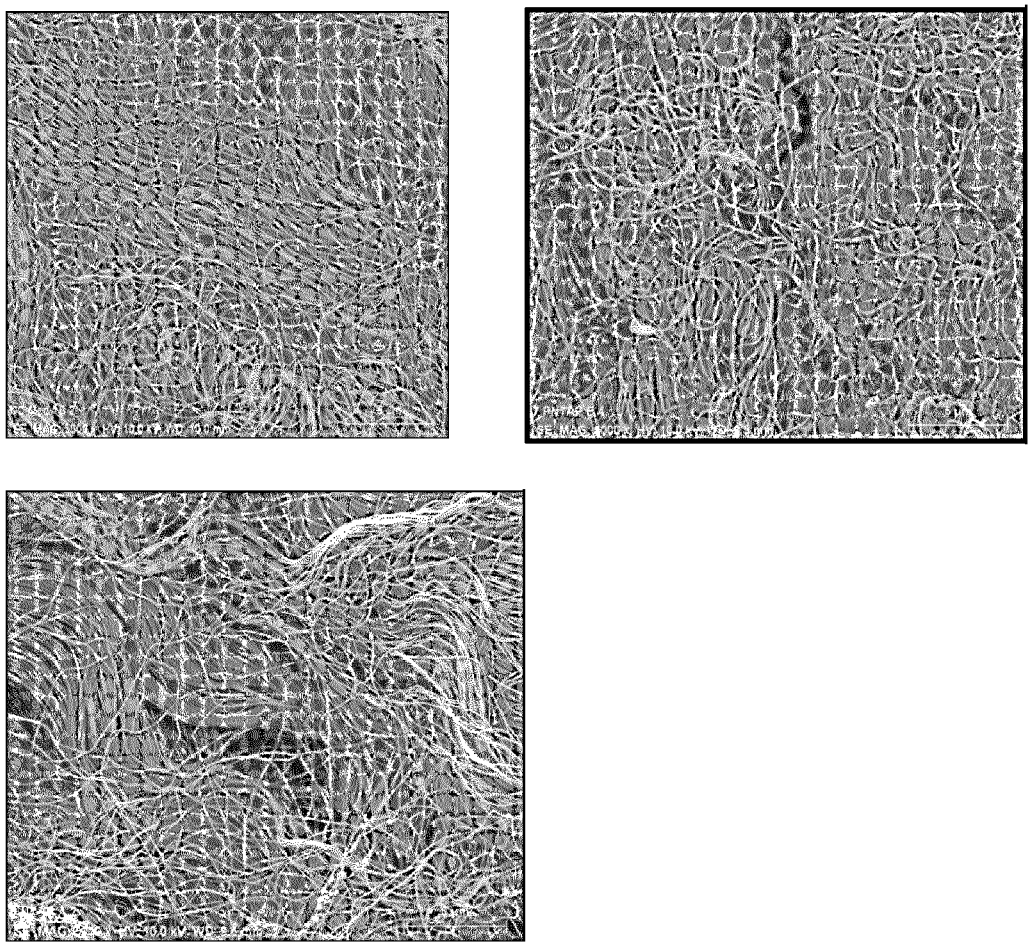

FIG. 13—shows SEM images of a biological valve surface before (above left) and after nanogel deposition with (above right) or without PDOPA coating (bottom left) (magnification=5000×).

Figure 14:
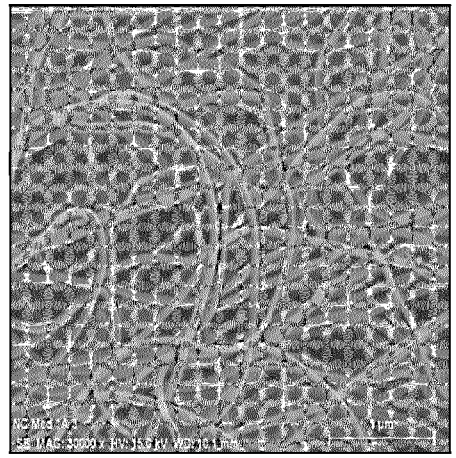
Figure 14:
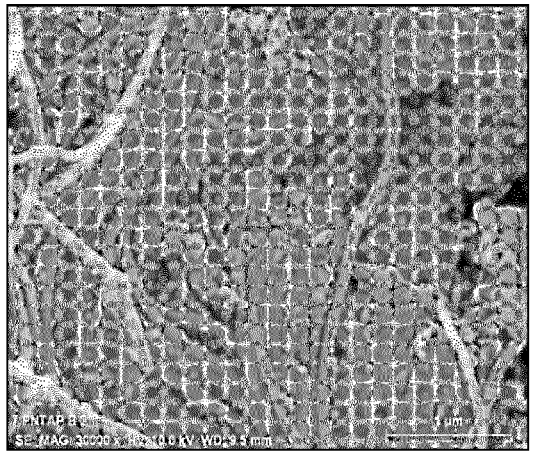
Figure 14:
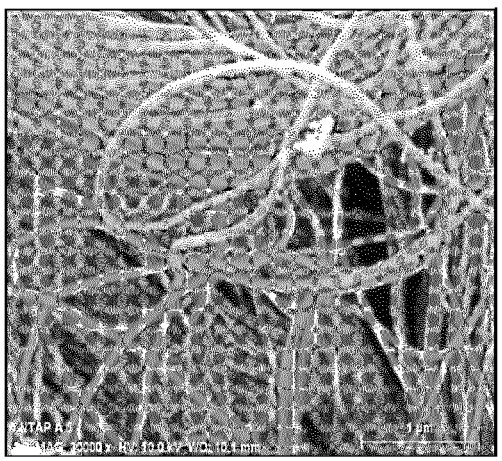

FIG. 14—shows SEM images of a biological valve surface before (above left) and after nanogel deposition with (above right) or without PDOPA coating (bottom left) (magnification=30000×).

Figure 15:
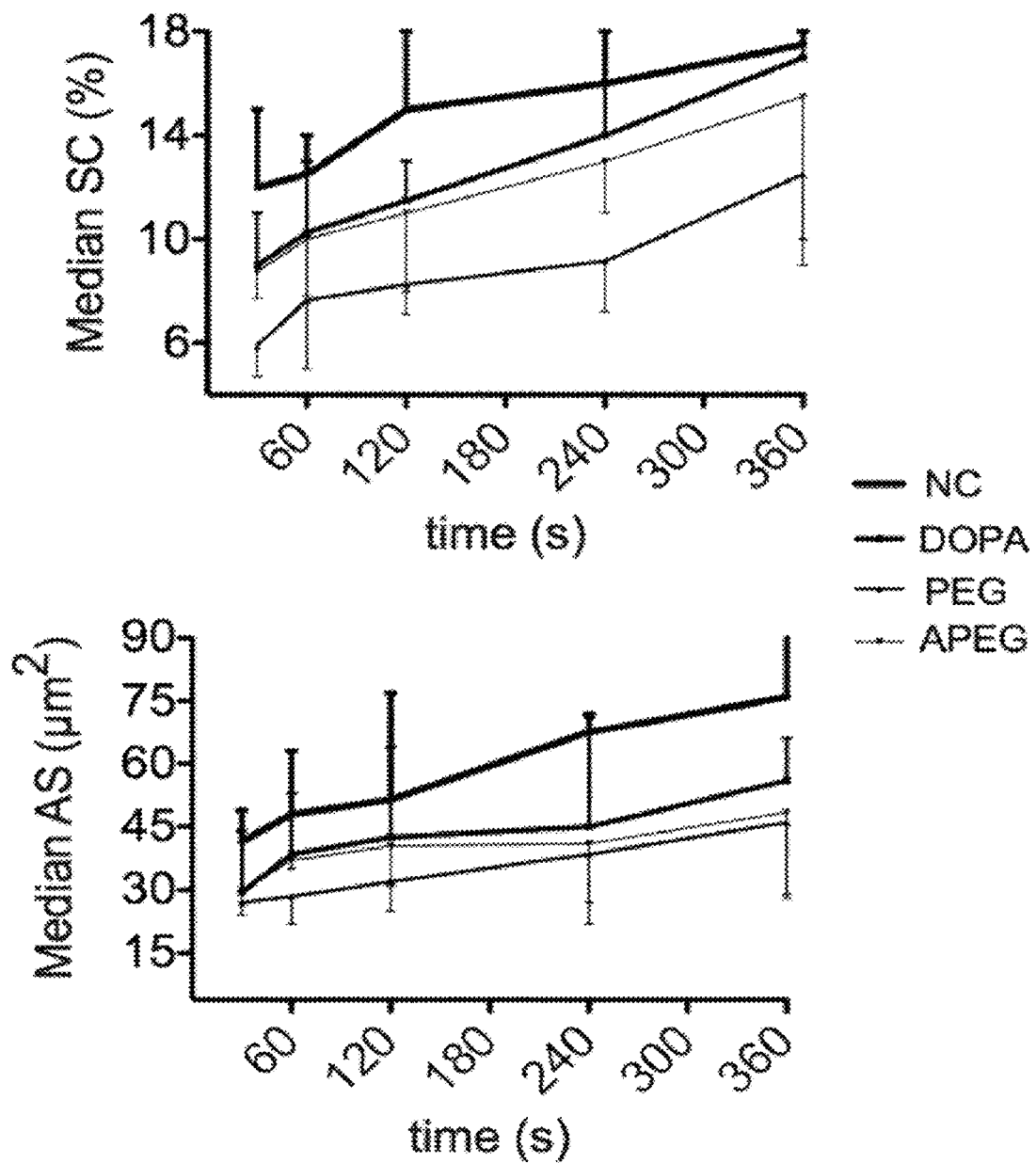

FIG. 15—shows a dynamic hemocompatibility test using an Impact-R system at a constant shear rate of $1800\ s^{-1}$ for 2 min. The effect of shear stress on platelets adherence (left graph) and aggregate formation (right graph) at different time points with two polymer coatings PEG or APEG is shown. Median values on N=4 healthy donors are reported in both graphs. Statistical analysis was performed using Graph Pad software with grouped, two-way ANOVA and Bonferroni post-test. Moreover, platelets adherence correlated with water contact angles of coatings on glass support: surfaces with lower contact angle (i.e. the more hydrophilic PEG surface) gave lower platelets adherence.

Figure 16:
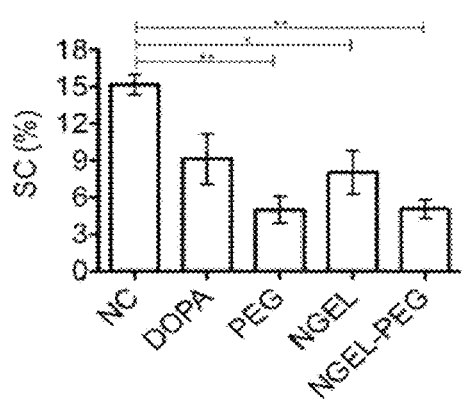
Figure 16:
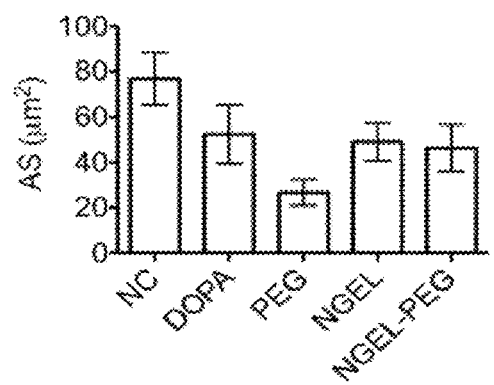
Figure 16:
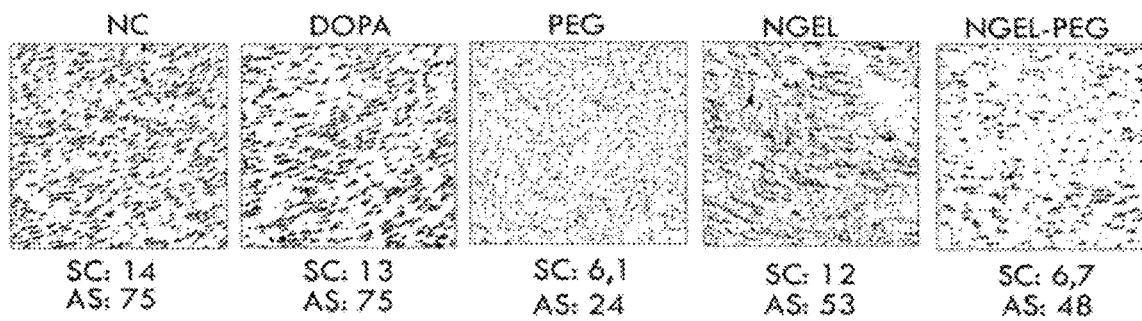

FIG. 16—shows a dynamic Impact-R test at a constant shear rate of $1800\ s^{-1}$ for 2 min (A and B). A SC and B AS median values determined on 3 healthy donors (duplicates per condition per donor). C. Representative pictures of the test shown in A and B.

Figure 17:
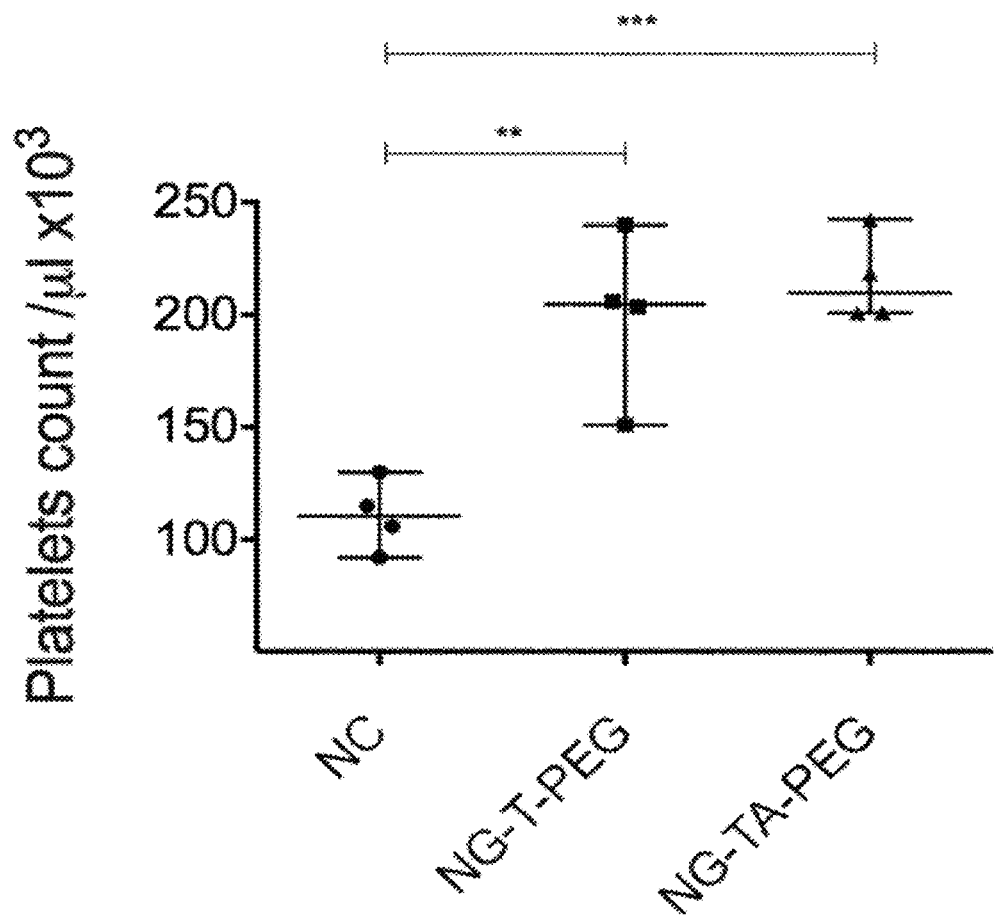

FIG. 17—shows a dynamic Impact-R test at a constant shear rate of $1800\ s^{-1}$ for 4 min. Platelet count was measured after shear stress challenge. Test was carried on one donor in quadruplicate.

Figure 18:
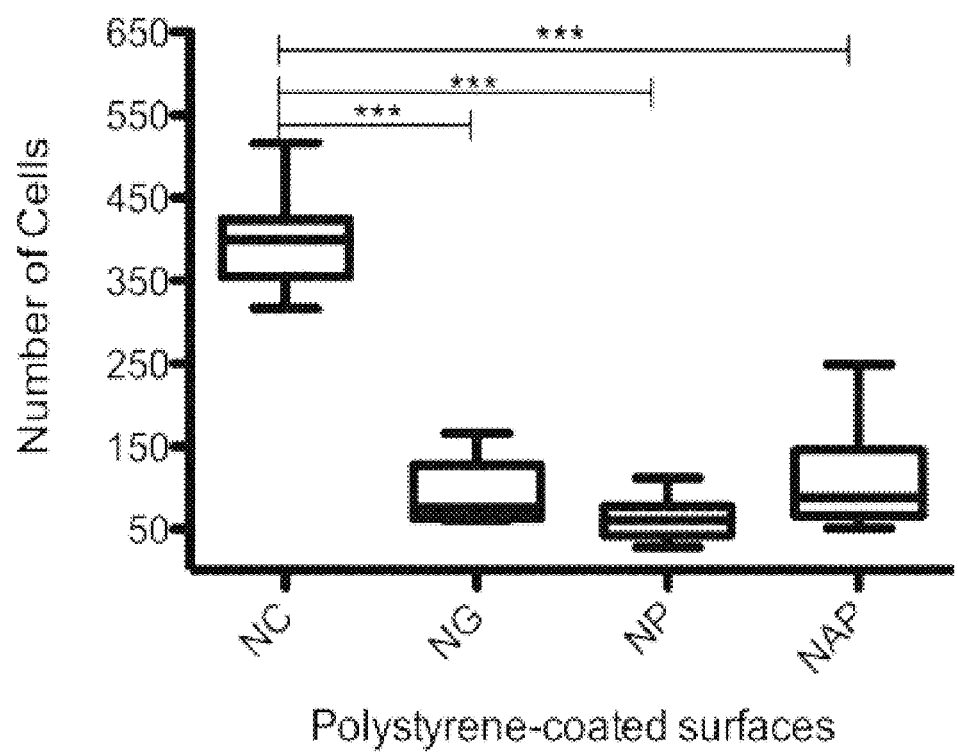

FIG. 18—shows a static test which analyses blood cells that have adhered to nanogel-modified surfaces. Blood was incubated on 24-well polystyrene non-coated (NC) or coated with Nanogel (NG) or Nanogel Peg (NP) or Nanogel Antibiotics Peg (NAP). Cells that adhered to the surface were stained with crystal violet. Images of cells fixed on the polystyrene surface were processed. Images were taken with an optical microscope Olympus CKX41 (20× magnification). Number of cells counted in each field using Fiji Software (Particle Analysis plug-in). Numbers represent average of 8 fields per conditions.

Figure 19:
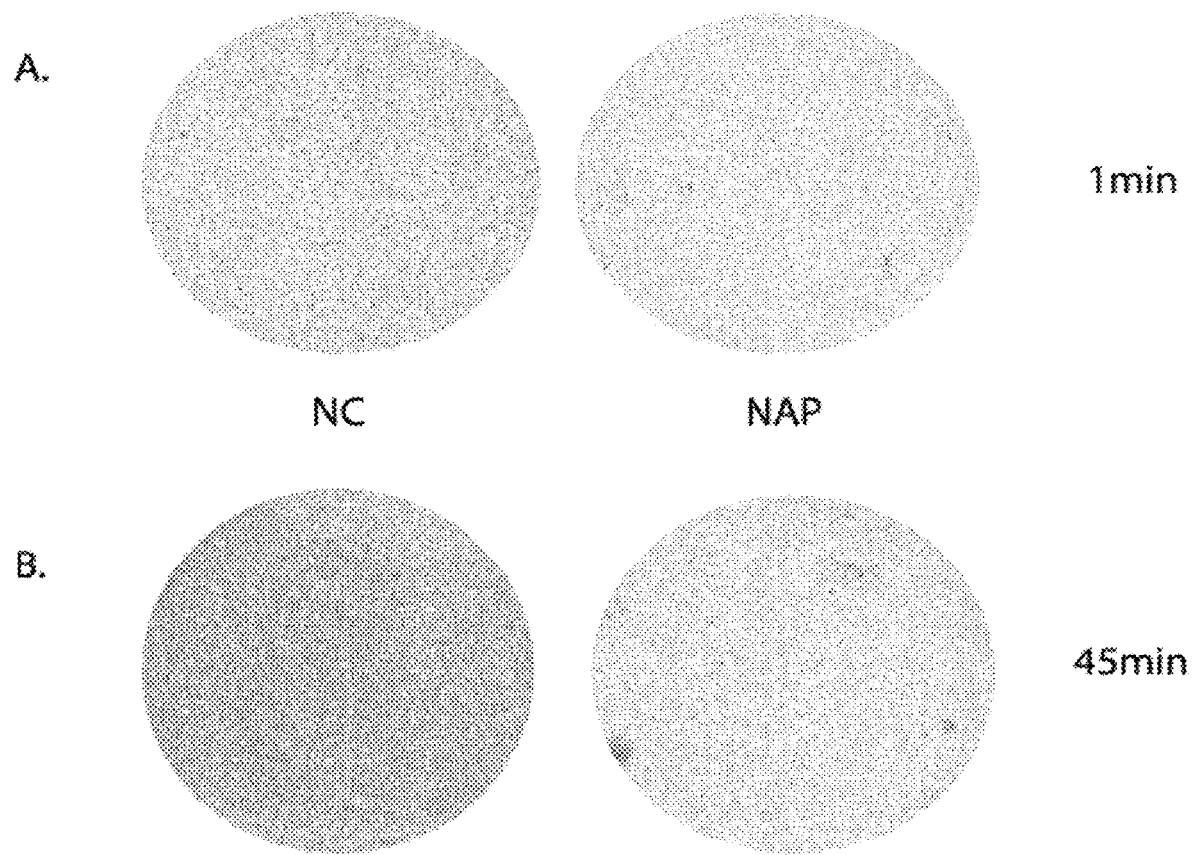

FIG. 19—shows platelets rich plasma (PRP) at a concentration of 250000 platelets/µl incubated in static condition at 37° C. for 1 min (A) or 45 min (B) on PS NC (polystyrene non-coated) or NAP (nanogel antibiotic PEG)-coated wells. After 3 washes with NaCl 0.9% platelets were stained with May-Grünwald solution and were observed at an Olympus CKX41 optical microscope (10× magnification).

Figure 20:
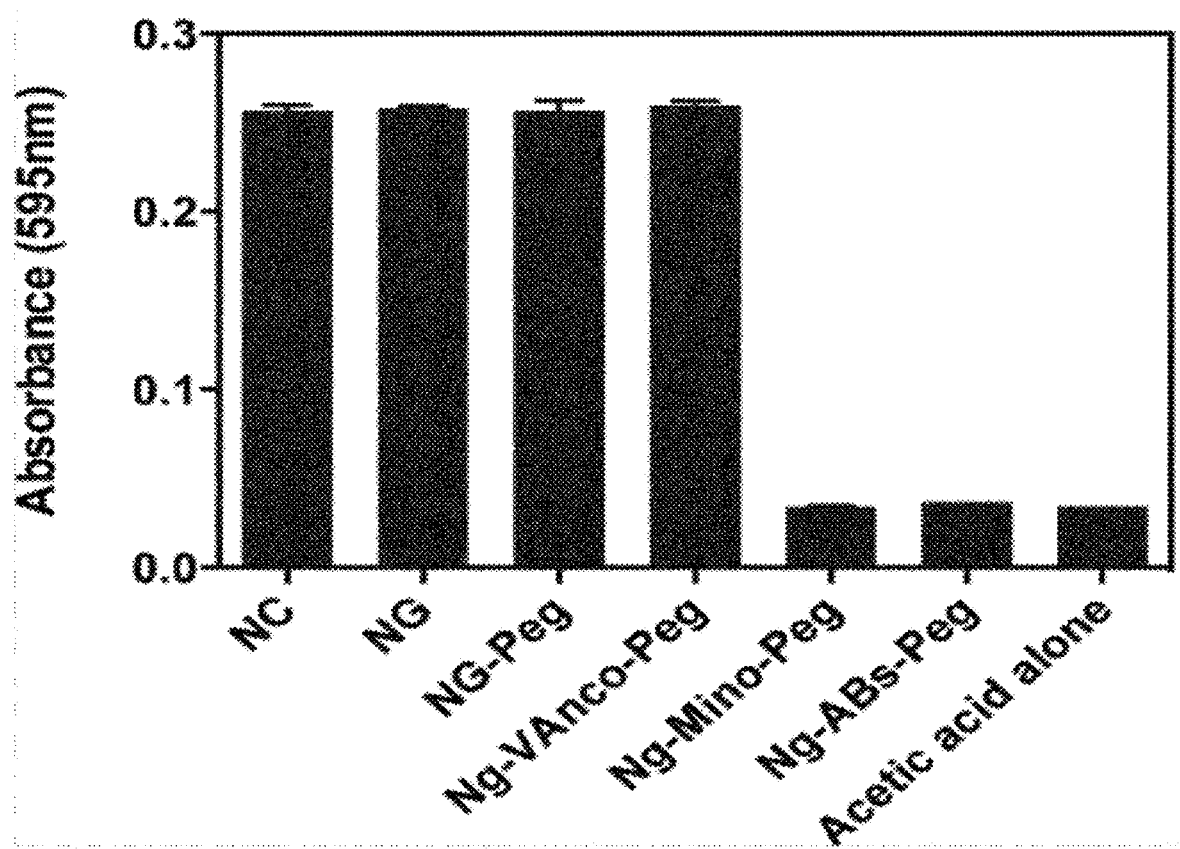

FIG. 20—shows S. aureus biofilm quantification with crystal violet. Bacteria were grown for 24 hours on a polystyrene surface modified by nanogels loaded or not with antibiotics as indicated.

Figure 21:
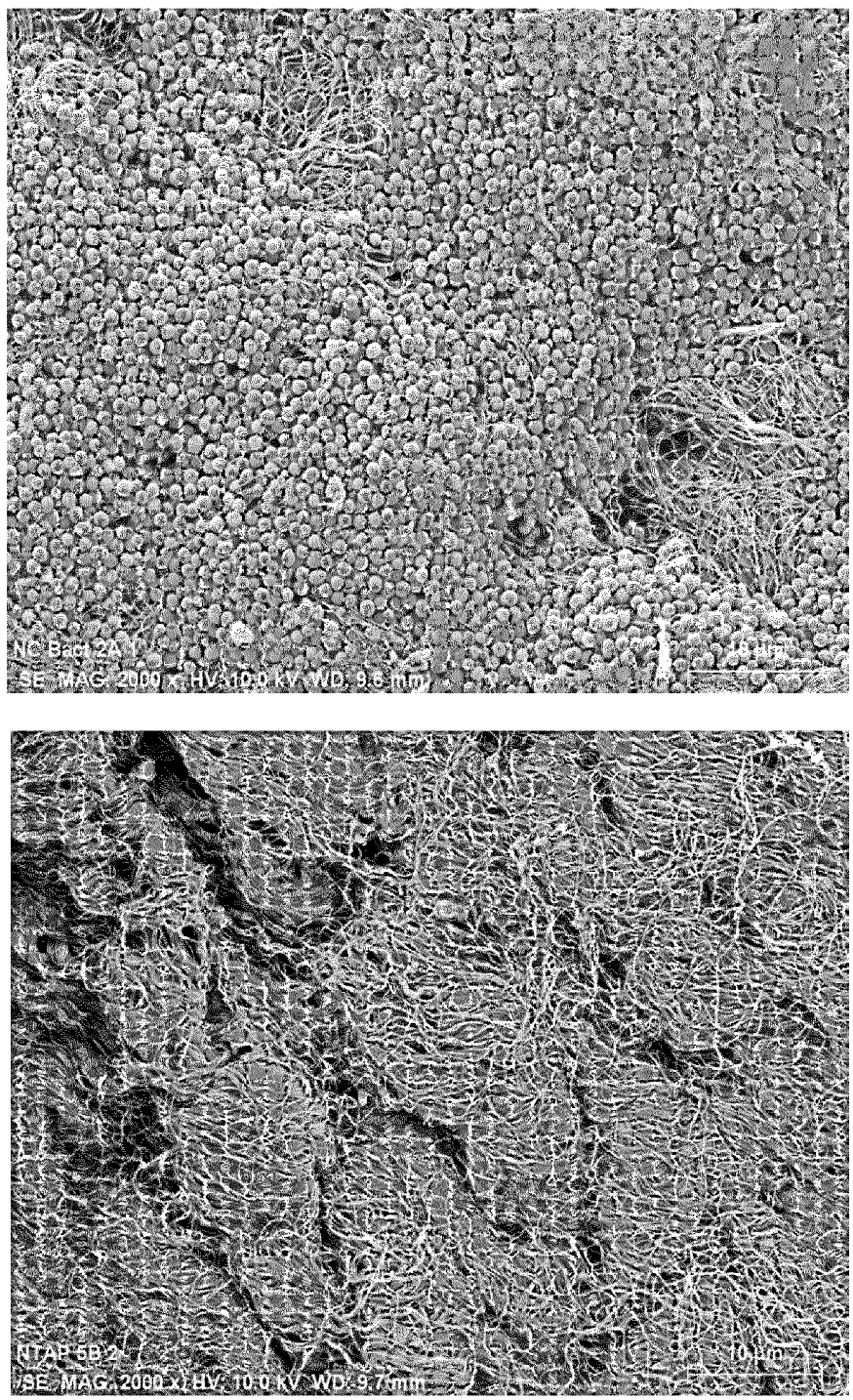

FIG. 21—shows SEM analysis of a biological valve surface after 24-hour incubation with S. aureus. Non-coated and nanogel-modified surfaces are compared (magnification=2000×).

Figure 22:
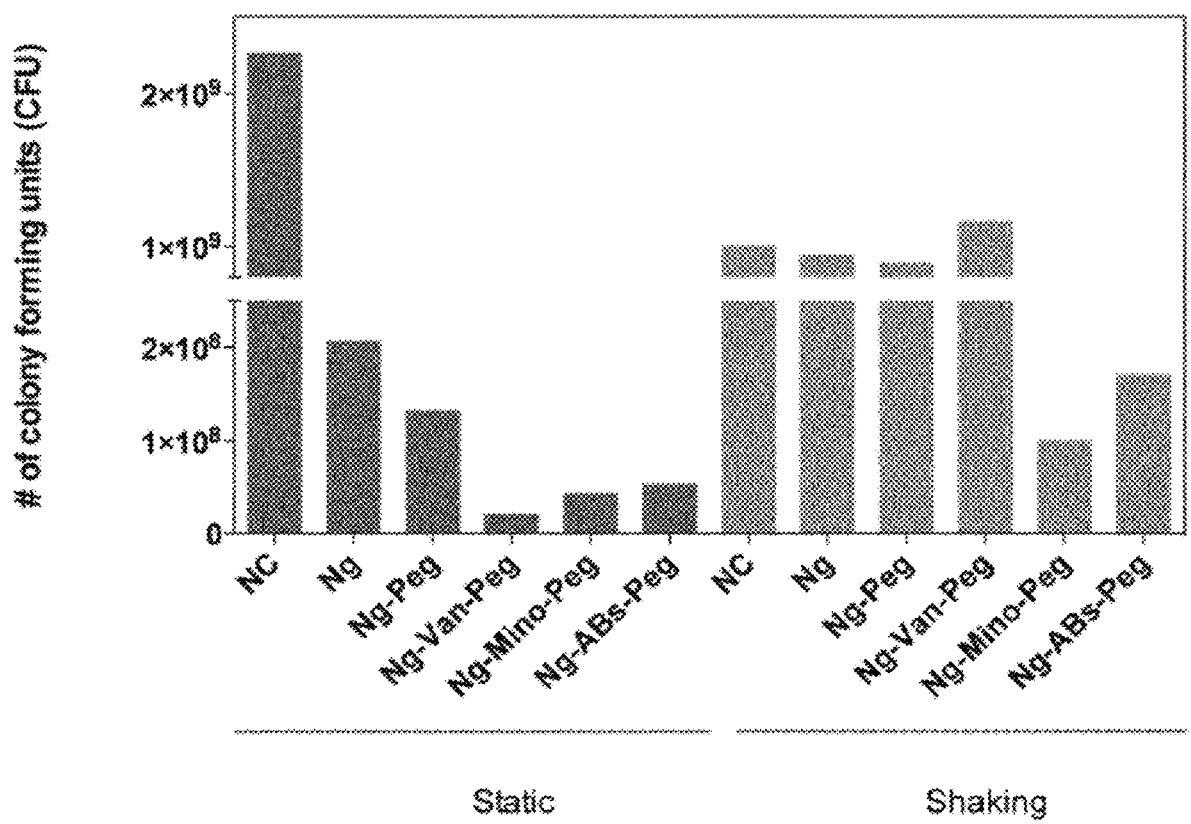

FIG. 22—shows E. faecalis bacteria grown for 24 hours on modified polystyrene surfaces under static or shaking conditions. CFU counting of planktonic bacteria plated on TSB agar plates is also shown.

Figure 23:
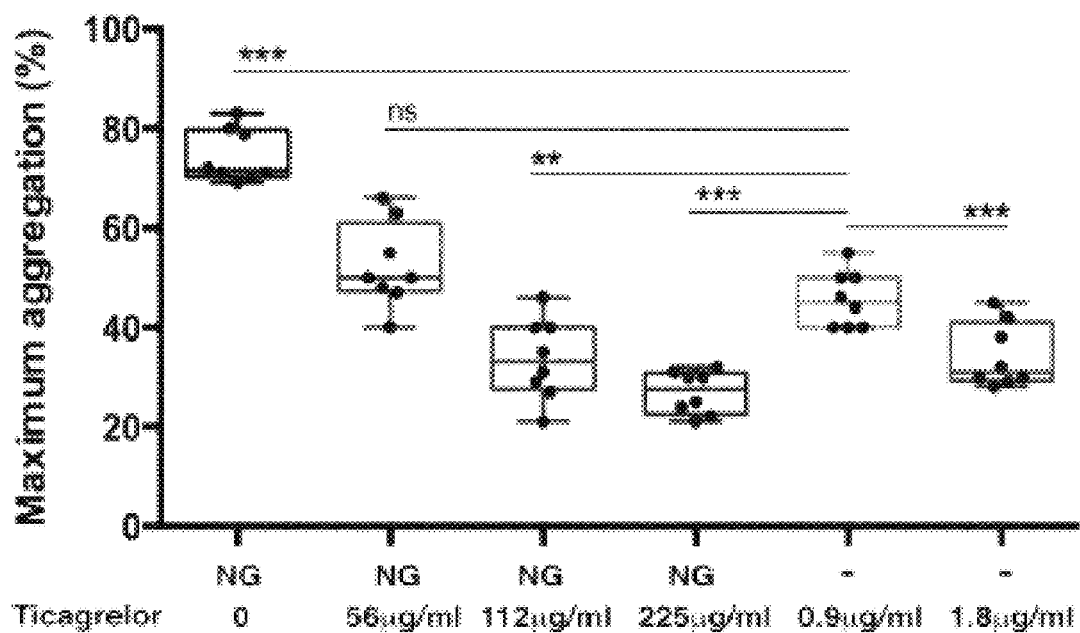
Figure 23:
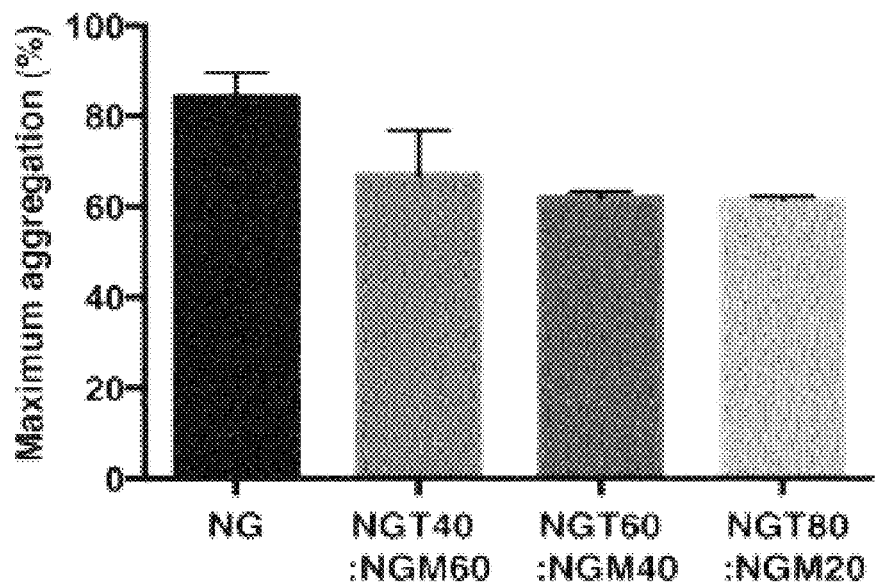

FIG. 23—shows the results of a study of nanoreservoir anti-thrombotic property in solution by platelet aggregation assays. (A) PRP was pre-incubated for 10 min with a solution of nanoreservoir containing increasing concentrations of ticagrelor or with free ticagrelor, as indicated. Platelet aggregation was induced by adding 10 μM ADP at 37° C. under stirring conditions (1200 rpm). Percentages of maximum aggregation recorded by light transmission aggregometry are shown. Data represent means±SD ($*p<0.05$, $p<0.01$, $*p<0.001$). (B) Maximum platelet aggregation obtained in the presence of different ratios of ticagrelor-loaded nanogels and minocycline-loaded nanogels. NG: nanogel bearing PEG 1500; NGT: ticagrelor-loaded nanogel bearing PEG 1500; NGM: minocycline-loaded nanogel bearing PEG 1500. Data represent means±SD.

Figure 24:
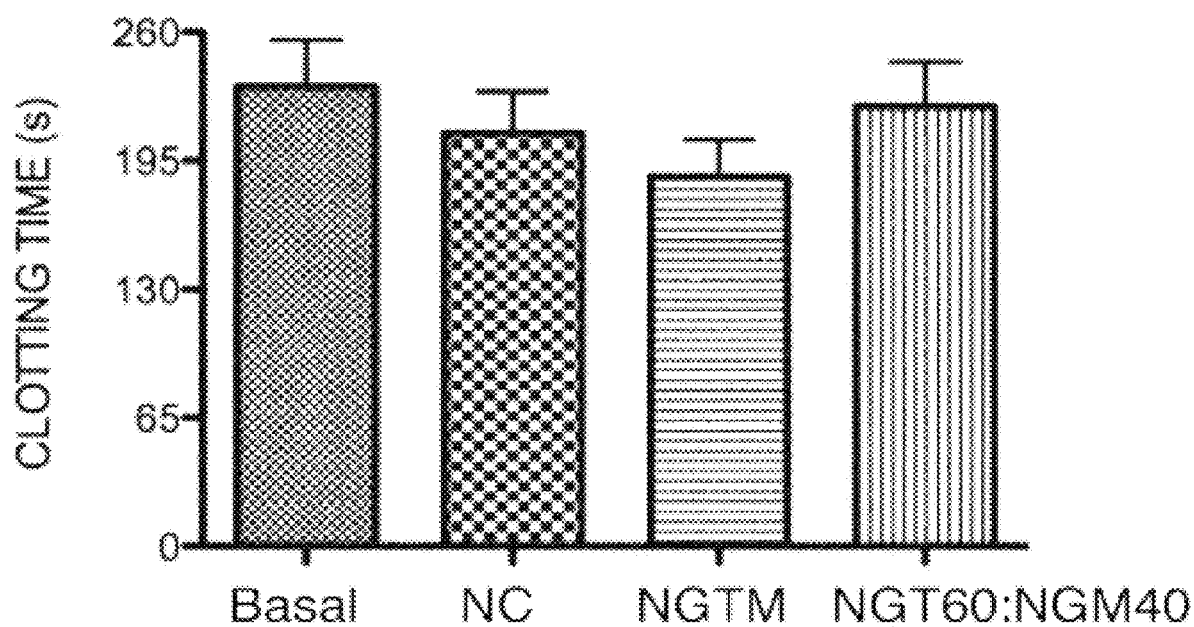

FIG. 24—illustrates the results of a study of the effect of immobilized nanoreservoir on the activation of the contact phase of coagulation in human plasma. Standard plasma was incubated on the coated and non-coated PS surfaces for 10 min. Mixed minocycline- and ticagrelor-loaded nanogels in a ratio of 2/3 (NGT60:NGM40) is compared to nanogels loaded with the two drugs (NGTM). Basal: plasma that has not been in contact with the test surfaces. NC: non-coated. Data represent means±SD.

Figure 25:
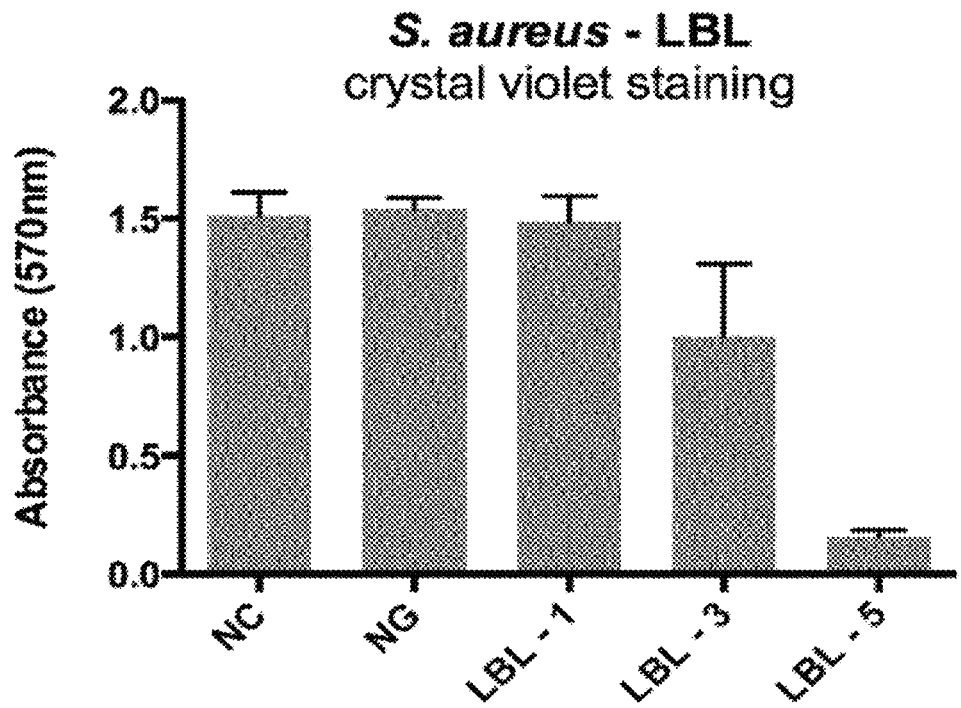
Figure 25:
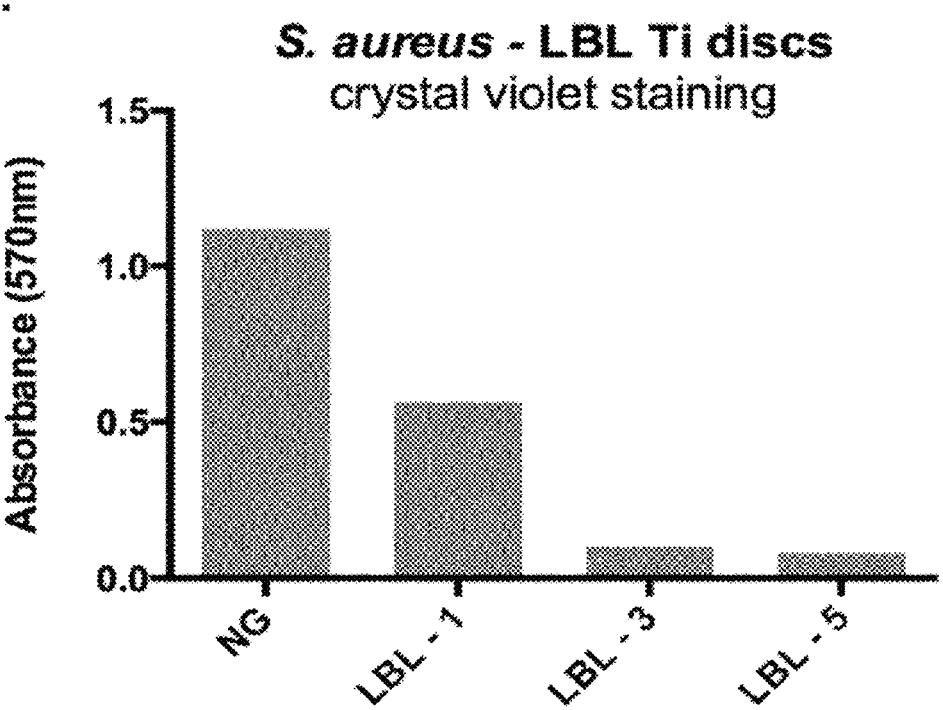

FIG. 25—illustrates the results of a study of multilayer nanogel assembly on S. aureus biofilm formation. (A) Bacteria were let to adhere on coated and non-coated PS surface for 24 h before crystal violet staining. Data represent means±SD. (B) Bacteria were let to adhere on coated and non-coated titanium surface for 24 h before crystal violet staining. Data are representative of two independent experiments. NC: non-coated; NG: non-loaded nanogel bearing PEG 1500; LBL-1,3,5: 1, 3, and 5 layers of a mixture of nanogels loaded with minocycline and ticagrelor in a ratio of 2/3.

Figure 26:
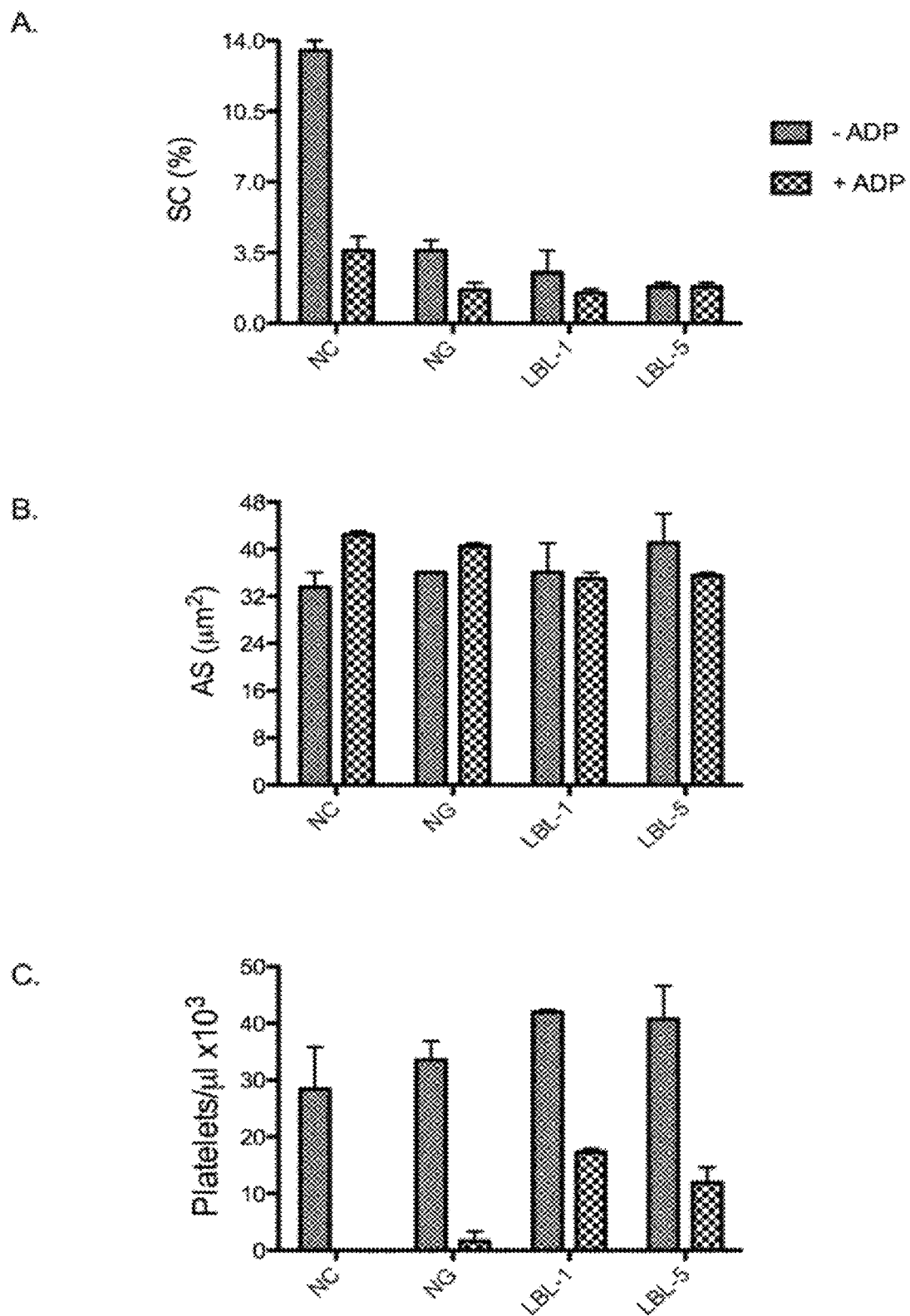

FIG. 26—illustrates the results of a study of multilayer nanogel assembly on antiplatelet effect of nanoreservoirs. NC: non-coated; NG: non-loaded nanogel bearing PEG 1500; LBL-1,3,5: 1, 3, and 5 layers of a mixture of nanogels loaded with minocycline and ticagrelor in a ratio of 2/3. Data represent means±SD.

Figure 27:
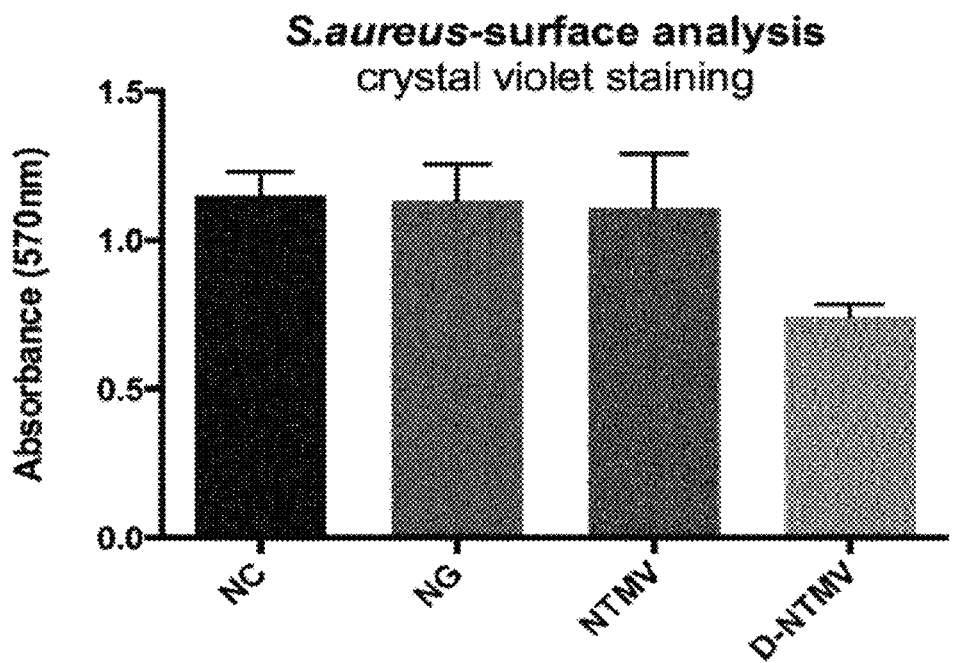
Figure 27:
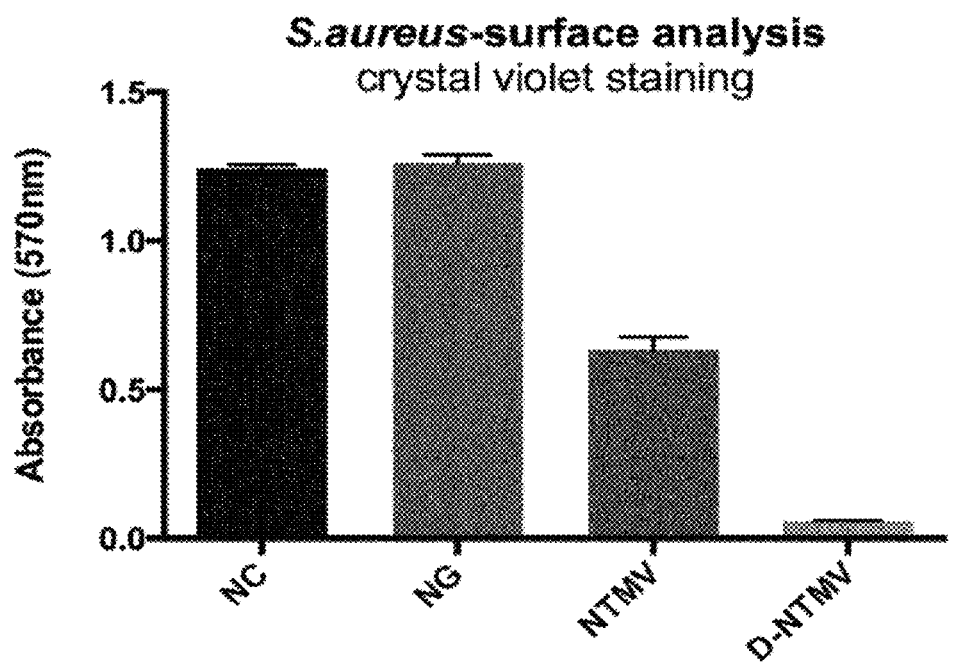

FIG. 27—shows that cross-linking of the 5-layer nanogels with dopamine sustains the antibiotic efficacy against S. aureus biofilm formation beyond 48 h. (A) Surfaces were incubated for two times 24 h with fresh medium before adding S. aureus bacteria. Biofilm formation was quantified by crystal violet staining after 24 h. (B) Anti-biofilm effect of medium removed after the second 24 h of contact with the test surfaces. NC: non-coated; NG: 5-layer nanogel with PEG 1500; NTMV: 5-layer nanogel with PEG 1500, loaded with ticagrelor, minocycline and vancomycin; D-NTMV: dopamine cross-linked S-layer nanogel with PEG 1500, loaded with ticagrelor, minocycline and vancomycin. Data represent means±SD.

Figure 28:
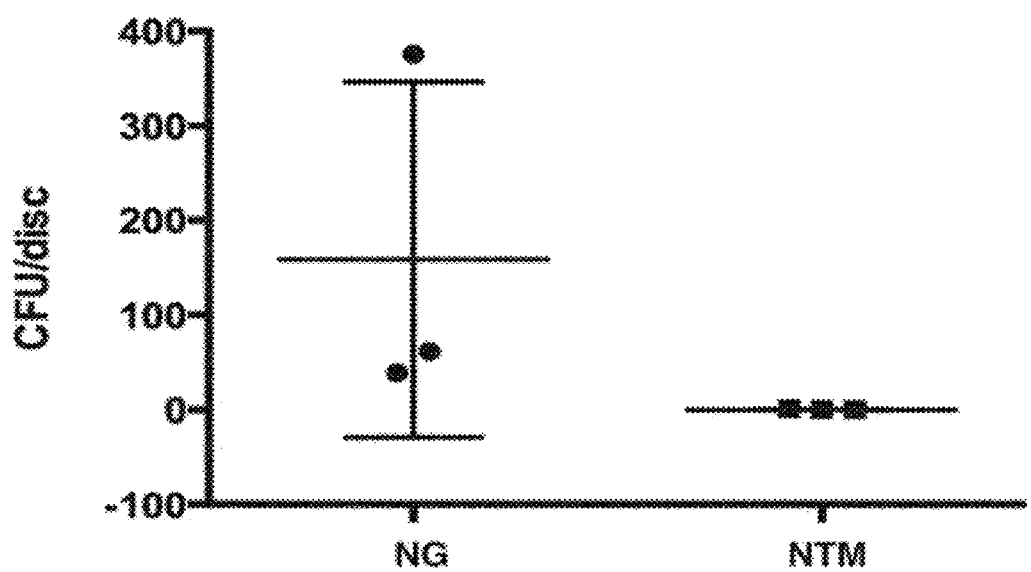
Figure 28:
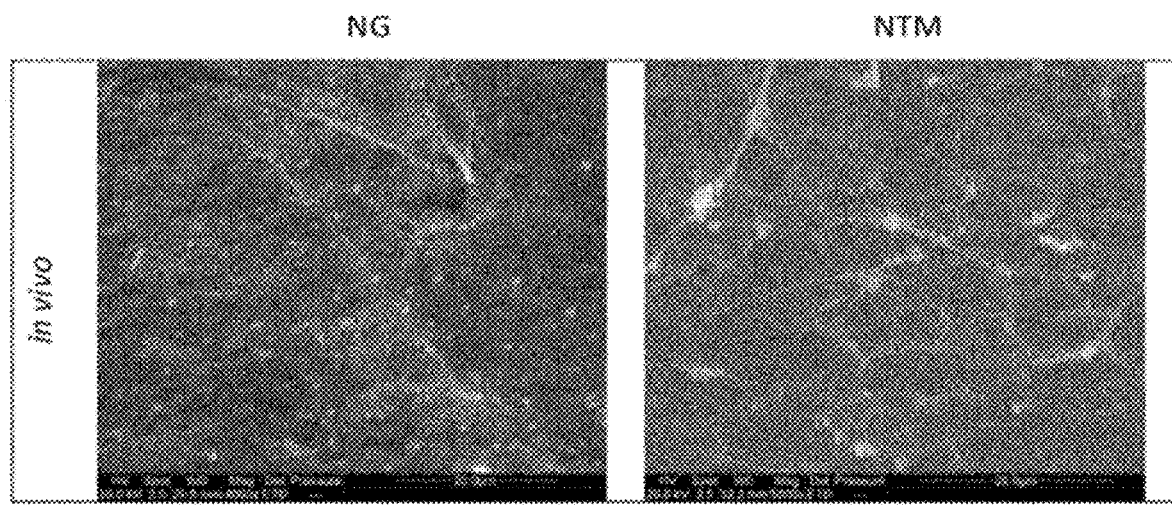

FIG. 28—shows the results of in vivo analysis of the anti-biofilm efficacy of nanoreservoir immobilized on titanium implants. (A) S. aureus pre-infected titanium discs were implanted subcutaneously in mice (n=3) and left for 3 h before analysis of live bacteria on the implants by CFU counting. (B) Surface analysis of the implants by SEM (magnification 2000×).

Figure 29:
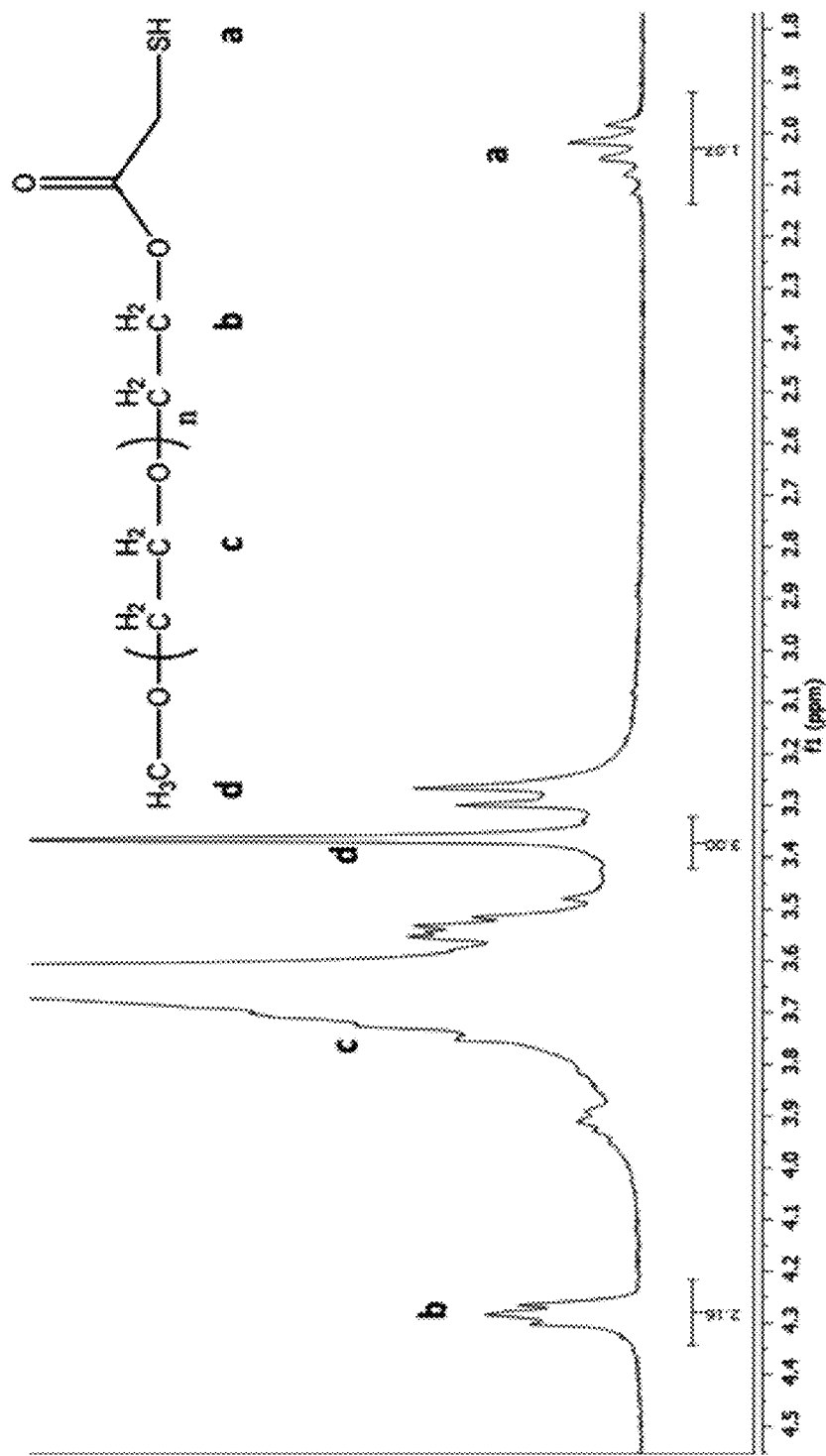

FIG. 29—shows the 1H NMR spectrum of thiol end functionalized PEG1.5 recorded in CDCl3 with peak assignments.

Figure 30A:
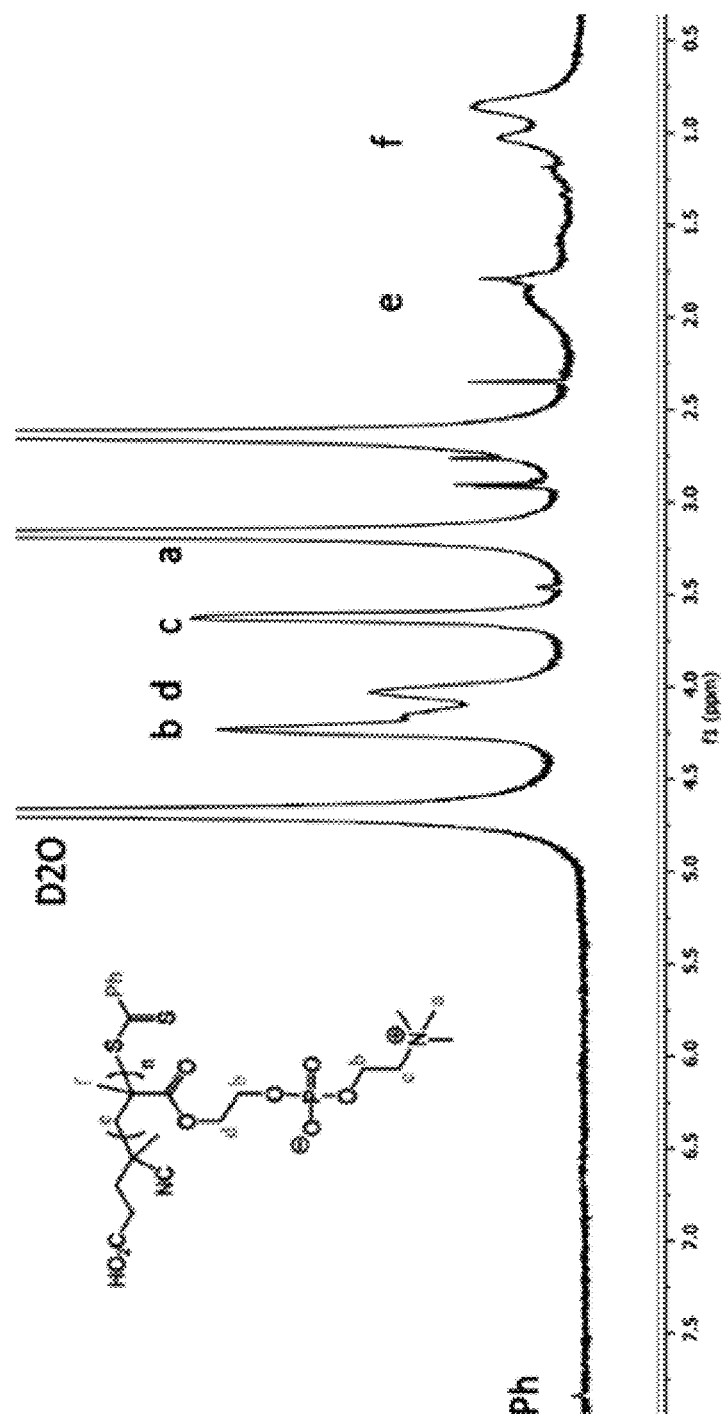
Figure 30B:
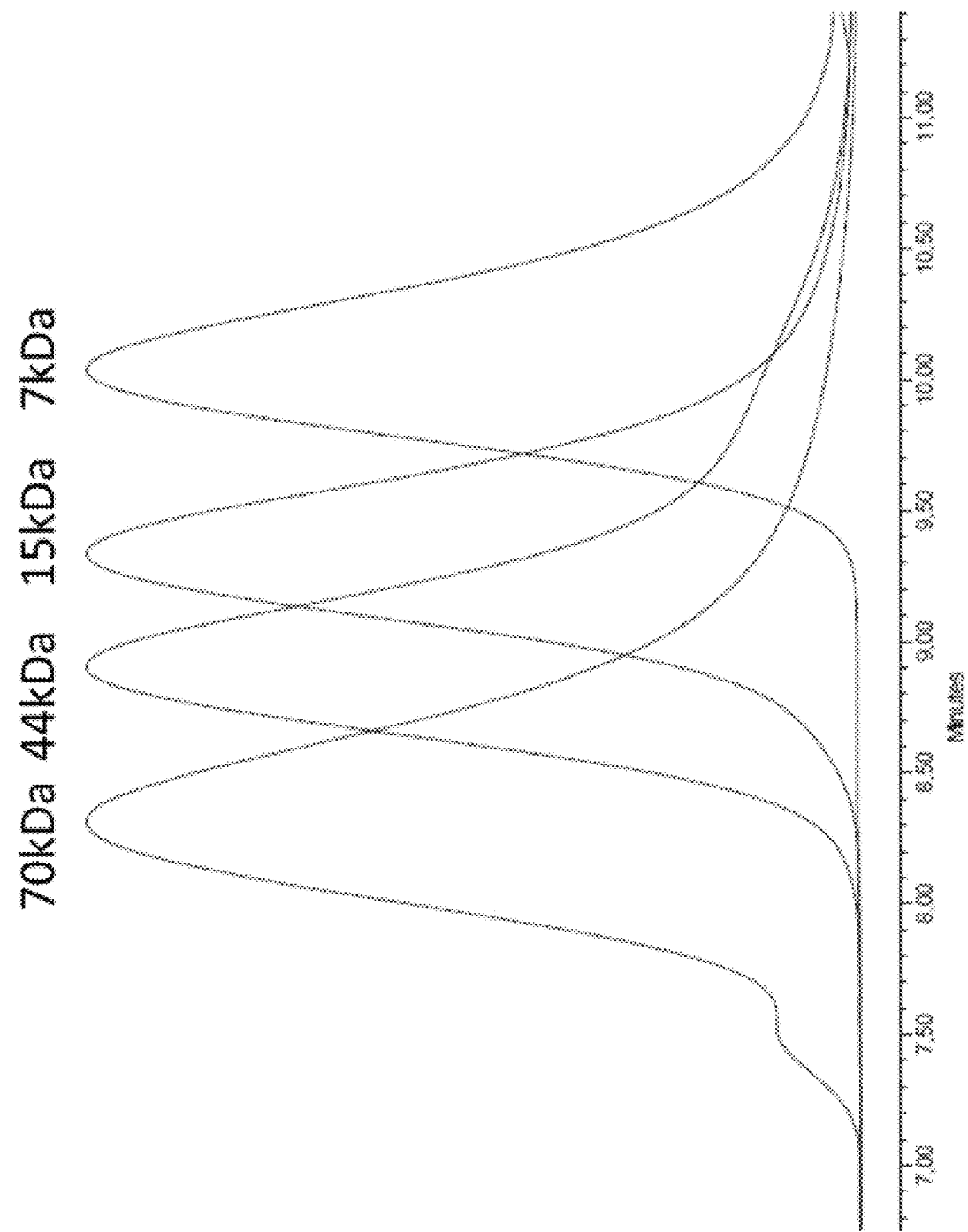

FIG. 30—shows the (A) 1H NMR spectrum of polymerized (2-(Methacryloyloxy)ethyl Phosphorylcholine) recorded in D20 with peak assignments. (B) Aqueous size exclusion chromatogram of four different molecular weights of these polybetaines.

Figure 31:
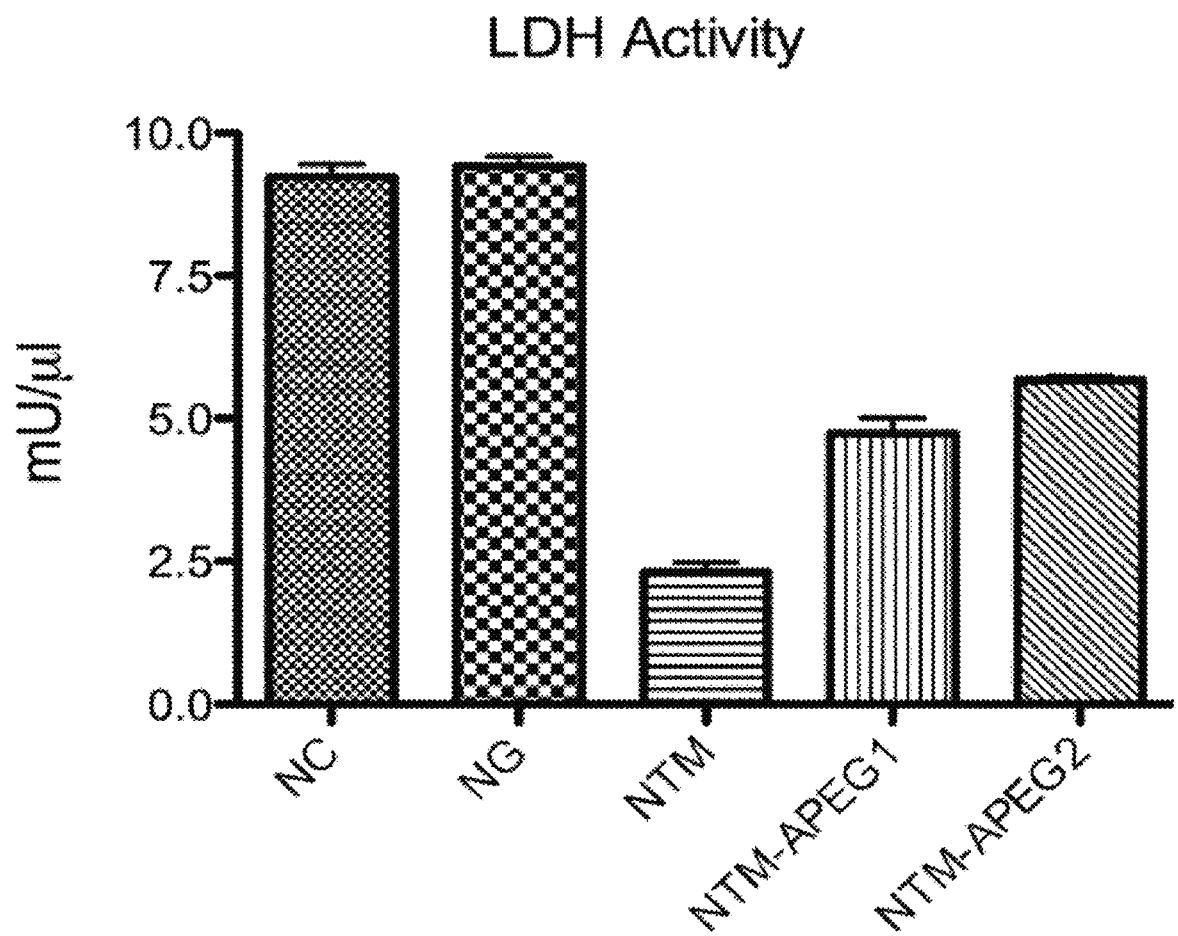

FIG. 31—shows the LDH activity assay of platelet adhesion on polystyrene surfaces. PRP was incubated for 45 min on the indicated coated and non-coated surfaces. NC: non-coated; NG: 5-layer nanogel with PEG 1500; NTM: minocycline and ticagrelor containing nanreservoir (5-layer nanogels-PEG 1500 in a ratio 2/3); NTM-APEG1: minocycline and ticagrelor containing nanreservoir (5-layer nanogels-PEG acrylate 1000 in a ratio 2/3); NTM-APEG2: minocycline and ticagrelor containing nanreservoir (5-layer nanogels-PEG acrylate 2000 in a ratio 2/3). Data represent means±SD.

Figure 32:
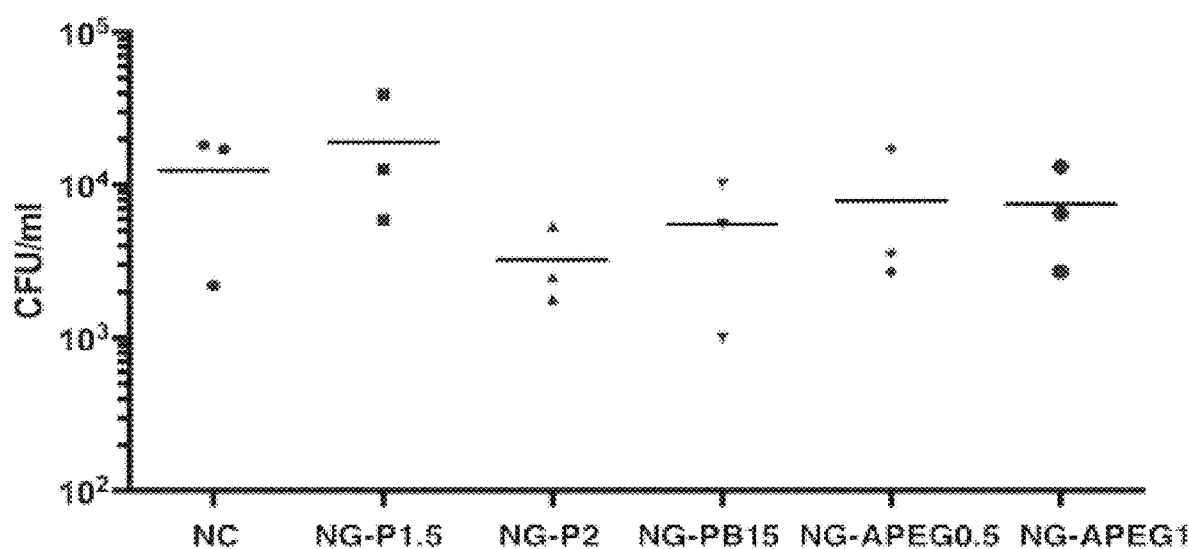

FIG. 32—shows S. aureus biofilm formation on titanium implants coated or not with with 5-layer nanogels bearing different ligands with thiol or vinyl functionalized ends. Bacteria were let to adhere for 3 h before CFU counting. NC: non-coated; NG-PB15: 5-layer nanogels with polybetaine 15 kD as last layer; NG-P1.5, NG-P2: 5-layer nanogels with PEG 1.5 kD, or 2 kD as last layer. NG-APEG0.5: 5-layer nanogels-PEG acrylate 500; NG-APEG1: 5-layer nanogels-PEG acrylate 1000. Data represent means±SD.

Figure 33:
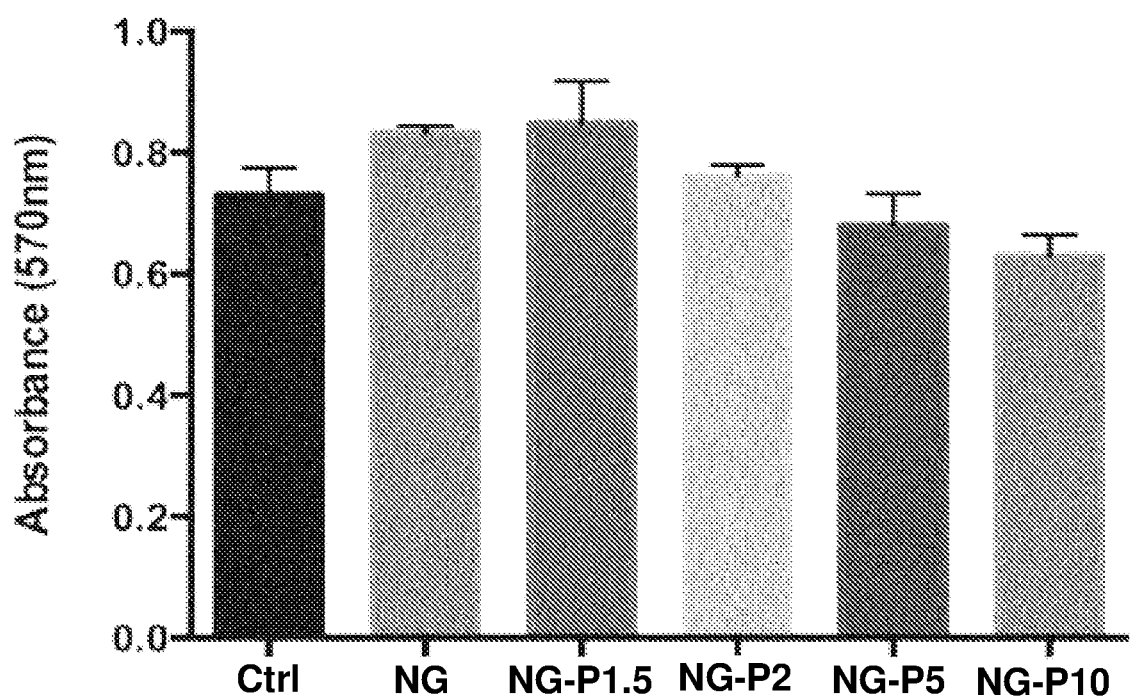

FIG. 33—shows S. aureus biofilm formation on PS surface coated or not with with 5-layer nanogels bearing PEG of different molecular weights. Bacteria were let to adhere for 24 h before biofilm quantification by crystal violet staining. Ctrl: non-coated; NG: 5-layer nanogel without grafted polymer; NG-P1.5, NG-P2, NG-P5, NG-P10: 5-layer nanogels with PEG 1.5 kD, 2 kD, 5 kD, 10 kD as last layer. Data represent means±SD.

Figure 34:
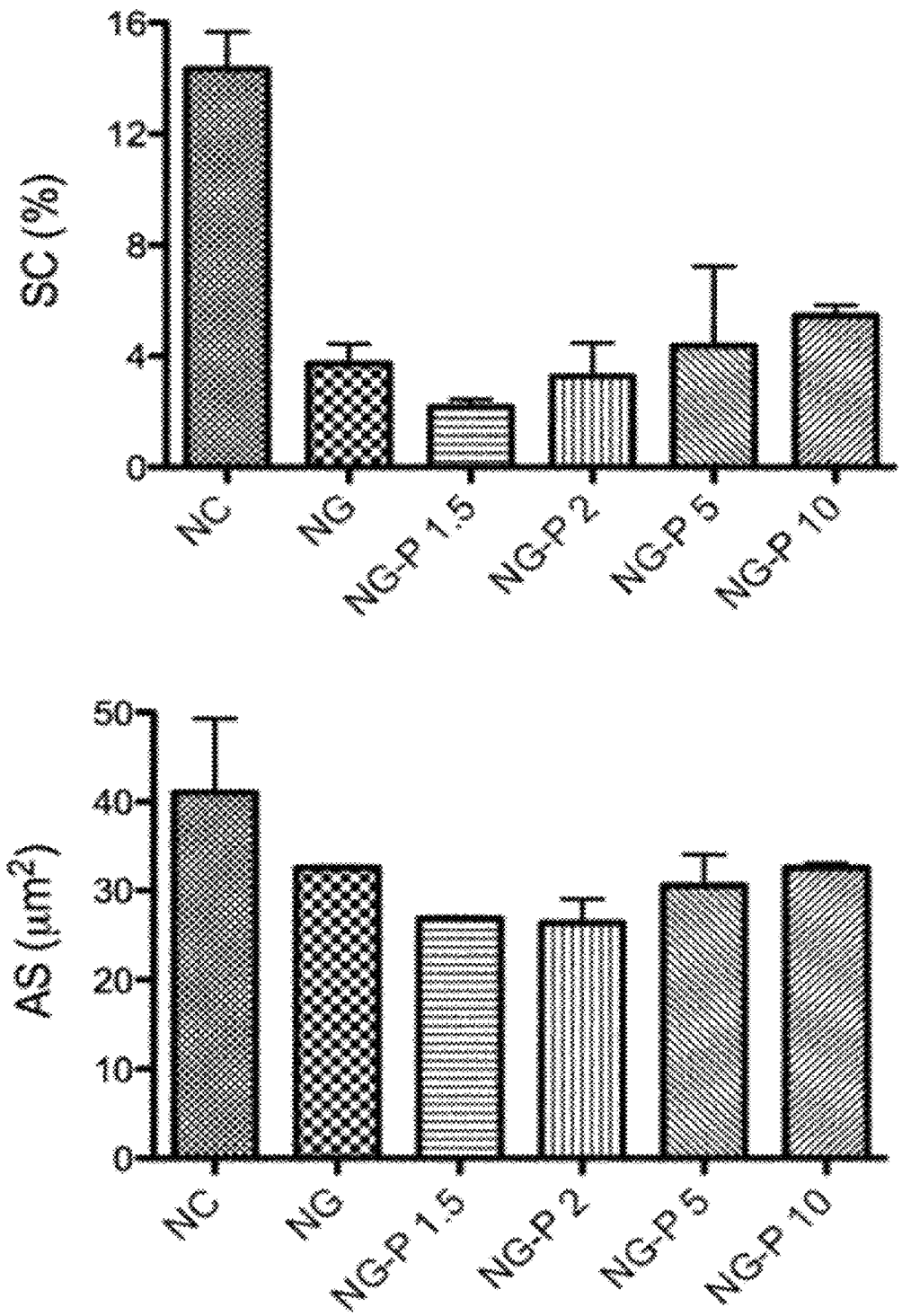

FIG. 34—illustrates the results of a study of the effect of thiol end PEG of different molecular weight on platelet adhesion under flow using Impact-R under flow using Impact-R. Citrated whole blood was added to PS wells before applying 780 rpm for 4 min. Surface coverage (SC) and aggregate size (AS) were determined. NC: non-coated; NG: 5-layer nanogel without grafted polymer; NG-P1.5, NG-P2, NG-P5, NG-P10: 5-layer nanogels with PEG 1.5 kD, 2 kD, 5 kD, 10 kD as last layer. Data represent means±SD.

Figure 35:
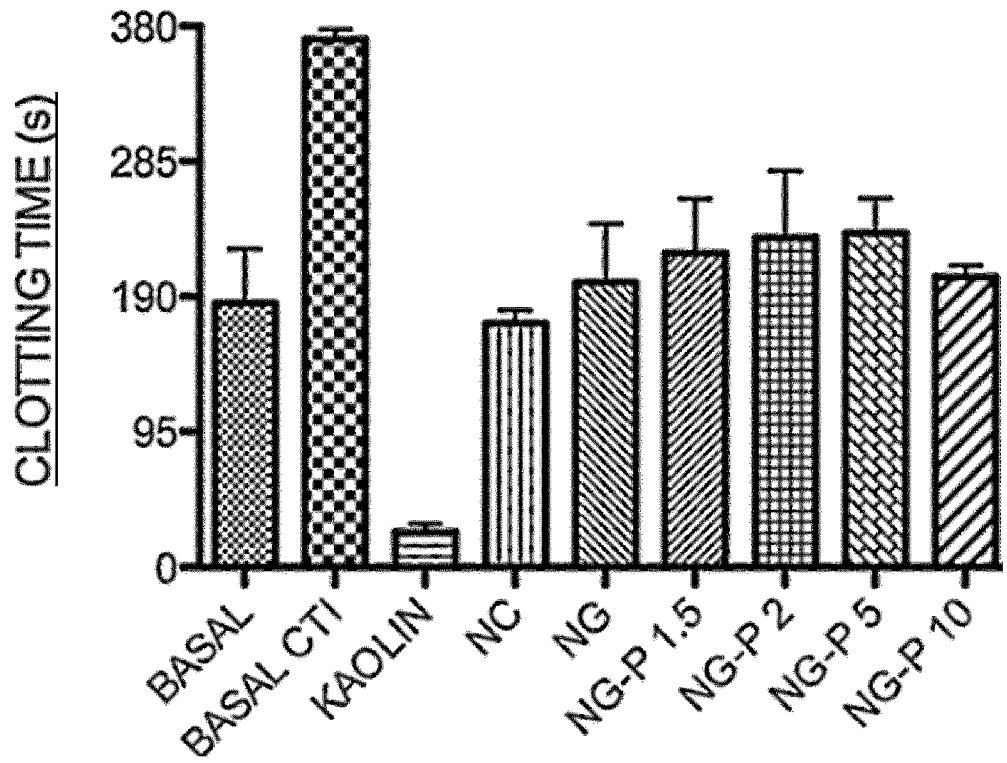

FIG. 35—illustrates the results of a study of the effect of 5-layer nanogels bearing PEG thiol of different molecular weights on the activation of the contact phase of coagulation. Standard human plasma was incubated for 10 min at 37° C. before clotting time analysis in the presence of the Nodia Non Activated Partial Thromboplastin Time (NaPTT) reagent. Kaolin is used as positive control. CTI: corn trypsin inhibitor; NC: non-coated; NG: 5-layer nanogel without grafted polymer; NG-P1.5, NG-P2, NG-P5, NG-P10: 5-layer nanogels with PEG 1.5 kD, 2 kD, 5 kD, 10 kD as last layer. Data represent means±SD.

Figure 36:
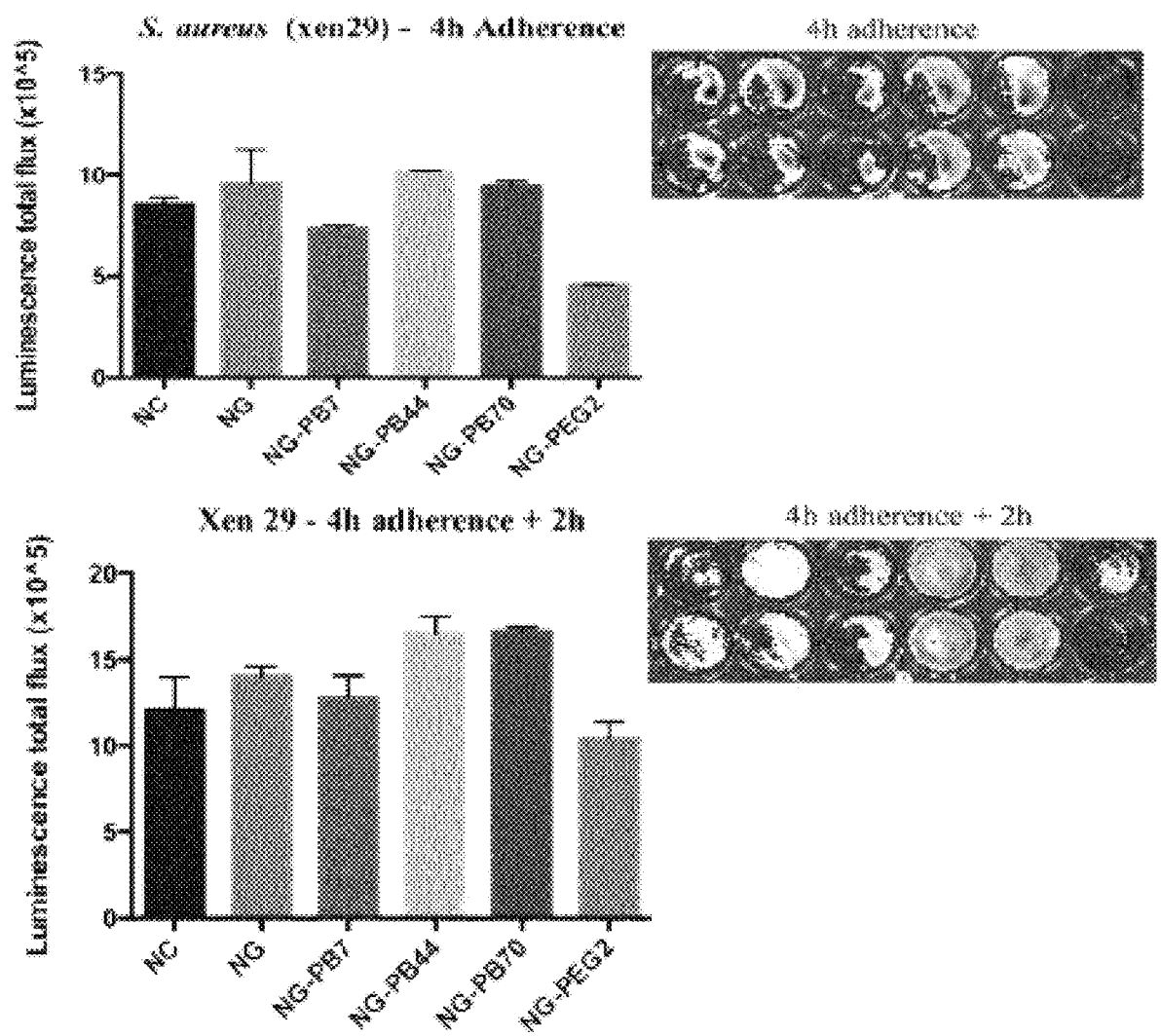

FIG. 36—shows S. aureus Xen-29 biofilm formation on PS surfaces coated with 5-layer nanogels bearing or not PEG thiol or polybetaines of different molecular weight. Bacteria were let to adhere for 4 h before removing the medium and quantifying photon emission, which is directly proportional to bacteria adhesion, either immediately (top panel) or after 2 h (bottom panel). NC: non-coated; NG: 5-layer nanogel without grafted polymer; NG-PB7, NG-PB15, NG-PB44, NG-PB70: 5-layer nanogels with polybetaine 7 kD, 15 kD, 44 kD, 70 kD as last layer; NG-P2: 5-layer nanogels with PEG 2 kD as last layer. Data represent means±SD.

Figure 37:
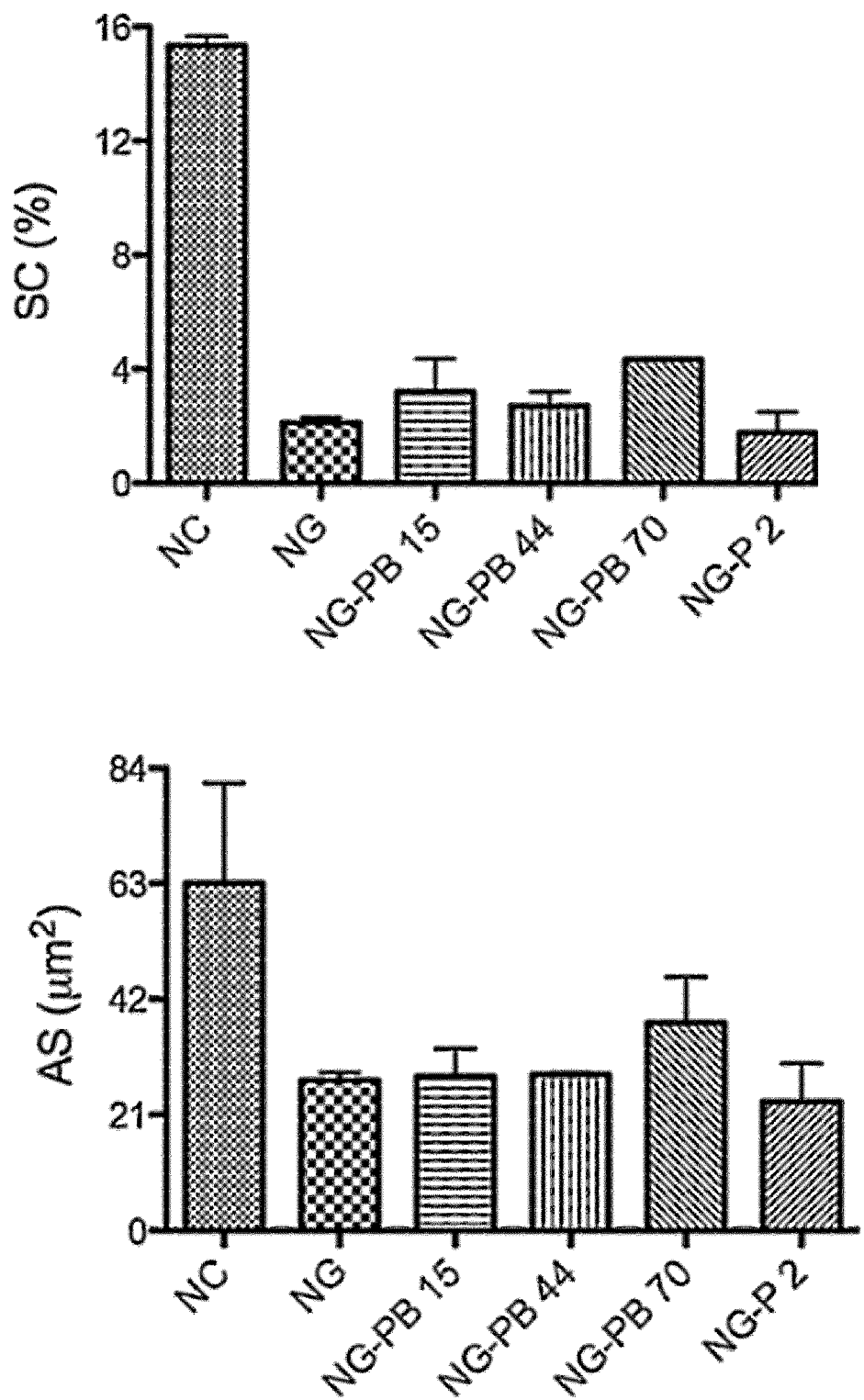

FIG. 37—illustrates the results of a study of the effect of thiol end PEG and polybetaines on platelet adhesion under flow using Impact-R. Citrated whole blood was added to PS wells before applying 780 rpm for 4 min. Surface coverage (SC) and aggregate size (AS) were determined. NC: non-coated; NG: 5-layer nanogel without grafted polymer; NG-PB7, NG-PB15, NG-PB44, NG-PB70: 5-layer nanogels with polybetaine 7 kD, 15 kD, 44 kD, 70 kD as last layer; NG-P2: 5-layer nanogels with PEG 2 kD as last layer. Data represent means±SD.

Figure 38:
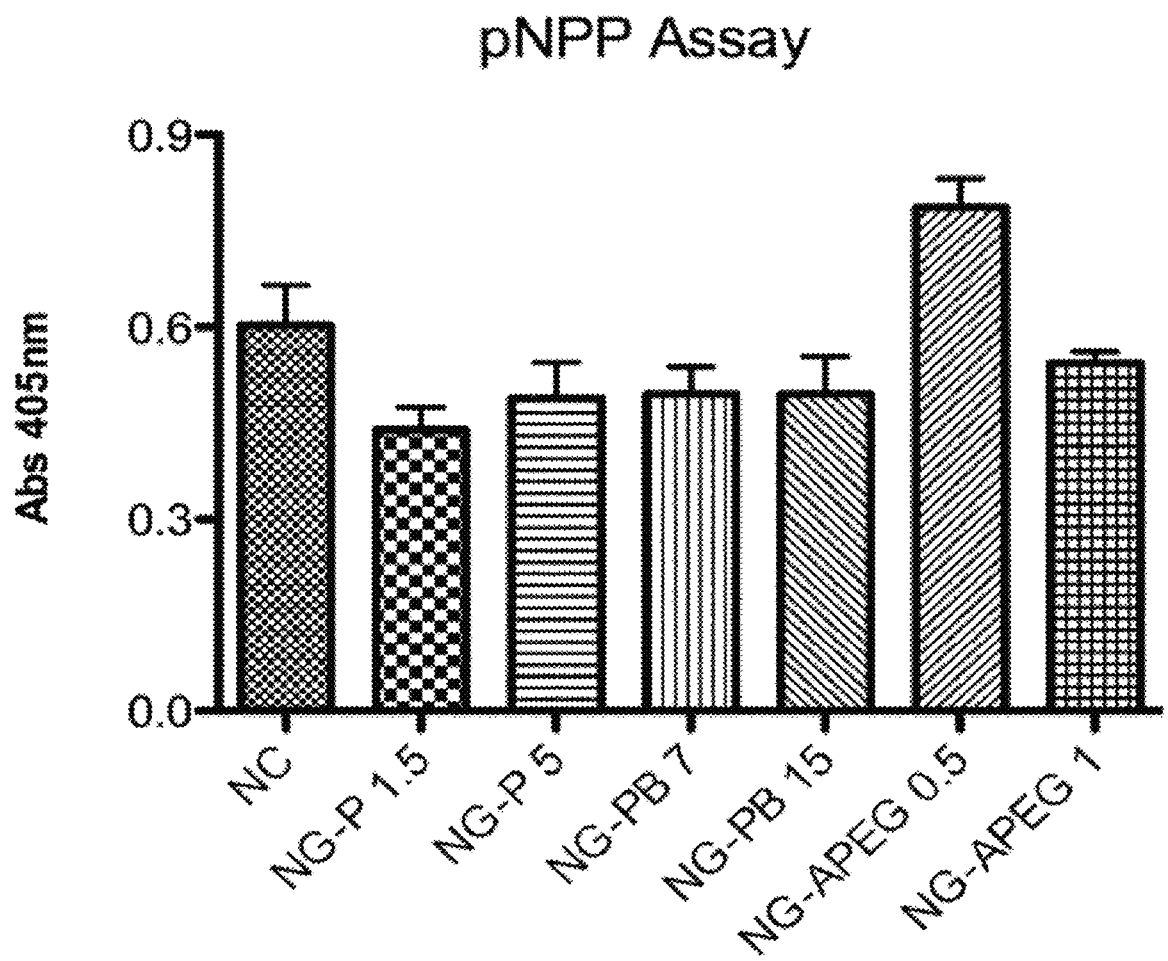

FIG. 38—shows the results of a pNPP assay of platelet adhesion on polystyrene surfaces. PRP was incubated for 45 min on the indicated coated and non-coated surfaces. NC: non-coated; NG-PB7, NG-PB15: 5-layer nanogels with polybetaine 7, or 15 kD as last layer; NG-P1.5, NG-P5: 5-layer nanogels with PEG 1.5 kD, or 5 kD as last layer. NG-APEG0.5: 5-layer nanogels-PEG acrylate 500; NG-APEG1: 5-layer nanogels-PEG acrylate 1000. Data represent means±SD.

Figure 39:
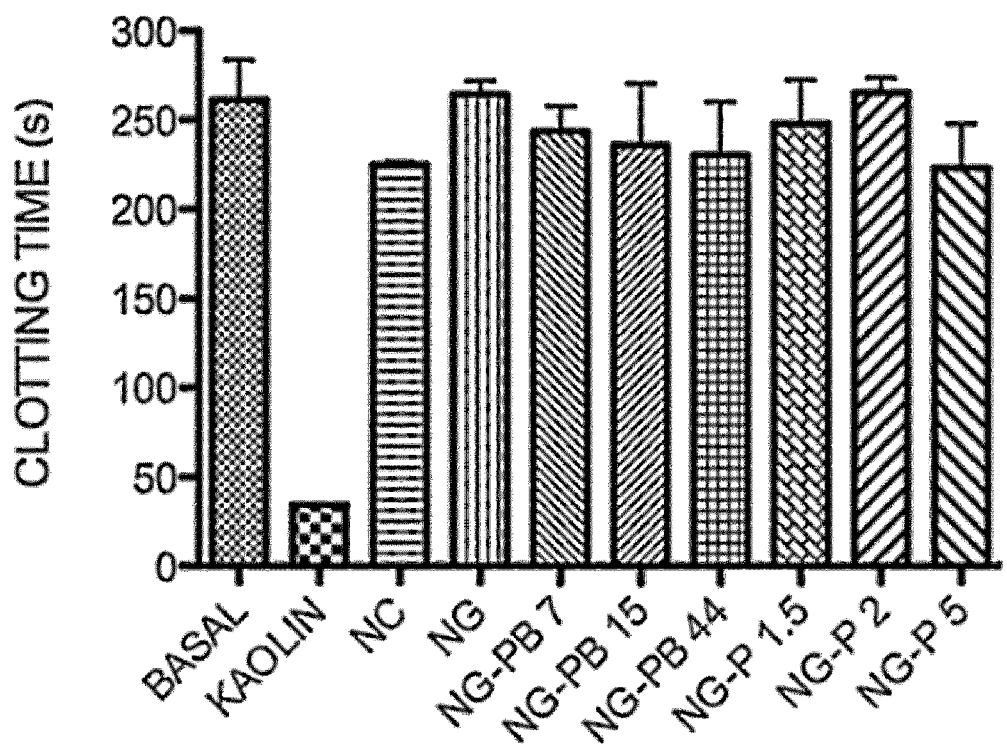

FIG. 39—illustrates the results of a study of the effect of 5-layer nanogels bearing PEG thiol or polybetaine of different molecular weight on the activation of the contact phase of coagulation. Standard human plasma was incubated for 10 min at 37° C. before clotting time analysis in the presence of the Nodia Non Activated Partial Thromboplastin Time (NaPTT) reagent. Kaolin is used as positive control. NC: non-coated; NG: 5-layer nanogel without grafted polymer; NG-PB7, NG-PB15, NG-PB44: 5-layer nanogels with polybetaine 7 kD, 15 kD, 44 kD as last layer; NG-P1.5, NG-P2, NG-P5: S-layer nanogels with PEG 1.5 kD, 2 kD, 5 kD as last layer. Data represent means±SD.

Figure 40:
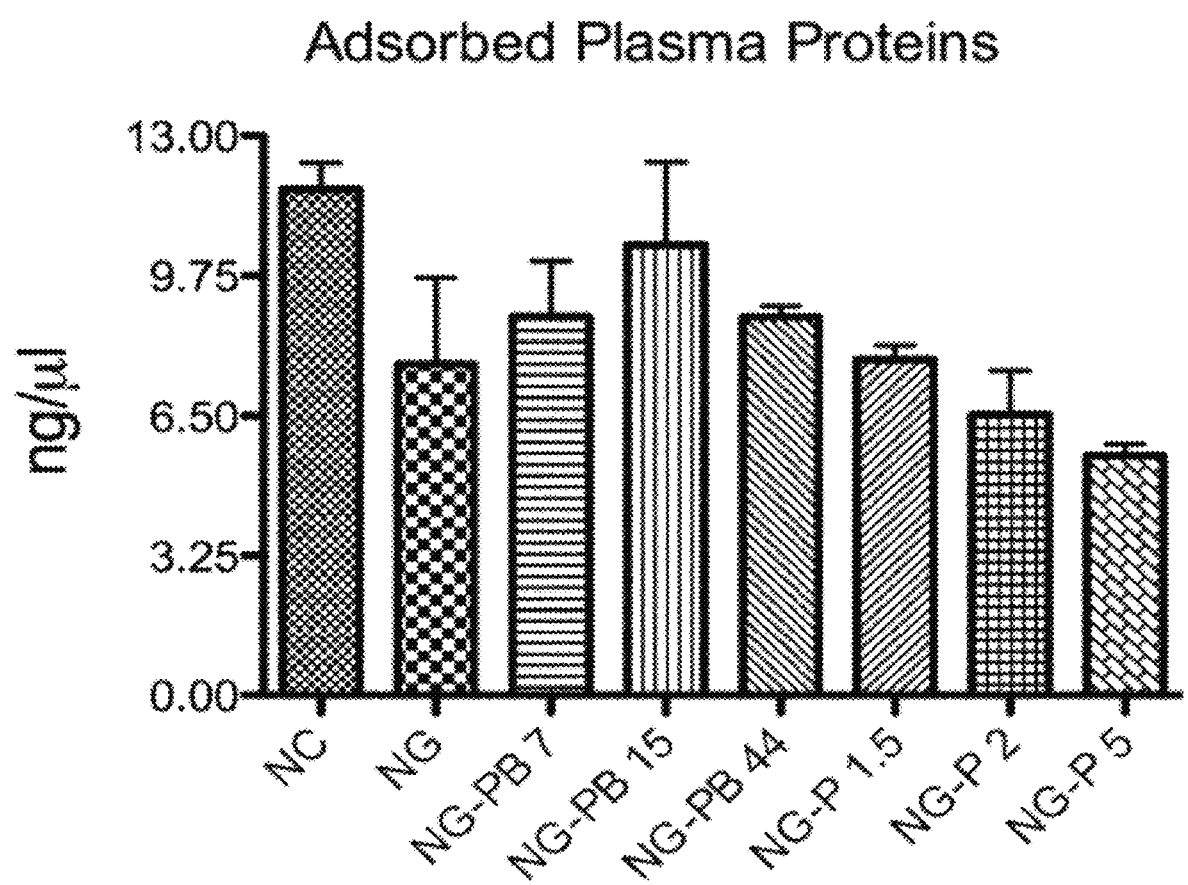

FIG. 40—shows the quantification of plasma proteins adhered onto coated and non-coated polystyrene surface after incubation of standard human plasma for 10 min at 37° C. NC: non-coated; NG: 5-layer nanogel without grafted polymer; NG-PB7, NG-PB15, NG-PB44: 5-layer nanogels with polybetaine 7 kD, 15 kD, 44 kD as last layer; NG-P1.5, NG-P2, NG-P5: 5-layer nanogels with PEG 1.5 kD, 2 kD, 5 kD as last layer. Data represent means±SD.

The invention now being generally described, it will be more readily understood by reference to the following examples which are included merely for purpose of illustration of certain aspects and embodiments of the present invention, and are not intended to limit the invention in any way.

Materials and Methods
Materials
Reagents

Antibiotics (minocycline, vancomycin) were purchased from Sigma, the antiplatelet drug Ticagrelor was from Cayman Chemicals.

Blood collection tubes: sodium citrate Vacutainer tubes (3.2% Sodium Citrate) were from BD Biosciences.

Bacteria strains and culture media: S. epidermidis, strain RP62A (#35984) was from ATCC; S. aureus, E. faecalis were purchased from ATCC (25904 and 29212); S. aureus—Xen29 bioluminescent pathogenic bacteria were from Perkin Elmer (#119240). Tryptic Soy Broth (TSB) and agar powder was from Sigma-Aldrich.

Sample preparation Sterilization of surfaces before in vitro testing: all coated or non-coated surfaces were sterilized in 100% absolute ethanol for 10 min followed by 2 to 5-minutes-incubation washes in distillate water and one wash in 0.9% NaCl.

Blood from healthy donors (under no medication and that did not take any aspirin or other anti-coagulant drug in the last 20 days prior the drawing) was drawn using a 18 g needle and directly let flow in a 50 mL polypropylene tube containing 3.2% sodium citrate (1 volume citrate for 9 volumes of blood) for the static test or using a 21 g needle and citrate vacutainers tubes for dynamic tests. The study was approved by the Ethics Committee of the University Hospital of Liege, Belgium. An informed consent was signed by the donors.

Experimentations using S. aureus were conducted in a biosafety level 2 room of the GIGA-R.

Dynamic In Vitro Impact-R Test

The blood was rested in the tube for 45 min before any processing at the cone & plate device Impact-R system (Matis Medical). Blood was then mixed at 10 rpm for 1 min at room temperature before the application of shear stress. For each test 130 µL of blood was carefully deposited on the well. The shear stress applied was 1800 s−1 for 4 min (corresponding to 780 rpm bell speed): this speed and incubation time simulates the laminar arterial blood flow over a polystyrene surface and is useful to analyze platelet function under shear stress.

After the 4 min application of shear stress, blood was collected and analyzed by Cell Dyn for single platelet count, while the PS wells coated or not were gently washed with distilled water 4 times and stained with May-Grünwald stain solution for 1 min at RT. Platelets that adhered on the surface were visualized with an optical microscope and quantified using the Impact-R software. Two parameters were obtained from the analysis (i) the surface coverage (SC %) and (ii) the aggregate size of the platelets (AS µm). Every condition was repeated in duplicate per each donor.

Static In Vitro Test

Platelet adhesion on surfaces was analysed by using one of the following photometric assays: the LDH (Lactate Dehydrogenase Test) and the p-NitroPhenil Phosphate (pNPP) test. Values obtained from both tests are directly proportional to the number of platelets adhering to the surface. LDH released upon platelet lysis is indirectly analysed by measuring the conversion of NAD to NADH, detected at 450 nm. The pNPP test measures the levels of alkaline and acid phosphatases released upon platelet lysis. The hydrolysis of pNPP, a substrate of these phosphatases, produces p-nitrophenol, which has a maximal absorbance at 405 nm and is proportional to the amount of platelets bound to the surface.

Platelet poor plasma (PPP) or platelet rich plasma (PRP) was layered on coated polystyrene surfaces for 45 min at 37° C. Surfaces were washed 3 times with NaCl 0.9%. Lysis of adhered platelets was achieved by adding 1% Triton in PBS for the LDH test, or in 1% Triton in a sodium citrate buffer (0.05M Citrate pH 5.4) containing 5 mM pNPP for the pNPP assay. Background readings from the PPP incubation was subtracted from the PRP reads.

Platelet Aggregation Tests

Platelet-rich-plasma (PRP) was prepared by centrifugation of citrate anticoagulated human blood at 100×g for 15 min at room temperature. Platelet aggregation experiments were performed on PRP aliquots under stirring (1200 rpm) at 37° C. using light aggregometry (Chrono-Log Model 700 aggregometer, Kordia).

Plasma-Biomaterial Interaction: Coagulation Assay and Plasma Protein Adhesion

Clotting tests were performed using the Stago STart® 4 Hemostasis Analyzer and the Nodia Non Activated Partial Thromboplastin Time (NaPTT) reagent. The NaPTT reagent is a synthetic phospholipid platelet substitute intended for the study of activation of contact phase of coagulation. The Stago Analyzer is a semi-automated system integrated with an electro-mechanical clot detection method (Viscosity-based detection system). Clot formation in citrated human standard plasma (Stago) is catalyzed by the addition of $Ca^{2+}$ ions as well as by phospholipids. Kaolin was used as a positive control for contact phase activation, while Corn Trypsin Inhibitor (CTI), a specific inhibitor of factor XIIa, which is the factor initiating the contact activation pathway, was used to determine clotting time independently of this pathway. Standard human plasma was defrost in a water bath at 37° C., and added into coated and non-coated polystyrene (PS) wells for 10 min at 37° C. without stirring. Plasma was then snap frozen in a dry ice/acetone bath (−78° C.) and stored at −80° C. until analysis. On the day of the test, plasma was defrost at 37° C. and immediately processed in the Stago STart® 4 apparatus. The 37° C. pre-warmed Nodia Reagent was added to 100 µl of pre-warmed plasma in a cuvette containing a coated metal bead before initiating coagulation by addition of a pre-warmed calcium solution (8.3 mM). The clotting end point is measured by the pendular movement of the bead alimented by an electromagnetic field. Such movement, which is influenced by the viscosity of the plasma, stops when the viscosity becomes maximal, i.e. when plasma coagulation occurs.

Protein adherence was measured using the Pierce Micro BCA (Bicinchonic Acid) Assay, a highly sensitive method detecting down to 5 ng/ml of protein. Bicinchonic acid binds to $Cu^+$ ions with a 2:1 stoichiometry delivering high sensitivity. The assay is based on the conversion of $Cu^{2+}$ ions into $Cu^+$ by proteins in basic environment. 120 µl of plasma (Stago Standard Plasma) pre-warmed at 37° C. was added in coated and non-coated wells of a 48-well polystyrene (PS) plate (11 mm diameter wells) and incubated for 10 min at 37° C. After 3 washes with NaCl 0.9%, the adhered proteins were detached by adding 250 µl of a solution of SDS 1% in PBS for 10 min at RT. The undiluted protein solution was used in the Micro BCA Assay.

Bacteria Adhesion and Biofilm Formation Analysis

One colony of S. epidermidis or S. aureus or E. faecalis was grown 0/N at 37° C. in TSB medium under agitation (220 rpm), the following day a dilution 1:100 was performed in TSB fresh medium and the suspension was grown for 4 hours until the logarithmic phase ($OD_{595}$=0.5) was reached. Bacteria were then diluted 1/20 in sterile NaCl 0.9% to have around 200000 cfu/µl and 500 µL were incubated in static or dynamic condition for 24 hr at 37° C. in coated or non-coated polystyrene 24-well plates. Bacteria suspensions were analyzed by agar plating and CFU (colony formation unit) counting, while biofilms were analyzed by crystal violet staining. The surface was first washed 3 times with NaCl 0.85% to eliminate planktonic bacteria and then stained with 1% crystal violet for 40 min. After 3 washes with water the crystal violet dye retained in the bacteria was released using 10% Acetic Acid for 10 min. Intensities were measured at 595 nm in a 96-well plate using a spectrophotometer plate reader. Conditions were in duplicates and reads were in triplicate. Kinetics of bacteria adhesion and biofilm formation on surfaces were also assessed by using bioluminescent S. aureus bacteria with the IVIS Lumina system (Perkin Elmer). Bacteria were let adhere for 3 h before washing the wells, and luminescence signals, directly proportional to bacteria density, were then recorded for increasing times. Biofilms were imaged using the IVIS camera system. Total photon emission from selected wells was quantified using the LivingImage software package.

Mouse Model of Biomaterial-Associated Infection Mouse Model: Subcutaneous Implantation of a Pre-Infected Titanium Device and In Vivo Biofilm Formation Staphylococcus aureus was grown for 2 h at 37° C. in TSB medium to reach logarithmic phase. Bacteria were diluted 1:10000 in TSB supplemented with 2% NaCl+1% Glucose and a 800 µl aliquot (corresponding to 20000 CFU/disk) was layered on Titanium 0.2 cm diameter disks (Biotronik). Bacteria were let adhere on all disks for 3 h at 37° C. under static conditions. Bacteria suspension was removed, and the surface was gently washed 3 times in PBS. To determine the number of bacteria that adhered on the titanium disks, half of the disks were sonicated for 5 min in a Fisher waterbath sonicator. The detached bacteria were plated on a TSB agar plate to determine the number of colony forming units (CFU) per disk before implantation. The other half of the disks was implanted in 8-weeks old male BALB/cJRj mice (Janvier Laboratories) as follows. Two hours prior anesthesia, mice were injected subcutaneously with 0.05 mg/kg buprenorphine analgesic (Temgesic). Fifteen minutes before the implantation mice were anesthetized by intraperitoneal injection of a ketamine (125 mg/kg)/xylazine (12.5 mg/kg) mixture. Mice were shaved on the lower ventral side below the rib cage and the area was sterilized with betadine followed by 70% ethanol solution. Using a sterile scalpel an incision was made on the skin and the S. aureus infected or non-infected disks were inserted between the skin and the muscles. After 4 h incubation, mice were sacrificed by cervical dislocation and the devices were analysed to determine CFU/disk (by sonication, like previously described). The protocol was approved by the ethical committee of the ULiege University (#16-1774). SEM images of explanted titanium disks were taken with the Quanta Microscope (magnification is 4000×). Titanium disks were gently washed and fixed in 2.5 glutaraldehyde in Sorensen buffer for 1 h at 4° C., followed by 3 washes in Sorensen buffer and fixation in 2% $OsO_4$ for 1 h at 4° C. The disks were dehydrated in increasing ethanol concentrations, dried under $CO_2$ atmosphere (critical point drying) to keep biological structures and then metallised.

Results and Discussion

EXAMPLES

Example 1. Preparation of Cross-Linked Nanogel and Loading with Bioactive Molecules A homopolymer of methacrylamide bearing 3,4-dihydroxy-L-phenylalanine (P(mDOPA), 1, FIG. 1) was specifically designed to prepare nanogels and to immobilize active (bio)molecules by physical entrapment or covalent conjugation. Cross-linked reactive nanogels can be directly deposited onto a surface pre-coated with a bio-inspired polydopamine layer. This strategy has several advantages over existing methods: i) there is no use of an external cross-linking agent, ii) coupling reactions are fast at room temperature in water, iii) no undesirable side products are formed and released out of the film, and iv) active biomolecules can be covalently grafted to the surface.

A fast and water based cross-linking process was used to exploit the redox properties of DOPA molecules in order to provide reactive function available for nanogel formation and for nanogel functionalization.

Stable solutions of nanogels in water were prepared by adequately controlling both the redox state of the P(mDOPA) polymer and the pH of the PAH solutions. Preparation conditions are crucial for the success of the nanogel formation. First, P(mDOPA) is oxidized in aqueous media under basic conditions for 12 hours to form the hydrosoluble Pox(mDOPA). Oxidized DOPA moieties of Pox(mDOPA) are necessary for the covalent interaction of PAH through amine/quinone reaction and/or Schiff base formation at room temperature, and consequently for the preparation of stable cross-linked nanogel (FIG. 2).

The formation of nanogels Pox(mDOPA)/PAH was first performed by the slow addition of a solution of PAH to an aqueous solution of Pox(mDOPA) at room temperature.

Weight ratios and addition modes of the two partners were controlled to form stable dispersions of nanogels (Pox(mDOPA)/PAH). For that purpose, the slow addition of PAH to an aqueous solution of Pox(mDOPA) resulted in the spontaneous formation of a stable and clear light brown solution of cross-linked nanogels at room temperature. The presence of the nanogels was confirmed by transmission electron microscopy (TEM) performed after lyophilisation that showed nanogels with a diameter ranging from 100 to 200 nm (FIG. 3b). It is important to note that the nanogels solution had to be lyophilized on the TEM grid prior to analysis. If the solution was simply dropped onto the grid and slowly dried at room temperature under atmospheric conditions, nanogels strongly aggregated (FIG. 3a).

Analysis by dynamic light scattering (DLS) without filtration showed nanogels agglomeration with an average hydrodynamic diameter equal to 130 nm with a rather high polydispersity (PDI=0.2) (FIG. 4). The nanogel solutions were stable for at least one month when stored at room temperature and at pH around 10 without stirring. The solution remained clear without any precipitation and the hydrodynamic diameter distribution obtained by DLS remained almost unchanged after one month of storage.

The ability of the nanogels to be loaded with and deliver multiple drugs was further explored. Different bioactive agents were incorporated through the combination of covalent conjugation, electrostatic and hydrophobic interactions as well as hydrogen-bond formation. Covalent conjugation was carried out by exploiting the reactivity of quinone groups of Pox(mDOPA) towards amine function. For that purpose, Vancomycin (V), a glycopeptide antibiotic that contains primary amine in its sequence, was used for the conjugation, and physical entrapment was employed for the incorporation of Minocycline (M), a tetracyclin-class antibiotic, and ticagrelor (T), an antiplatelet agent with antithrombotic properties.

Pox(mDOPA)-VMT/PAH) were then prepared in a similar way by the addition of a PAH solution to an aqueous solution of VMT loaded Pox(mDOPA), resulting in the appearance of a yellow-brown suspension. DLS measurement without filtration evidenced the presence of nanogels with an average hydrodynamic diameter of 200 nm slightly higher than the previous one due probably to the presence of VMT (bio)molecules (FIG. 5).

All synthetic steps are performed in mild conditions and in aqueous media, which make the building-block synthesis pathways relevant for the development of an environment-safe process.

Oxidation of P(mDOPA) in Basic Medium:

Oxidation was carried out according to a previous study (Faure et al., Biofouling. 2012: 28(7):719-28). P(mDOPA) (20 mg) were dissolved in distilled water (20 mL) and a NaOH solution (0.1 M) was slowly added in order to raise the pH above 10. This oxidation step lasted at least one night under air.

Preparation of Pox(mDOPA)/PAH Cross-Linked Nanogels was as follows:

Nanogel Preparation:

P(mDOPA) (2.5 mg) was dissolved in distilled water (5 mL) and NaOH (0.1 M) was slowly added in order to raise the pH above 10 and to promote the oxidation of catechol groups of P(mDOPA). After one night at room temperature, an aqueous solution of PAH (0.5 mL; 0.5 g/L) at pH 10 was slowly added to the solution of Pox(mDOPA) under vigorous stirring. The solution was lead to react for one hour at room temperature under vigorous stirring. Nanogels with a diameter ranging from 150 nm to 250 nm were observed by DLS.

Nanogel Antibiotics (ABTs) Preparation:

The procedure is identical as the one described above except that Pox(mDOPA) was solubilized in the presence of ABTs (Minocycline and Vancomycine) to increase the interaction between polymer chains and drugs. After 1 h at 6° C., an aqueous solution of PAH (0.5 mL; 0.5 g/L) at pH 10 was slowly added to the solution of Pox(mDOPA) under vigorous stirring. The solution was lead to react for one night at 6° C. under vigorous stirring before nanogel deposition. The final concentration of the ABTs in the nanogels solution was 0.5 mg/ml.

Nanogel Ticagrelor (T) Preparation:

The procedure is identical as the one described above except that Pox(mDOPA) was solubilized in the presence of 1 ml of Ticagrelor solution (1 mg/ml in DMSO) to increase the interaction between polymer chains and drugs. After 1 h at 6° C., an aqueous solution of PAH (0.5 mL; 0.5 g/L) at pH 10 was slowly added to the solution of Pox(mDOPA)/T under vigorous stirring. The solution was lead to react for one night at 6° C. under vigorous stirring before nanogel deposition.

Example 2. Nanogel Immobilization on Titanium Substrate Using Polydopamine Coating A first strategy consisted of a first immersion of the substrate in a Tris buffer solution of DOPA to strongly anchor the first layer to the surface by DOPA/metal interactions (FIG. 6). The next layers were then built by the successive dipping of the surface into an aqueous solution of a polymer bearing primary amines, polyallylamine (PAH), and then in a solution of a P(mDOPA) based nanogel. Poly(methacrylamide) bearing oxidized DOPA moieties on each monomer unit (FIG. 1, formula (2)). (Pox(mDOPA)) were used in combination with PAH to prepare stable solutions of nanogels in water at room temperature that can be easily deposited to titanium (Ti) surface.

Polydopamine Coating

Polydopamine (PDOPA) has been used to modify bio-inert surfaces because it can adhere on various material surfaces. Dopamine molecules have 3,4-dihydroxy-1-phenylalanine-lysine motif, which can polymerize to form PDOPA layers on material surfaces at mild conditions. Incorporating PDOPA as primer films provides an alternative route to functionalize those biomaterials with non-fouling surfaces, and can further enhance their desirable biological, chemical, and therapeutic properties for biomedical applications.

Dopamine (2 mg/mL) was dissolved in 10 mM Tris-HCl (pH 8.5), and substrates were dipped into the solution. pH-induced oxidation changes the solution colour to dark brown, resulted in spontaneous deposition of a thin adherent polymer film (FIG. 7). To avoid the microparticle deposition lower dopamine concentration can be used 0.125 mg/ml and/or vertical sample orientation were necessary. The coated surfaces were rinsed with ultrapure water and dried by N2 gas before storage or treated as described below for ad-layer formation.

Polydopamine-Assisted Self-Assembled PAH Monolayer

After modification of titanium surface using PDOPA as first layer, covalent grafting of PAH occur through amine/quinone reaction and/or Schiff base formation at room temperature, and consequently for the interlayer cross-linking (Scheme 1). Importantly, the next solution of PAH was deposited at pH above 10 in order to obtain the polymer in the deprotonated state. The reaction between primary amines and the quinone groups of Pox(mDOPA) was therefore made possible. In acidic media, amine groups were protonated and did not react with Pox(mDOPA), such that cross-linking and growth of the film cannot occur. For PAH ad-layer formation, 1 mg/ml of PAH solution was dissolved in ultrapure water which was equilibrated at pH above 10 by adding 0.1M NaOH solution. Polydopmaine-coated substrates were subsequently immersed in the solution. After 4 hrs or more (typically overnight reaction for 18 hrs), the substrates were rinsed by ultrapure water.

Contact angles were measured on a dry titanium surface after dropping 10 µL of ultrapure water. The static contact angles on the pure titanium and polydopamine-coated titanium surfaces were 85°±2° and 47±6°, respectively proving the modification of the surface.

Nanogel Assembly

Covalent grafting of nanogels was performed through the same reaction and/or Schiff base formation between primary amines of PAH monolayer and the quinone groups of Pox(mDOPA) in nanogel. The surface coated by a layer of the PDOPA, and a layer of PAH was then incubated with the aqueous solutions of the nanogels Pox(mDOPA)/PAH following the protocol described below. Contact angles were measured on a modified titanium surface with PAH and nanogel. The contact angle of the PAH was about 65°; its amplitude was higher than of the one measured on polydopamine-coated surface, probably due to the presence of non-polar amine group. After deposition of nanogel presenting the same catechol groups as polydopamine, the contact angle decreased to about 42°.

PEG Grafting Monolayer

Poly(ethylene glycol) (PEG) is one of the most commonly used synthetic polymer to impart protein resistance to a surface. Several strategies to modify substrates with that kind of polymers can be found in the literature such as electrografting, self-assembled monolayers (SAMs), copolymers adsorption to cite only a few. The PEG grafting was carried out by exploiting the reactivity of quinone groups of Pox(mDOPA) towards thiols. For that purpose, thiol end-functionalized PEG (PEG-SH) were considered for the conjugation. This thiol-based strategy allows specific grafting under mild conditions and without pH constrain in contrast to the amino-based strategy that requires pH≥10. For PEG grafting, 5 mg/mL of methoxy-poly(ethylene glycol)-thiol (mPEG-SH, 1.5 kDa) was dissolved in 10 mM Tris pH 8.0. The buffer used for mPEG-SH was vacuum degassed for ~1 hr to prevent oxidation (—S—S—) between thiol groups. PEG was reacted into the PDOPA layer (nanogel layer) through Michael-type addition and Schiff base reactions to inhibit non-specific interactions and increase hydrophilicity in physiological conditions. The water contact angles verified the anchoring of PEO chains to modified Ti surfaces. Surprisingly a PEO layer exhibiting contact angle of 43°±1 was found.

Briefly, nanogel deposition using PDOPA as first layer was conducted at room temperature in five steps:

Step 1: Ti discs (1 cm diameter) were sonicated in tetrahydrofuran (THF), acetone, ethanol, and water, 10 min for each step.

Step 2: Ti were immediately dipped into the DOPA Tris buffer solution (0.125 g L$^{-1}$) for 18 h.

step 3: After rinsing twice with 5 ml water, the modified substrates were dipped into a solution of PAH (pH>10) for 18 h and rinsed twice with 5 ml water.

step 4: After rinsing twice with 5 ml water, the modified substrates were dipped into a solution of nanogels (loaded with ABTs and T) for 18 h and rinsed twice with 5 ml water.

step 5: After rinsing twice with 5 ml water, the modified substrates were dipped into a solution of PEG-SH for 1 h and rinsed twice with 5 ml water.

The surface morphology is an important parameter for biomedical devices that may affect the interface energy and also the interaction between the bio-components and the material surfaces. To gain further information and understand the microstructures of the nanogel coated Ti surfaces, field emission scanning electron microscopy (SEM) observations were carried out (FIG. 8). The pristine Ti surface exhibited a relatively smooth morphology (left panels). In contrast, after nanogel deposition, numerous well-distributed nanogels were observed, ranging in size from 80 nm to 120 nm (right panels). The results indicated that the size of deposited nanogels, corroborate the sizes of nanogels measured by TEM in solution (FIG. 2b).

Layer-by-Layer (LbL) Assembly

LbL deposition was conducted in the same conditions, using similar procedure as the one described above except that steps 2 to 4 were repeated five times to obtain five layers.

Quartz Crystal Microbalance

As a first evidence of the multilayer film build-up, Quartz Crystal Microbalance coupled with Dissipation (QCM-D) was used to follow the film growth in real time on gold sensors by measuring the variation of the resonant frequency ($\Delta f$) vs. time. A decrease in $\Delta f$ indicates polymer deposition. FIG. 9 shows that all components were successfully deposited according to the selected deposition protocol and redox/pH conditions and remain on the substrate even after rinsing with water.

First, a tris buffer solution of DOPA (0.125 g/L) was flowed through the cell at room temperature, leading to the first anchoring layer. The f shift continued to decrease, until the DOPA was rinsed from the sample chamber. Second, a solution of PAH (pH>10) was injected leading to an immediate negative shift was observed indicating an increase in mass at the interface, as the polymer adsorbed to the gold surface. After removing the excess unbounded polymer by rinsing with water, a stable baseline was attained during the rinsing step, demonstrating that the polymer ad-layer strongly tethered onto the surface. Once the reversibly adsorbed polymer was removed in the rinsing step, nanogel solution in milli-Q water (pH ☐10) was introduced into the sensor chamber, at the same flow rate and temperature. The deposition of the nanogel solution was observed by the important decrease of the frequency vibration. Importantly, this layer of nanogels was stable since it cannot be removed after rinsing with water. In the last step, irreversibly bound polymer can be seen from the raw $\Delta f$ after injection of PEG-SH solution due to the reaction of thiol function with residual quinone groups present in the nanogels (FIG. 9).

Example 3. Direct Nanogel Immobilization on Titanium Substrate

In a second approach, titanium surface was directly immersed in the nanogel solution to obtain nanogel-modified surface without the need of a primer coating. In this case, the assembly mechanism is based on the adhesive property of the catechol and quinone group present in the surface of the nanogel (FIG. 10).

Using SEM analysis, the formation of a monolayer of nanogels Pox(mDOPA)/PAH on Ti was observed (FIG. 11). Estimated diameters of the nanogels were found to vary between 80 nm to 120 nm.

Example 4: Immobilization of Nanogels onto Valve Bioprosthesis

The same approach reported above was used to modify a biological valve. Respecting the same steps, biological valves were first immersed in a Tris buffer solution of DOPA (10 mM Tris-HCl (pH 8.5)) to strongly anchor the first layer of polydopamine. The implant became dark brown as a result of deposition of a thin adherent PDOPA film (FIG. 12).

The next layers were then built by successive dipping of the valve into an aqueous solution of a polyallylamine (PAH), and then in a solution of a P(mDOPA) based nanogel.

The following steps were conducted at room temperature:
Step 1: Biological discs (1 cm diameter) were dipped three times in 10 ml of water, for 10 min.
Step 2: Biological discs were immediately dipped into the DOPA Tris buffer solution (0.125 g $L^{-1}$) for 18 h.
Step 3: After rinsing twice with 5 ml water, the modified tissue was dipped into a solution of PAH (pH>10) for 18 h and rinsed twice with 5 ml water.
Step 4: After rinsing twice with 5 ml water, the modified tissue was dipped into a solution of nanogel for 18 h and rinsed twice with 5 ml water.
Step 5: After rinsing twice with 5 ml water, the modified tissue was dipped into a solution of PEG-SH for 1 h and rinsed twice with 5 ml water.

Scanning electron microscopy SEM was used to analyse the surface morphology of modified biological tissue. It was observed that the surface of biological tissue before modification exhibited a relatively smooth and ordered collagen nanofibers. After nanogel deposition, collagen fibers appeared more compact (FIG. 13), and well-distributed nanogels were observed on the surface of collagen fibers (FIG. 14). The PDOPA primer coating augmented nanogel deposition.

Film growths (PDOPA and nanogels) were followed in real time using quartz crystal microbalance coupled with dissipation technique (QCM-D). A Q-Sense E4 was used in this study. The stainless steel-coated AT-cut resonator (fundamental frequency: 5 MHz) was used as received. First, distilled water was introduced in the cell and the flow was maintained until a stable baseline was obtained. LbL deposition was then initiated by switching the liquid exposed to the crystal from distilled water to the DOPA solution 0.125 g $L^{-1}$ with 0.15 M NaCl at a flow rate of 200 µL min$^{-1}$, temperature of 25° C. After 10 min, the substrate was rinsed by distilled water to remove the excess of unbounded DOPA. Then, the alternative deposition of PAH (1 g $L^{-1}$) and nanogels solutions was carried out (about 10 min for each step) with rinsing steps with distilled water between each layer. PEG-SH solution was finally introduced in the system as the last layer and further rinsed when a stable signal is obtained.

A Delsa Nano-C Particle Analizer (Beckman Coulter) equipped with a laser diode source (wavelength 658 nm; power 30 mW) was used for measuring the hydrodynamic diameter of the aqueous nanogels solutions. Scattering data were collected for at least 50 individual measurements at a constant scattering angle and averaged for each sample. The obtained scattering data were fitted using a volume-weighted cumulative analysis to estimate the diffusion coefficient of the nanogels in solution. The hydrodynamic diameter of the samples (DH) was obtained using Stokes-Einstein relationship.

The samples for scanning electron microscopy (SEM) were analysed by Field Emission Gun Scanning Electron Microscope (FEG-SEM) MEB ULTRA55 operating at 3 kV was used for sample observation after a thin layer (10 nm) of Au—Pd to increase the contrast.

Synthesis of N-methacryloyl 3,4-dihydroxy-L-phenylalanine methyl ester DOPA methyl ester hydrochloride (9 g, 0.0363 mol) in dry CH2C12 (350 mL) was added to a two-necked round-bottomed flask equipped with a dropping funnel and a magnetic stirrer, and placed under nitrogen. Freshly distilled Et3N (17.7 mL, 0.127 mol) was then added, and the flask was cooled to OC. A solution of methacryloyl chloride (3.51 mL, 0.0363 mol) in CH2C12 (70 mL) was added dropwise through a dropping funnel with vigorous stirring under nitrogen. The final mixture was maintained under stirring at room temperature for 48 h. After reaction, the triethylammonium chloride, formed as a by-product, was removed by filtration and the excess of reagents was removed under reduced pressure. The product was recovered as a sticky solid with a yield of 90%.

P(mDOPA) Synthesis

Prior to polymerization, the catechol group of the mDOPA must be protected in order to avoid side reactions during the radical polymerization from its —OH groups. 2 g of mDOPA with protected catechol groups (see below for the protection step) (2.6 mmoL) were placed under nitrogen in a one-necked round-bottomed flask equipped with a magnetic stirrer. At the same time, 19 mg (0.067 mmoL) of V501 initiator was dissolved in 7 mL of distilled water. The pH solution was adjusted above 9 with $Na_2CO_3$ until complete dissolution of the white powder. The solution was then degassed by bubbling nitrogen through it for 15 minutes. Then, the aqueous solutions of the V501 initiator was transferred with a capillary under nitrogen in the glass flask containing protected mDOPA. The reactor was heated in an oil bath thermostated at 70° C. during 24 hours. Then, catechol groups were deprotected by adjusting the pH around 2 with concentrated HCl. The resulting mixture was dialyzed (membrane porosity 1000 Da) against water during 48 hours, followed by lyophilization. The copolymer was recovered as a white powder with a 88% yield.

Synthesis of α-methoxy-ω-mercapto-poly(ethylene oxide) (MPEG-SH)

a-Methoxy-x-mercapto-poly(ethylene oxide) (MPEG-SH) was synthesized by esterification of the hydroxyl end-group of the monomethoxy poly(ethylene oxide) (MPEG-OH) (Mn=1500 g/moL) with mercaptoacetic acid. A typical reaction was carried out as follows. MPEG-OH (10 g; 5 mmoL) was added into a 100 ml two-necked flask equipped with a stirrer and a Dean-Stark device. The MPEG-OH was dried by three azeotropic distillations with toluene and finally dissolved in 50 ml of toluene. Mercaptoacetic acid (3.5 ml, 50 mmoL) and concentrated sulfuric acid (two drops) were then added. The flask was heated in an oil bath at 110° C. overnight. MPEG-SH was collected by precipitation in ether at 0° C. and then dried at 40° C. under vacuum for 24 h.

Example 5: Anti-Thrombotic Properties of Bioactive Nanogels

Dynamic Impact-R Test

To study blood-material interaction in dynamic conditions, the Impact-R apparatus was used. This is a close-to-physiological in vitro system mimicking the laminar flow of the blood in circulation and is used to study platelets function and thrombus formation under flow. The laminar flow created by the rotation at constant speed of a piston (the bell and the cone) on a thin blood layer deposited on a well, activates platelets by shear stress, platelets adhere on the polystyrene surface of the well and then are stained with May-Grünwald stain. The system allows variation of the speed: the higher the speed—corresponding to higher heart rate—the more thrombi form on the surface.

By inspection of the polystyrene surface at an optical microscope and by image analysis, it is possible to obtain two parameters: the percentage of surface covered by platelets aggregates (SC, %), and the average size of the aggregates (thrombi) (AS, $\mu m^2$).

The test was performed on citrated blood of healthy donors. The SC and AS obtained were proportional to the speed rotation of the cone at a specific well radius (speed increases with radius).

The effect of different polymer coatings at different time points was tested (FIG. 15). The polymers (PEG and reticulated PEG, APEG) were covalently bound to a thin polydopamine layer, DOPA, which was also tested alone, and which had a slight, but not significant, effect on the reduction of platelet activation and adherence. Increasing the time of shear stress applied to the blood, the two parameters SC and AS increased significantly. A significant difference was found at all time points between non-coated (NC) and PEG-coated surface for both SC and AS parameters.

The following coatings were then tested, Polydopamine (DOPA), DOPA-PEG (PEG), DOPA-Nanogel (NGEL) and DOPA-Nanogel-PEG (NGEL-PEG) on 3 healthy donors in vitro at the Impact-R using 1800 $s^{-1}$ shear stress for 2 min (FIG. 16A,B). Significant differences in SC values were observed for all coatings compared to NC, except for DOPA. PEG-coated PS wells gave the lowest SC and AS values. Platelets could not form aggregates on PEG-coated surface. Importantly, nanogel deposition did not show platelet adhesive properties.

The test in FIG. 17 was performed to study the effect of ticagrelor alone (NG-T-PEG) or in combination with the two antibiotics (NG-TA-PEG) on flow-induced platelet consumption. A test on a blood sample from one donor was carried out at 1800 s–$^1$ for 4 min. Binding of platelets was not observed for any conditions except for the non-coated (NC) wells. The values reported in FIG. 17 represent single platelet count in the blood after the test, and thus depict platelet aggregate formation on the surface and/or in blood. A significant increase in platelet count was observed for both nanogels, indicating that platelets remained in suspension as single platelets (i.e. non activated) and did not adhere to the surface.

Static Test

The hemocompatibility of the coating in static conditions (no shear stress applied) was studied. Static test was performed by incubating 500 μL of fresh blood under gentle agitation (60 rpm) for 2 h at 37° C. and 5% $CO_2$ in a 24-well non-treated plate and observing cell adherence at the optical microscope in presence or absence of the coating. Cells were stained using Crystal Violet dye. In FIG. 18 optical microscope images of cells stained with crystal violet highlighted inhibition of blood cell adhesion after PS surface modification. Conditions were: Non Coated (NC), Nanogel (NG), Nanogel Peg (NP) and Nanogel antibiotics Peg (NAP) bound to a polydopamine layer.

A platelet suspension (PRP: platelet rich plasma) was also incubated with NAP-coated PS wells for 1 min (FIG. 19A) or for 45 min (FIG. 19B). A clear difference was observed in surface coverage compared to NC-PS well. NC-1 min: 90% surface coverage (SC); NAP-1 min: 5% SC; NC-45 min: 99.5% SC; NAP-45 min: 40% SC. Thus, all these data indicate that surface modification with the nanogel preparation of the present invention does not activate platelets under static and dynamic conditions.

Example 6: Anti-Biofilm Properties of Bioactive Nanogels: *Staphylococcus* (*S*) *Aureus*

Biofilms of *S. aureus* grown for 24 h in a 24-well plate under static conditions were analyzed by crystal violet staining (FIG. 20). A reduction in biofilm was observed when nanogels were loaded with minocycline. In contrast, covalently bound vancomycin does not reduce biofilm formation. Accordingly, the Ng-Mino-Peg condition led to a 95% reduction in planktonic bacteria compared to all other conditions.

In the case of biological valve disks incubated in static condition with *S. aureus* for 24 h in a 24-well plate, planktonic bacteria were completely killed when incubated with Ng-ABsPeg modified disk, while viable bacteria were present in the non-coated disk condition.

Interestingly, SEM analysis of biological valve surface modified with vancomycin, minocyclin, and ticagrelor-loaded nanogels did not detect any bacteria, while non-modified surface revealed large biofilms (FIG. 21). Thus, the bioactive nanogel of the present invention confers potent anti-biofilm properties to biological valves.

Example 8: Anti-Biofilm Properties of Bioactive Nanogels: *Enterococcus* (*E*) *faecalis*

FIG. 22 shows the effect of PS surface modification on *E. faecalis* biofilm formation. Antibacterial activity was observed by assessing viability of bacteria in suspension. Vancomycin-loaded nanogels presented antibacterial activity under static conditions, demonstrating that covalent binding of the antibiotic in nanogels preserved its activity. Minocyclin was effective in both shaking and static conditions.

Example 9: Defining the Optimal Ratio of Minocycline and Ticagrelor to Create a Nanoreservoir with Anti-Thrombotic Properties In order to produce a nanoreservoir with both antibacterial and antiplatelet activity that would exhibit optimal anti-thrombotic properties, the optimal concentration of the antiplatelet drug ticagrelor was first determined. For this purpose, 1 ml of nanogel suspensions loaded with increasing concentrations of ticagrelor was centrifuged at 12000 g for 15 minutes, washed 2 times in PBS and resuspended in 300 μL of PBS. 260 μL of platelet-rich-plasma (PRP) was incubated with 10 μL of purified nanogel suspensions for 10 min. Platelet aggregation was then induced by adding 10 μM ADP at 37° C. under stirring conditions. The efficacy of the nanogel suspensions to inhibit the ADP-induced platelet aggregation was compared to that of the IC50 concentration of free ticagrelor. It was observed that nanogels loaded with 112 µg/mL ticagrelor were as potent as ticagrelor 1.8 µg/mL to inhibit platelet aggregation (FIG. 23A). This loading concentration was used for subsequent studies.

It was identified that the antiplatelet nanogels (loaded with 112 µg/mL ticagrelor) formed more easily in the absence of minocycline. Therefore, a strategy was adopted in which the two nanogel solutions were mixed in a x/y ratio to obtain a nanoreservoir containing minocycline and ticagrelor. A ratio of x (minocycline)/y (ticagrelor) between 1/5 and 2/3 provided optimal inhibition of ADP-induced platelet aggregation (FIG. 23B). Furthermore, immobilization of the nanogel mixture prepared in a 2/3 ratio on a polystyrene surface did not activate coagulation of human plasma as compared to non-coated surface (FIG. 24).

Example 10: Multilayer Assembly of Nanogels Improves the Nanoreservoir Anti-Biofilm and Anti-Thrombotic Efficacy It was then assessed whether multilayer assembly could improve the antibacterial and antiplatelet efficacy of the nanoreservoir. One, three, or five layer-by-layer nanogels were immobilized on polystyrene or titanium surfaces. Surfaces were then incubated with *S. aureus*, and biofilm formation was quantified as described in Methods. It was found that increasing the number of nanogel layers augmented the nanoreservoir anti-biofilm action (FIG. 25).

In order to study the antiplatelet effect of immobilized multilayer nanoreservoirs, a test using the Impact R apparatus (see Methods) was set up. Whole blood was pre-activated or not with 2.8 µM ADP for 1 min at RT under gentle agitation before applying a rotation of 720 rpm for 4 min. Surface coverage and aggregate size were determined on each tested surface, and the drop of platelet count was analysed in supernatant. It was anticipated that ticagrelor released from the nanoreservoir can revert ADP effect since it has a higher affinity for the platelet P2Y12 receptor.

The effect of 1 layer ticagrelor/minocyline-loaded nanogel was compared with 5-layer loaded nanogels (FIG. 26). Non coated surface and surface coated with non-loaded nanogels were also included. Pre-activation with ADP induced the formation of micro-aggregates in solution, which resulted in reduced surface coverage (FIG. 26A), slightly increased aggregate size (FIG. 26B), and translated into a loss of single platelets (FIG. 26C) as compared to non-activated blood upon incubation on non-coated surface (NC) or on surface coated with non-loaded nanogel (NG). Blood incubation on surface coated with loaded nanogels inhibited the effect of ADP, as a result of ticagrelor release from the nanoreservoir. The efficacy of the 5-layer nanoreservoir was superior to that of the 1-layer one in terms of surface coverage and aggregate size. Both nanoreservoirs recovered the ADP-induced loss of single platelets in solution.

Example 11: Reticulation of Multilayer Nanogel Assembly Delays Bioactive Molecule Release and Prolongs Efficacy The release of the bioactive molecules was observed to slow down by reticulating the 5-layer nanogel assembly with dopamine at the last step of nanoreservoir formation. By adjusting the crosslinking density of the nanogel coating, the diffusion rate of the loaded molecules can indeed be tuned. Dopamine acts as crosslinking agent to slow down the diffusion of bioactive molecules from nanoreservoirs. This dopamine treatment can affect the diffusion of the molecules in two different ways. First, dopamine can penetrate within the different layers of the LBL nanogel assembly, react with the nanogels, and thereby increase their cross-linking density. Second, dopamine can polymerize in the solution and deposit by precipitation as a thin layer on top of the surface of the LBL, and act as an additional barrier to the diffusion of the bioactive molecules.

After the deposition steps of the different layers, the resulting LBL assembly was dipped in 0.125 mg/ml dopamine solution during one hour. The surface was washed before grafting PEG 1500 onto the surface. Coated and non-coated surfaces were incubated with medium alone for 48 h. The medium was changed twice before the bacteria were allowed to adhere as previously described. FIG. 27A shows that non-reticulated nanoreservoir loaded with minocycline and vancomycin (NTMV) could not inhibit *S. aureus* biofilm formation, while reticulated nanoreservoir (D-NTMV) was still active after 48 h. FIG. 27B depicts the antibacterial effect of medium removed after the second 24 h of contact with the two nanoreservoirs, demonstrating the release of higher concentration of antibiotics from reticulated nanoreservoir during this contact period.

Example 12: In Vivo Demonstration of Antibacterial Efficacy of Nanoreservoir Immobilized on Ti Implants In order to demonstrate the anti-biofilm efficacy of the nanoreservoir in vivo, a mouse model of titanium implant *S. aureus* infection was used. Pre-infected titanium devices were implanted subcutaneously and in vivo biofilm formation was assessed after 4 h. FIG. 28A shows the number of CFU per explanted titanium disk after correcting for the initial CFU per disk at the time of implantation. The nanoreservoir fully prevented biofilm formation on titanium implants as compared to non-loaded nanogels. This result was further confirmed by scanning electron microscopy of titanium implants (FIG. 28B). Bacteria were visible on titanium coated with non-loaded nanogels only. Immune cells were observed on nanoreservoir-coated implants.

Example 13: Preparation of LBL Assembled Cross-Linked Nanogels Covered by Different Thiol or Vinyl End Functionalized Ligands In order to identify a nanogel formulation that would exert intrinsic anti-adhesive properties against platelets and bacteria, different thiol or vinyl end functionalized ligands were added as the last layer of LBL assembled nanogels.

α-methoxy-ω-mercapto-poly(ethylene oxide) (MPEG-SH), referred to as PEG1.5, was synthetized by esterification of the hydroxyl end-group of the monomethoxy poly(ethylene oxide) (MPEG-OH) (Mn=1500 g/mol) with mercaptoacetic acid as follows:

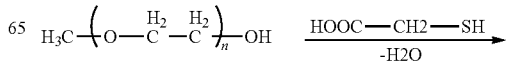

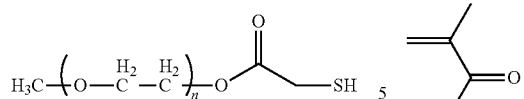

MPEG-OH (10 g; 5 mmol) was added into a 100 ml two-necked flask equipped with a stirrer and a Dean-Stark device. The MPEG-OH was dried by three azeotropic distillations with toluene and finally dissolved in 50 ml of toluene. Mercaptoacetic acid (3.5 ml, 50 mmol) and concentrated sulfuric acid (two drops) were then added. The flask was heated in an oil bath at 110° C. overnight. MPEG-SH was collected by precipitation in ether at 0° C. and then dried at 40° C. under vacuum for 24 h. PEG-SH was characterized by 1H NMR (FIG. 29).

PEG2 (Methoxy-PEG-(CH2)2-SH, Mw 2,000, Chemical Name: α-Mercaptoethyl-ω-methoxy, polyoxyethylene, ref. SUNBRIGHT® ME-020SH), PEGS (Methoxy-PEG-(CH2) 2-SH, Mw 5,000, Chemical Name: α-Mercaptoethyl-ω-methoxy, polyoxyethylene, ref. SUNBRIGHT® ME-050SH), and PEG10 (Methoxy-PEG-(CH2)2-SH, Mn 10,000, Chemical Name: α-Mercaptoethyl-ω-methoxy, polyoxyethylene, ref. SUNBRIGHT® ME-100SH) were obtained from NOF corporation.

The chemical formula of MPEG-SH from NOF corporation is:

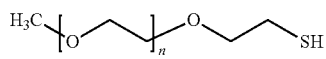

The following vinyl end functionalized PEG ligands (PEG-Acrylate) were used: Polyethylene glycol methyl ether acrylate, Mn 480, Sigma-Aldrich, ref. 454990 (APEG0.5), Polyethylene glycol methyl ether acrylate, Mn 1,000, Alfa Aezar. ref. 46537 (APEG1). Their chemical formula is:

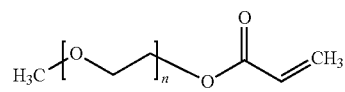

Synthesis method of polybetaines is illustrated below. Polymerization of 2-(Methacryloyloxy) ethyl Phosphorylcholine (MPC) was achieved by adding MPC (0.5 g, 1.7 mmol), 4-cyanopentanoic acid dithiobenzoate (CTP; 10 mg, 0.05 mmol), AIBN (1.2 mg, 7.3×10-3 mmol), and deionized H2O:MeOH 3:1 (5.0 ml) in a Schlenk flask equipped with a magnetic stir bar. The mixture was then stirred in an ice-bath to ensure complete dissolution of CTP and AIBN. The solution was then purged with nitrogen prior to immersion in a preheated oil-bath at 70° C. After 12 h, the polymerization was stopped via rapid cooling and exposure to air. The polymerization solution was then dialyzed against deionized water for 12 h with 3 changes of the deionized water. Homopolymer was then recovered by freeze-drying. Polybetaines were characterized by 1H NMR (FIG. 30).

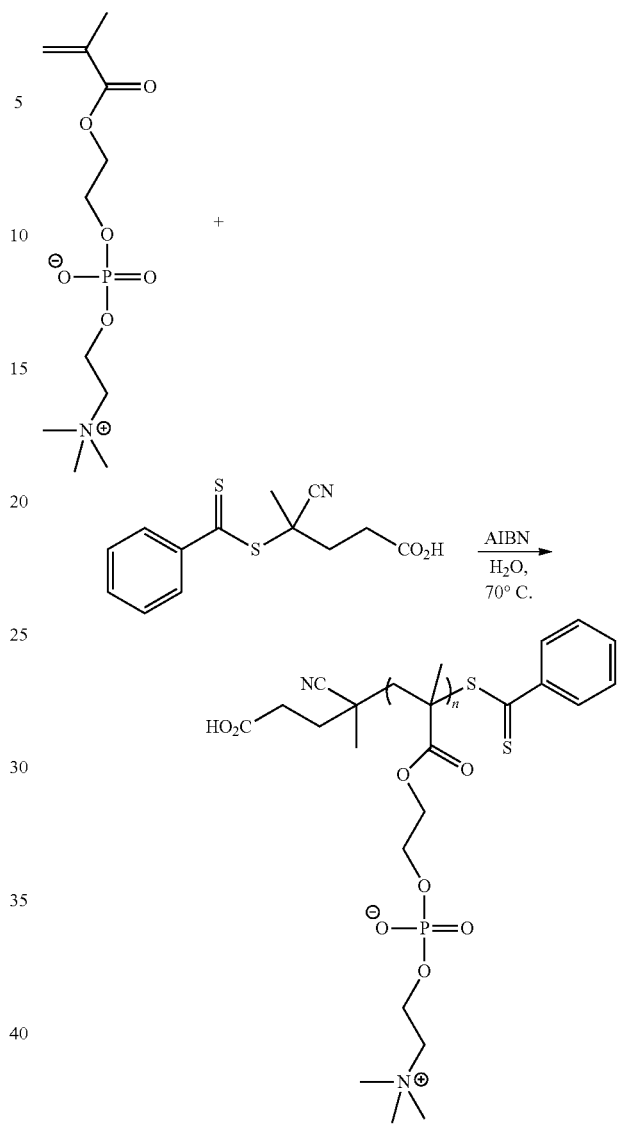

Stable solutions of nanogels in water were prepared by adequately controlling both the redox state of the P(mDOPA) polymer and the pH of the PAH solutions. First, P(mDOPA) is oxidized in aqueous media under basic conditions for 12 h to form the hydrosoluble Pox(mDOPA). Oxidized DOPA moieties of Pox(mDOPA) are necessary for the covalent interaction of PAH through amine/quinone reaction and/or Schiff base formation at room temperature, and consequently for the preparation of stable cross-linked nanogels.

Immobilisation of cross-linked nanogels on a surface of a substrate was achieved by a first immersion/dipping of the substrate in a Tris buffer solution of DOPA to strongly anchor the first layer to the surface. The next layers are then built by the successive dipping of the surface into an aqueous solution of a polymer bearing primary amines, polyallylamine (PAH), and then in a solution of nanogel followed by two washes with deionized water. The layer-by-layer (LBL) assembly was obtained by repeating the above deposition and washing steps. Solutions of thiol and vinyl end functionalized ligands (5 mg/ml in 10 mM Tris pH 8.0) were then added as a last layer by exploiting the reactivity of quinone groups of Pox(mDOPA) towards thiols, and through Michael-type addition and Schiff base reactions with amine group of PAH, respectively.

The table below shows contact angles measured on a surface coated with nanogels bearing different ligands with thiol or vinyl functionalized ends, as compared to polydopamine.

| COATING | | | | | | | |
|---|---|---|---|---|---|---|---|
| | PDOPA | PEG1kD | PEG2kD | PEG5kD | APEG0.5kD | APEG1kD | PMPC15kD |
| Contact angle (°) | 60 | 40 | 38 | 37 | 55 | 42 | 35 |

PDOPA: polydopamine;
PEG: PEG-SH;
APEG: PEG-acrylate;
PMPC: polybetaine

In the following examples, the anti-adhesive (plasma proteins, platelets and bacteria) properties of surface immobilized 5-layer nanogels grafted with the different ligands as last layer were tested. The effect on the activation of the contact phase of coagulation was also studied.

Example 14: Ligands with Thiol Functionalized Ends are Superior to Those with Vinyl Functionalized Ends to Prevent Platelet Adhesion on Immobilized Nanoreservoirs LDH activity assays were performed in order to compare platelet adhesion on polystyrene surface coated or not with 5-layer nanogels or nanoreservoirs bearing a top layer of PEG with thiol or vinyl functionalized ends (FIG. 31). After 45 min incubation of PRP on the surfaces, it was observed that nanoreservoirs made of minocycline- and ticagrelor-loaded PEG-SH nanogels (in a ratio of 2/3, see above) efficiently inhibited platelet adhesion as compared to non-loaded nanogels, while the same nanoreservoirs made of nanogels bearing PEG-acrylate were less efficient.

Example 15: Superiority of PEG2000 Ligand with Thiol Functionalized Ends to Prevent S. aureus Biofilm Formation on Nanogel-Coated Titanium Implants To determine if ligand grafting onto nanogels could confer by themselves anti-adhesive properties to surfaces, S. aureus biofilm formation was compared on medical grade titanium implants were coated or not with 5-layer nanogels bearing different ligands with thiol or vinyl functionalized ends. Biofilm formation was evaluated by detaching and plating bacteria that adhered after 3 h on the implants. CFU counts were then determined. It appeared that the thiol end PEG2000 ligand could confer the most efficient anti-biofilm property to titanium as compared to polybetaine 15000 and PEG-acrylate 500 and 1000 (FIG. 32).

Example 16: PEG Ligands with Thiol Functionalized Ends: Effect of Molecular Weight on Bacteria Adhesion Further comparisons of S. aureus anti-biofilm efficacy of nanogels bearing PEG thiol of higher molecular weight than 2000 were made. FIG. 33 indicates that the anti-biofilm effect of PEG thiol-nanogels increases with PEG molecular weight.

Example 17: PEG Ligands with Thiol Functionalized Ends: Effect of Molecular Weight on Platelet Adhesion Under Flow With the aim to create a surface with both anti-biofilm and antiplatelet properties, experiments were conducted of platelet adhesion under flow using the Impact-R system, the same PEG thiol ligands as in example 16 (FIG. 34) were compared. In contrast to biofilm formation, the results indicate that nanogels without grafted polymers already conferred antiplatelet effect to surfaces, as shown by reduced percentages of surface coverage by platelets and reduced aggregate size as compared to non-coated surface. Differences were also observed between anti-biofilm and antiplatelet effects in terms of PEG thiol molecular weights. Indeed, the optimal antiplatelet coating was achieved by using PEG 1500 or PEG 2000, while increasing molecular weight did not improve the effect.

Example 18: PEG Ligands with Thiol Functionalized Ends: Effect of Molecular Weight on Coagulation Clotting time of plasma that has been in contact with coated and non-coated surfaces was compared. The reference was the plasma in basal state, i.e. plasma that has not been in contact with the surface (except the surface of the tube and tips) (FIG. 35). FIG. 35 shows a shortening of clotting time obtained when negatively charged kaolin is immobilized on the surface, and the opposite effect of the FXIIa inhibitor CTI. It was observed that surfaces coated with 5-layer nanogels bearing PEG ligands slightly prolonged clotting times as compared to non-coated surface. When comparing PEG of different molecular weights, it was observed that the longest clotting times were produced by nanogels bearing PEG 2000 and 5000. Thus, although not reaching full inhibition of contact phase of coagulation, these nanogels were able to improve the effect of non-coated surfaces.

Example 19: PEG Thiol Ligands are Superior to Polybetaines to Prevent Biofilm Formation The data presented here indicates that grafting of PEG 2000 onto nanogel assembly could confer anti-adhesive properties to surfaces against both platelets and bacteria. A further comparison was made taking PEG 2000 as a reference, to polybetaines of different chain size and molecular weight. Biofilm formation was first assessed using the IVIS Lumina system and bioluminescent *S. aureus* bacteria (FIG. 36). This technique enabled us the kinetics of bacteria adhesion on a test surface to be followed. As shown in FIG. 36, PEG 2000 remained the best anti-biofilm ligand among all polybetaines tested.

Example 20: PEG Thiol Ligands are Superior to Polybetaines to Prevent Platelet Adhesion Under Flow Conditions Similarly as above, the efficacy of polybetaine ligands of different chain size and molecular weight to prevent platelet adhesion under flow conditions was assessed (FIG. 37). It was observed that PEG 2000 was superior to any of the polybetaines in terms of surface coverage and size of platelet aggregates formed on the surface. In contrast, no difference was observed between thiol end PEG and polybetaines when assessing platelet adhesion under static conditions (FIG. 38).

Example 21: PEG Ligands with Thiol Functionalized Ends are Superior to Polybetaines in Terms of Coagulation It was shown that among thiol end PEG ligands, PEG 2000 produced the lowest activation of coagulation (FIG. 35). PEG 2000 with thiol end polybetaines of increasing chain size and molecular weight were also compared. FIG. 39 shows no effect of the size of the chain with the polybetaine polymer, while it was confirmed that PEG 2000 did not produce more contact phase activation than basal plasma that has not been in contact with the surface of the PS wells.

Example 22: PEG Ligands with Thiol Functionalized Ends are Superior to Polybetaines to Prevent Plasma Protein Adhesion When plasma or blood comes in contact with a foreign surface the first event is protein adsorption, which promotes platelet adhesion, and leads to the activation of the intrinsic cascade of coagulation. Therefore, testing plasma protein adherence is an important step in the development of hemocompatible devices.

The surface of polystyrene wells was coated or not with 5-layer nanogels bearing or not PEG or polybetaine of different molecular weights as last top layer. This test is in line with the general idea that the length of a grafted polymer could prevent non-specific adsorption of proteins. Our results indicate that PEG 2000 (NG-P2) and 5000 (NG-P5) improve antifouling property of the surface as compared to nanogels without grafted polymer (NG), whilst polybetaines (NG-PB7, 15, 44) could not (FIG. 40).

It will be appreciated that reference in the examples to nanogels can also be replaced with reference to nanoreservoirs. The reader will appreciate that the term nanogels can be used to refer to a nanoreservoir comprising nanoparticles made from nanogel.

Other embodiments are intentionally within the scope of the invention as defined by the appended claims.

The invention claimed is:

1. A biomaterial implant, medical device or bioprosthesis wherein a surface or part thereof is coated with a reticulated nanoreservoir, the reticulated nanoreservoir comprising more than one layer of nanoparticles of a nanogel, wherein the nanogel comprises a first polymer of a Formula I, wherein the first polymer of Formula I comprises a main chain comprising a hydrophilic polymer backbone or a copolymer backbone:

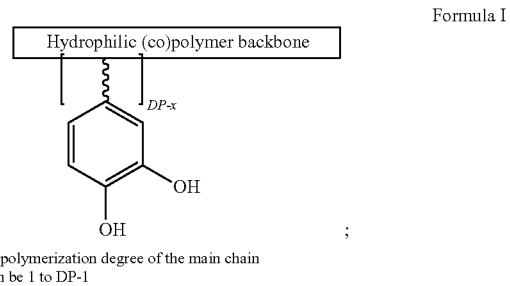

Formula I with DP = polymerization degree of the main chain
and x = can be 1 to DP-1 crosslinked to a second polymer comprising a hydrophilic backbone and one or more reactive moieties, wherein the reticulated nanoreservoir further comprises one or more bioactive molecules, therapeutic molecules or drugs that are continuously released from within the reticulated nanoreservoir.

2. The nanoreservoir of claim 1, wherein the nanoparticles have a diameter of 100 nm to 250 nm.

3. The nanoreservoir of claim 1, wherein at least some of the nanoparticles are decorated with a hydrophilic functionalized ligand.

4. The nanoreservoir of claim 3, wherein the hydrophilic functionalised ligands is a thiol or vinyl end functionalised ligand.

5. The nanoreservoir of claim 4, wherein hydrophilic functionalised ligand is PEG2 or a PEG with molecular weight greater than 2000.

6. The biomaterial implant, medical device or bioprosthesis of claim 1, wherein the bioprosthesis is a heart valve or a catheter.

7. The biomaterial implant, medical device or bioprosthesis of claim 1, wherein the reticulated nanoreservoir contains an antibiotic and/or an anti-platelet agent.

8. The biomaterial implant, medical device or bioprosthesis of claim 1, wherein the first polymer is P(mDOPA).

9. The biomaterial implant, medical device or bioprosthesis of claim 1, wherein the second polymer is poly(allylamine hydrochloride).

10. The biomaterial implant, medical device or bioprosthesis of claim 1, wherein the hydrophilic polymer or copolymer backbone of the reticulated nanoreservoir comprises one or more of polyallylamine, polyvinylamines, polyvinylamides, polyvinylalcohol, poly(meth)acrylates, poly(meth)acrylamide, PEG, a cationic polyelectrolyte, an anionic electrolyte, a zwitterionic electrolyte, chitosan, or hyaluronan.

11. A method of making the nanoreservoir of claim 1, comprising at least two bioactive molecules, therapeutic molecules or drugs, the method comprising the steps of:
   i) mixing Pox(mDOPA) in an aqueous solution with one bioactive molecule, therapeutic molecule or drug:
   ii) adding a PAH solution to the resulting aqueous solution of Pox(mDOPA) obtained in i) to form a first nanogel solution;
   iii) repeating steps i) and ii) with a second bioactive molecule, therapeutic molecule or drug to form a second nanogel solution;
   iv) mixing the first and second nanogel solutions to obtain a nanoreservoir with two bioactive molecules, therapeutic molecules or drugs.

12. A method of producing the medical device, biomaterial implant or bioprosthesis with a coated surface of claim 1 comprising
   i) dipping the surface to be coated in a solution of a first polymer, wherein the first polymer comprises a polymer of a Formula I:

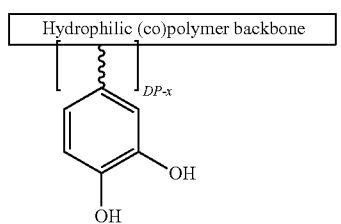

Formula I with DP = polymerization degree of the main chain
and x = can be 1 to DP-1 ii) oxidising the first polymer;
   iii) dipping the resulting surface in a second polymer solution wherein the second polymer comprises a hydrophilic backbone and one or more reactive moieties;
   iv) dipping the surface in nanoreservoir solution comprising nanoparticles of a nanogel, wherein the nanogel comprises a first polymer of a Formula I:

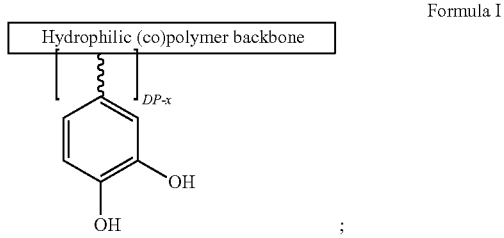

Formula I with DP = polymerization degree of the main chain
and x = can be 1 to DP-1 crosslinked to a second polymer comprising a hydrophilic backbone and one or more reactive moieties to produce a coating on the surface; and
   v) optionally dipping the coated surface in a solution of hydrophilic functionalized ligand.

13. The method of claim 12 wherein in step i) the first polymer is P(mDOPA); and/or is step ii) the oxidised polymer is Pox(mDOPA); and/or in step iii) the second polymer is PAH; in step iv) the nanoreservoir comprises nanoparticles of crosslinked Pox(mDOPA) and PAH, and optionally has the formula of one or both of:

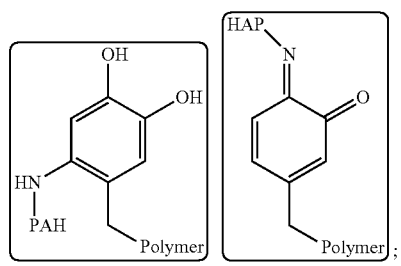

and/or wherein in step v) the hydrophilic functionalized ligand is PEG2 or a PEG with a MW of greater than 2000.

* * * * *